(12) United States Patent
Rothenberg et al.

(10) Patent No.: US 9,928,344 B2
(45) Date of Patent: Mar. 27, 2018

(54) DIAGNOSTIC METHODS OF EOSINOPHILIC ESOPHAGITIS

(75) Inventors: Marc E. Rothenberg, Cincinnati, OH (US); Ting Wen, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 341 days.

(21) Appl. No.: 14/128,322

(22) PCT Filed: Jun. 21, 2012

(86) PCT No.: PCT/US2012/043640
§ 371 (c)(1),
(2), (4) Date: Apr. 23, 2014

(87) PCT Pub. No.: WO2012/177945
PCT Pub. Date: Dec. 27, 2012

(65) Prior Publication Data
US 2015/0045334 A1    Feb. 12, 2015

Related U.S. Application Data

(60) Provisional application No. 61/571,115, filed on Jun. 21, 2011.

(51) Int. Cl.
*G06F 19/00* (2018.01)
*C12Q 1/68* (2018.01)
(Continued)

(52) U.S. Cl.
CPC ....... *G06F 19/3431* (2013.01); *C12Q 1/6883* (2013.01); *G01N 33/49* (2013.01);
(Continued)

(58) Field of Classification Search
None
See application file for complete search history.

(56) References Cited

U.S. PATENT DOCUMENTS 7,514,209 B2 *  4/2009  Dai .................... C12Q 1/6886
                                                     435/6.14
8,030,003 B2    10/2011  Rothenberg et al.
(Continued)

FOREIGN PATENT DOCUMENTS

WO    WO 2006/119343     11/2006
WO    WO-2009015434 A1   2/2009
(Continued)

OTHER PUBLICATIONS

SK Gupta, JF Fitzgerald, T Kondratyuk, H HogenEsch. Cytokine Expression in Normal and Inflamed Esophageal Mucosa: A Study into the Pathogenesis of Allergic Eosinophilic Esophagitis. Journal of Pediatric Gastroenterology and Nutrition. 2006, vol. 42, p. 22-26.*

(Continued)

*Primary Examiner* — John S. Brusca
*Assistant Examiner* — Olivia M Wise
(74) *Attorney, Agent, or Firm* — Mintz Levin Cohn Ferris Glovsky and Popeo, P.C.; Muriel Liberto, Esq.

(57) ABSTRACT

Embodiments of the invention are directed to methods of diagnosing eosinophilic esophagitis (EoE), or remission therefrom in a subject, wherein the methods include applying a sample from the subject to a diagnostic panel that contains selected markers for EoE, analyzing to obtain relatedness information relative to an EoE cohort and making a determination as to the EoE status of the subject, wherein an analysis indicating grouping with an EoE cohort or a quantitative score similar to that of an EoE cohort are indicative of EoE in the subject. Embodiments of the invention are also directed to methods of monitoring the pathological development or medical prognosis of EoE in a subject.

40 Claims, 25 Drawing Sheets

(51) Int. Cl.
  G01N 33/68   (2006.01)
  G01N 33/49   (2006.01)
  G01N 33/493  (2006.01)
  G06F 19/20   (2011.01)

(52) U.S. Cl.
  CPC ....... *G01N 33/493* (2013.01); *G01N 33/6893* (2013.01); *G06F 19/20* (2013.01); *C12Q 2600/106* (2013.01); *C12Q 2600/158* (2013.01); *G01N 2800/06* (2013.01); *G01N 2800/14* (2013.01); *G01N 2800/24* (2013.01); *G01N 2800/52* (2013.01); *G01N 2800/56* (2013.01)

(56) References Cited

U.S. PATENT DOCUMENTS

| | | |
|---|---|---|
| 2009/0269774 A1 | 10/2009 | Rothenberg et al. |
| 2011/0195500 A1 | 8/2011 | Rothenberg |
| 2011/0301046 A1 | 12/2011 | Rothenberg et al. |
| 2012/0004205 A1 | 1/2012 | Rothenberg |
| 2012/0283117 A1* | 11/2012 | Rothenberg ......... C12Q 1/6883 506/9 |
| 2013/0324435 A1 | 12/2013 | Rothenberg et al. |

FOREIGN PATENT DOCUMENTS

| | | |
|---|---|---|
| WO | WO-2009018493 A1 | 2/2009 |
| WO | WO-2009061819 A1 | 5/2009 |
| WO | WO 2012/094643 | 7/2012 |
| WO | WO 2012/174549 | 12/2012 |

OTHER PUBLICATIONS

GeneSpring User Manual, version 6.1. Silicon Genetics. Nov. 14, 2003.*
D Sinicropi, M Cronin, ML Liu. Gene Expression Profiling Utilizing Microarray Technology and RT-PCR. BioMEMS and biomedical nanotechnology. Springer US, 2006. 23-46.*
A Ben-Dor, L Bruhn, N Friedman, I Nachman, M Schummer, Z Yakhini. Tissue Classification with Gene Expression Profiles. Journal of Computational Biology. 2000, vol. 7, Nos. 3/4, p. 559-583.*
JM Caldwell, C Blanchard, MH Collins, PE Putnam, A Kaul, SS Aceves, CA Bouska, ME Rothenberg. Glucocorticoid-regulated genes in eosinophilic esophagitis: A role for FKBP51. J Allergy Clin Immuonl, Apr. 2010, vol. 125, No. 4, p. 879-888.*
ME Rothenberg et al. Common variants at Eq22 associate with pediatric eosinophilic esophagitis. Nature Genetics, 2010, vol. 42, No. 4, p. 289-291.*
Abonia et al., "Involvement of mast cells in eosinophilic esophagitis," J. Allergy Clin. Immunol., Jul. 2010, pp. 140-149, vol. 126(1).
April et al., "Whole-genome gene expression profiling of formalin-fixed, paraffin-embedded tissue samples," PLoS One, Dec. 3, 2009, pp. e8162, vol. 4(12).
Armour et al., "Expression of human FcgammaRIIIa as a GPI-linked molecule on CHO cells to enable measurement of human IgG binding," J. Immunol. Methods, Mar. 31, 2010, pp. 20-33, vol. 354(1-2).
Aune et al., "Epigenetics and T helper 1 differentiation," Immunology, Mar. 2009, pp. 299-305, vol. 126(3).
Blanchard et al., "A striking local esophageal cytokine expression profile in eosinophilic esophagitis," J. Allergy Clin. Immunol., Jan. 2011, pp. 208-217, vol. 127(1).
Blanchard et al., "Eotaxin-3 and a uniquely conserved gene-expression profile in eosinophilic esophagitis," J. Clin. Invest., Feb. 2006, pp. 536-547, vol. 116(2).
Blanchard et al., "IL-13 involvement in eosinophilic esophagitis: transcriptome analysis and reversibility with glucocorticoids," J. Allergy Clin. Immunol., Dec. 2007, pp. 1292-1300, vol. 120(6).
Blanchard et al., "Periostin facilitates eosinophil tissue infiltration in allergic lung and esophageal responses," Mucosal Immunol., Jul. 2008, pp. 289-296, vol. 1(4).
Chehade et al., "Food allergy and eosinophilic esophagitis," Curr. Opin. Allergy Clin. Immunol., Jun. 2010, pp. 231-237, vol. 10(3).
DeBrosse et al., "Identification, epidemiology, and chronicity of pediatric esophageal eosinophilia, 1982-1999," J. Allergy Clin. Immunol., Jul. 2010, pp. 112-119, vol. 126(1).
Fuentebella et al., "Increased number of regulatory T cells in children with eosinophilic esophagitis," J. Pediatr. Gastroenterol. Nutr., Sep. 2010, pp. 283-289, vol. 51(3).
Furuta et al., "Eosinophilic esophagitis in children and adults: a systematic review and consensus recommendations for diagnosis and treatment," Gastroenterology, Oct. 2007, pp. 1342-1363, vol. 133(4).
Liacouras et al., "Eosinophilic esophagitis: updated consensus recommendations for children and adults," J. Allergy Clin Immunol., Jul. 2011, pp. 3-20, vol. 128(1).
Lucendo et al., "Montelukast was inefficient in maintaining steroid-induced remission in adult eosinophilic esophagitis," Dig. Dis. Sci., Dec. 2011, pp. 3551-3558, vol. 56(12).
Molina-Infante et al., "Overlap of reflux and eosinophilic esophagitis in two patients requiring different therapies: A review of the literature," World J. Gastroenterol., Mar. 7, 2008, pp. 1463-1466, vol. 14(9).
Mulder et al., "Understanding eosinophilic esophagitis: the cellular and molecular mechanisms of an emerging disease," Mucosal. Immunol., Mar. 2011, pp. 139-147, vol. 4(2).
Ramirez et al., "Transcriptional regulation of the human alpha2(I) collagen gene (COL1A2), an informative model system to study fibrotic diseases," Matrix Biol., Aug. 2006, pp. 365-372, vol. 25(6).
Rodrigo et al., "High intraepithelial eosinophil counts in esophageal squamous epithelium are not specific for eosinophilic esophagitis in adults," Am. J. Gastroenterol., Feb. 2008, pp. 435-442, vol. 103(2).
Sprenger et al., "Eosinophilic oesophagitis: an enigmatic, emerging disease," Neth. J. Med., Jan. 2009, pp. 8-12, vol. 67.
Straumann et al., "Budesonide is effective in adolescent and adult patients with active eosinophilic esophagitis," Gastroenterology, Nov. 2010, pp. 1526-1537, vol. 139(5).
Straumann et al., "Long-term budesonide maintenance treatment is partially effective for patients with eosinophilic esophagitis," Clin. Gastroenterol. Hepatol., May 2011, pp. 400-409, vol. 9(5).
Straumann et al., "Pediatric and adult eosinophilic esophagitis: similarities and differences," Allergy, Apr. 2012, pp. 477-490, vol. 67(4).
Von Ahlfen et al., "Determinants of RNA quality from FFPE samples," PLoS One, Dec. 5, 2007, pp. e1261, vol. 2(12).
Zuo et al., "IL-13 induces esophageal remodeling and gene expression by an eosinophil-independent, IL-13R alpha 2-inhibited pathway," J. Immunol., Jul. 1, 2010, pp. 660-669, vol. 185(1).

* cited by examiner

|        | Path NL          | Path EoE           |          |
|--------|------------------|--------------------|----------|
| EDP NL | 48               | 7                  | NPV 87.3% |
| EDP EoE| 2                | 75                 | PPV 97.4% |
|        | Specificity 96%  | Sensitivity 91.5%  |          |

Fig. 9D

DIAGNOSTIC METHODS OF EOSINOPHILIC ESOPHAGITIS

CROSS REFERENCE TO RELATED APPLICATION

The present application is a U.S. National Stage entry under 35 U.S.C. § 371 of International Application No. PCT/US2012/043640, filed on Jun. 21, 2012, designating the United States of America and published in English on Dec. 27, 2012, which in turn claims the benefit of priority under 35 U.S.C. § 119(e) to U.S. Provisional Application No. 61/571,115, DIAGNOSTIC METHODS OF EOSINOPHILIC ESOPHAGITIS, filed on Jun. 21, 2011, which is currently herewith and each of which is incorporated by reference in its entirety.

STATEMENT REGARDING FEDERALLY-SPONSORED RESEARCH

This invention was made with government support under AI045898, AI083450, DK078392, DK076893, and AI070235 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Dec. 20, 2013, is named Sequence_Listing-0088544-010US0.txt and is 622 kilobytes in size.

FIELD OF THE INVENTION

The invention disclosed herein generally relates to methods and compositions for diagnosis of an eosinophilic esophagitis (EoE) disease state in a subject.

BACKGROUND

Eosinophilic esophagitis (EoE, also referred to as EE in some publications) is a recently identified clinico-pathological gastrointestinal (GI) allergic disease characterized by pronounced eosinophil infiltration locally restricted in the esophagus. EoE is often defined based upon an artificial threshold of >15 eosinophils/HPF in patients who have had acid-induced esophageal injury excluded as a cause for the esophageal histology (Furuta, et al. *Gastroenterology* 133: 1342-63 (2007)). It has been estimated that nearly 1:1000 individuals in the western world may have EoE, which likely accounts for the approximately 10-30% of chronic esophagitis cases that are found to be refractory to proton pump inhibitor (PPI) therapy.

The treatment of EoE is distinct from other forms of esophagitis, as effective management depends upon elimination of the triggering food types or the usage of anti-inflammatory medications (e.g. glucocorticoids). Accordingly, it is important to differentiate EoE from other gastrointestinal afflictions, such as gastroesophageal reflux disease (GERD). Unfortunately, EoE diagnosis relies upon histological analysis of esophageal biopsies, which requires the uncomfortable procurement of up to 5 biopsies to obtain sufficient sensitivity for diagnosis of the disease. In addition, a histological finding is not specific for EoE, as it is determined by methods that depend upon variable biopsy procurement and subjective microscopic review of biopsies and features that can be common to other esophageal disorders. This is because esophageal eosinophilia is not specific to EoE, as eosinophil migration into the esophagus also occurs in other disease processes, including GERD, infections, and auto-immune diseases, which complicates diagnosis based upon eosinophil detection. Furthermore, exposure to specific drugs, especially anti-inflammatory agents, which can affect tissue histology, cannot be directly derived by microscopic analysis of biopsy specimens (Rodrigo, et al. *Am. J. Gastroenterol.* 103:435-42 (2008)).

Accordingly, there is a need for development of diagnostic procedure options that are fast, efficient, inexpensive, and able to improve the diagnostic specificity for EoE. Such methods ideally can also be used to distinguish EoE over other esophageal disorders.

SUMMARY OF THE INVENTION

Methods and compositions described herein are provided by way of example and should not in any way limit the scope of the invention.

Embodiments of the invention encompass methods of diagnosing eosinophilic esophagitis (EoE) in a subject, including: applying a sample from the subject to a diagnostic panel that includes at least one marker or gene selected from Table 1 to obtain a result; analyzing the results to obtain relatedness information relative to an EoE cohort; and making a determination as to the EoE status of the subject, wherein an analysis indicating grouping with an EoE cohort or a quantitative score similar to that of an EoE cohort are indicative of EoE in the subject.

In some embodiments of the methods, the results can be analyzed by at least one algorithm. In some embodiments, the at least one algorithm can be selected from the group of: a cluster analysis algorithm, a cumulative quantification algorithm, and any combination thereof, and a cluster analysis indicating grouping with an EoE cohort and/or a quantitative score which provides greater than 90% sensitivity and greater than 90% specificity based upon ROC analysis for an EoE cohort can be indicative of EoE in the subject.

In some embodiments, the at least one marker or gene can be mRNA. In some embodiments, the at least one marker or gene can be protein.

In some embodiments, the subject can be a patient. In some embodiments the patient can be a human patient.

In some embodiments, the sample can be a tissue, an exudate, saliva, serum, plasma, mucus, blood, urine, oral, or a buccal sample. In some embodiments, the sample can be a tissue sample. In some embodiments, the tissue sample can be an esophageal tissue sample.

In some embodiments, a subset of the markers or genes in Table 1 can be analyzed by the algorithms for making the determination. In some embodiments, a subset of 77 or fewer markers or genes from Table 1 can be analyzed. In some embodiments, a subset of 32 or fewer markers or genes from Table 1 can be analyzed.

In some embodiments, the result includes information from at least two markers or genes selected from Table 1. In some embodiments, the result includes information from at least 10 markers or genes selected from Table 1. In some embodiments, the result includes information from at least 30 markers or genes selected from Table 1. In some embodiments, the result includes information from at least 60 markers or genes selected from Table 1. In some embodiments, the result includes information from all of the markers or genes listed in Table 1.

In some embodiments, the result includes information from at least one marker or gene selected from Table 2. In some embodiments, the result includes information from 2 to 77 markers or genes.

In some embodiments, the result includes information from at least one marker or gene selected from Table 4. In some embodiments, the result includes information from 2 to 32 markers or genes.

In some embodiments, the result includes information from all of the markers or genes listed in Table 2. In some embodiments, the result includes information from all of the markers or genes listed in Table 4.

Some embodiments of the invention include detecting, from the patient sample, a level of eotaxin-3 mRNA expression or eotaxin-3 protein.

In some embodiments, the determination includes distinguishing EoE in the subject from at least one other esophageal disorder. In some embodiments, the other esophageal disorder can be gastroesophageal reflux disease (GERD).

In some embodiments, the determination includes determining the presence of EoE in the subject in association with at least one other eosinophilic gastrointestinal disorder (EGID). In some embodiments, the determination includes determining the presence of EoE in the subject in association with at least one other inflammatory gastrointestinal disorder. In some embodiments, the at least one other inflammatory gastrointestinal disorder can be celiac disease or inflammatory bowel disease.

Some embodiments of the invention include monitoring or guiding treatment for a subject suffering from EoE by developing or modifying a therapy for the subject based upon the combined results of the diagnostic panel and the at least one algorithm. In some embodiments, the monitoring of treatment includes identifying exposure to a specific therapy. In some embodiments, the specific therapy includes glucocorticoid administration therapy. In some embodiments, the specific therapy includes dietary therapy. In some embodiments, the specific therapy includes a therapy that targets at least one molecule involved in EoE disease pathogenesis and/or at least one downstream gene affected by the same.

In some embodiments, the determination includes determining whether the subject has entered remission from EoE. In some embodiments, the determination includes determining presence of inactive EoE relative to normal molecular pathology in the subject.

In some embodiments, the sample can be an archival sample. In some embodiments, the archival sample can be a formalin-fixed, paraffin-embedded (FFPE) sample.

Some embodiments of the invention include developing or modifying a therapy for the subject based upon the determination. In some embodiments, the determination includes a determination of compliance with medical management in a subject undergoing therapy for EoE. In some embodiments, the determination includes a determination and/or monitoring of exposure to one or more therapeutic compounds in the subject, wherein the cluster analysis can be indicative of the exposure.

Some embodiments of the invention include providing personal prognostic medicine guidance to the subject, based upon the determination, and wherein the personal prognostic medicine guidance includes developing and/or modifying a therapy or predicting prognosis for the subject based upon the determination.

Some embodiments of the invention include determining the specific genes engaged by a therapeutic, wherein the therapeutic can be administered to the subject, and a sample from the subject following therapeutic administration can be subjected to the same diagnostic panel in order to obtain a result, wherein differences between the two results can determine the specific genes engaged by the administered therapeutic. In some embodiments, the results are analyzed by comparison with normal and EoE cohorts to identify genes that are up- or down-regulated in response to environmental factors.

Embodiments of the invention also encompass methods of determining tissue fibrosis and/or remodeling in a subject, including: applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the KRT23, COL1A2, or COL8A2 markers or genes relative to a normal cohort or an EoE cohort can be indicative of tissue fibrosis and/or remodeling.

Embodiments of the invention also encompass methods of treating a subject with tissue fibrosis and/or remodeling, including applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the KRT23, COL1A2, or COL8A2 markers or genes relative to a normal cohort or an EoE cohort can be indicative of tissue fibrosis and/or remodeling, and additionally including administering to the subject a therapy that targets at least one of the KRT23, COL1A2, and COL8A2 markers or genes.

Embodiments of the invention also encompass methods of determining abnormal mast cell function and/or mastocytosis in a subject, including: applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the TPSB2;TPSAB1, CPA3, and CMA1 markers or genes relative to a normal cohort or an EoE cohort can be indicative of abnormal mast cell production and/or mastocytosis.

Embodiments of the invention also encompass methods of treating a subject with abnormal mast cell production and/or mastocytosis, including applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the TPSB2;TPSAB1, CPA3, and CMA1 markers or genes relative to a normal cohort or an EoE cohort can be indicative of abnormal mast cell production and/or mastocytosis, and additionally including administering to the subject an anti-mast cell therapy. In some embodiments, the anti-mast cell therapy can be a therapy that targets at least one of the TPSB2;TPSAB1, CPA3, and CMA1 markers or genes.

Embodiments of the invention also encompass methods of determining abnormal natural killer (NK) cell production in a subject, including: applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the FCGR3B;FCGR3A, SLAMF7, and NCAM1 markers or genes relative to a normal cohort or an EoE cohort can be indicative of abnormal NK cell production.

Embodiments of the invention also encompass methods of treating a subject with abnormal NK cell production, including applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the FCGR3B;FCGR3A, SLAMF7, and NCAM1 markers or genes relative to a normal cohort or an EoE cohort can be indicative of abnormal NK cell production, and additionally including administering to the subject an anti-NK cell therapy. In some embodiments, the anti-NK cell therapy can be a therapy that targets at least one of the FCGR3B; FCGR3A, SLAMF7, and NCAM1 markers or genes.

Embodiments of the invention also encompass methods of determining abnormal T lymphocyte production in a subject, including: applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the IL4, IL5, and IL13 markers or genes relative to a normal cohort or an EoE cohort can be indicative of abnormal T lymphocyte production.

Embodiments of the invention also encompass methods of treating a subject with abnormal T lymphocyte production, including applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the IL4, IL5, and IL13 markers or genes relative to a normal cohort or an EoE cohort can be indicative of abnormal T lymphocyte production, and additionally including administering to the subject an anti-T lymphocyte therapy. In some embodiments, the anti-T lymphocyte therapy can be a therapy that targets at least one of the IL4, IL5, and IL13 markers or genes.

Embodiments of the invention also encompass methods of determining abnormal production of a specific type of cell in a subject, including: applying a sample from the subject to a diagnostic panel that includes at least one marker or gene selected from Table 1 to obtain a result; and analyzing the results to obtain relatedness information relative to a normal cohort or an EoE cohort, wherein elevated levels of at least marker or gene associated with the specific cell type relative to a normal cohort or an EoE cohort can be indicative of abnormal production of the specific cell type.

Embodiments of the invention also encompass methods of treating a subject with abnormal production of a specific cell type, including applying a sample from the subject to a diagnostic panel that includes at least one marker or gene selected from Table 1 to obtain a result; and analyzing the results to obtain relatedness information relative to a normal cohort or an EoE cohort, wherein elevated levels of at least marker or gene associated with the specific cell type relative to a normal cohort or an EoE cohort can be indicative of abnormal production of the specific cell type, and additionally including administering to the subject a therapy targeting the specific cell type.

Embodiments of the invention also encompass an EoE molecular diagnostic panel including at least one marker or gene selected from Table 1. Embodiments of the invention also encompass an EoE molecular diagnostic panel including at least one marker or gene selected from Table 2. Embodiments of the invention also encompass an EoE molecular diagnostic panel including at least one marker or gene selected from Table 4. Embodiments of the invention also encompass an EoE molecular diagnostic panel including eotaxin-3 mRNA and at least one marker or gene selected from Table 1.

Embodiments of the invention also encompass a tissue pathology molecular diagnosis panel including at least one marker or gene selected from Table 1. In some embodiments, the tissue pathology molecular diagnosis panel includes at least one marker or gene selected from KRT23, COL1A2, COL8A2, TPSB2;TPSAB1, CPA3, CMA1, FCGR3B;FCGR3A, SLAMF7, and NCAM1. In some embodiments, the tissue pathology molecular diagnosis panel can include all of the KRT23, COL1A2, COL8A2, TPSB2;TPSAB1, CPA3, CMA1, FCGR3B;FCGR3A, SLAMF7, and NCAM1 markers or genes.

BRIEF DESCRIPTION OF THE DRAWINGS

Those of skill in the art will understand that the drawings, described below, are for illustrative purposes only. The drawings are not intended to limit the scope of the present teachings in any way.

FIG. 2A depicts a statistical screening performed between 14 normal (NL) and 15 EoE patients for the 94 EoE genes embedded, resulting in 77 genes. Based on these 77 core genes, a heatmap was created with Pearson Centered distance metrics, with the hierarchical tree (dendrogram) established on both gene entities and sample conditions. FIG. 2B depicts the 77-gene/dimension expression data on 14 normal and 15 EoE patients reduced to 3-D presentation by multi-dimensional scaling (MDS, Euclid distance-based) analysis for visual presentation of the expression distance between any two given samples. FIG. 2C depicts the EoE score developed based on dimensionality reduction to distinguish EoE vs. NL and quantify EoE disease severity. FIG. 2D depicts levels of distal esophagus eosinophilia. FIG. 2E depicts a receiver operating characteristic (ROC) curve based on FIG. 2C and the EoE score=333 cut-off. FIG. 2F depicts a linear correlation between eosinophils/HPF and EoE score. FIG. 2G depicts a representative linear regression regarding mast cell gene intra-correlation (CPA3 vs. tryptase, TPSB2), mast cell gene/eosinophil gene inter-correlation (CPA3 vs. CLC), and eosinophil gene/eosinophilia correlation (CLC vs. eosinophils/HPF).

FIG. 3A depicts a cluster analysis performed on a heatmap to provide diagnosis for 8 unknown samples. FIG. 3B depicts EoE scores calculated in the unknown 8 patients with NL and EoE algorithm developing cohorts as reference. FIG. 3C depicts a heatmap of two RNA samples (I and II) taken with a different fluidic card at different times a half-year apart (data A and data B) and run in different batches. FIG. 3D depicts the Bland-Altman analysis of repetitive sets of expression data from sample I and II plotted on raw Ct value of 96 genes (x-axis) vs. the difference between raw Ct value A and the average of Ct value A and B. FIG. 3E depicts raw Ct values for each of the 96 genes from sample I and II double-plotted between the two repetitions and subjected to linear regression analysis.

FIG. 4A depicts a double-clustered heatmap generated to evaluate the gene expression pattern of EoE remission compared to NL and EoE patients. FIG. 4B depicts the remission score (EoE R score) based on the 22 steroid remission genes for each patient as calculated by 1-D reduction to differentiate the remission patients from NL patients quantitatively. FIG. 4C depicts a ROC curve with a diagnostic cutoff line of EoE R score=74. FIG. 4D depicts EoE scores calculated to assess the EoE status of remission patients based on the 77 EoE diagnostic genes.

FIG. 5A depicts a cluster analysis of 8 FFPE samples based on the previously mentioned 77 core EoE genes. FIG. 5B depicts a cluster analysis of the 8 FFPE EoE and NL samples relative to fresh EoE and NL samples based on the 77 significant genes derived from fresh samples. FIG. 5C depicts representative RNA quality with high purity from FFPE tissues. FIG. 5D depicts the same 1-D reduction method with fresh samples, with the EoE score derived from the 8 FFPE samples to compare to the algorithm for developing fresh NL and EoE samples.

FIG. 6A depicts EDP-based expression signatures for patients with esophageal biopsies that demonstrate 6-14 eosinophils/HPF without known previous diagnosis of EoE (6-14) and EoE patients in remission with 6-14 eosinophils/HPF (Remission 6-14), juxtaposed with the algorithm developing NL and EoE cohorts for visual comparison. FIG. 6B depicts an EoE score scatter plot based on using the ΣΔCt algorithm to assess EoE transcriptome occurrence within both ambiguous 6-14 eosinophils populations. FIG. 6C depicts a 3-D plot created by MDS analysis to visualize the 77 core EoE gene expression on 3-D plot. FIG. 6D depicts the average Euclid distances (permutation of all possible pairs) from both 6-14 cohorts (combined, with and without EoE history) to NL and EoE, respectively, graphed as mean±95% CI, revealing their collective Euclid distance to NL and EoE reference cohorts, respectively.

FIG. 7A depicts a molecular expression heatmap from 12 eosinophilia-matched adult active EoE patients acquired by EDP, juxtaposed to the heatmaps of algorithm developing pediatric EoE and pediatric NL cohorts for expression signature comparison. FIG. 7B depicts EoE scores calculated for adult EoE, pediatric EoE cohorts along with a pediatric NL cohort to compare the EoE signature in 1-D quantification. FIG. 7C depicts graphs of eosinophils/HPF for all 3 groups to shown the eosinophilia match in the two active EoE cohorts. FIG. 7D depicts the age distribution chart for all 3 groups analyzed herein. FIG. 7E depicts the expression profile of 77 core EoE genes from pediatric EoE and NL cohorts reduced to 2-D visualization by MDS analysis (upper panel) and MDS analysis performed between adult EoE and pediatric EoE with 2-D data plotted on the same scale (lower panel). FIG. 7F depicts expression of the 77 core EoE genes analyzed by principal component analysis (PCA), with the top 3 components graphed in 3-D space (upper panel) and PCA analysis performed between adult EoE and pediatric EoE on the expression profile of the 77 genes (lower panel).

FIG. 8A depicts an expression heatmap generated based on 44 significant genes after a statistical screening between NL and EoE for five study cohorts, namely normal (NL), symptomatic GERD (sGERD), GERD, EoE, and EoE plus gastroesophageal reflux (EoE+Reflux). FIG. 8B depicts the above 44 gene expression profiles of the five categories of patients subject to MDS analysis to reveal their 2-D-simulated Euclid distance of all 44 genes.

FIG. 9A depicts a double-clustered heat map. FIG. 9B depicts EoE scores from histology-definded 50 NL and 82 EoE patients plotted over the 333 diagnostic cut-off. FIG. 9C depicts a ROC curve with the diagnostic cutoff line of EoE R score=333. FIG. 9D depicts the EDP diagnostic merit as summarized in specificity vs. sensitivity and positive predictive value (PPV) vs. negative predictive value (NPV), reflecting the diagnosing power in clinical practice.

DETAILED DESCRIPTION OF THE INVENTION

Figure 1:
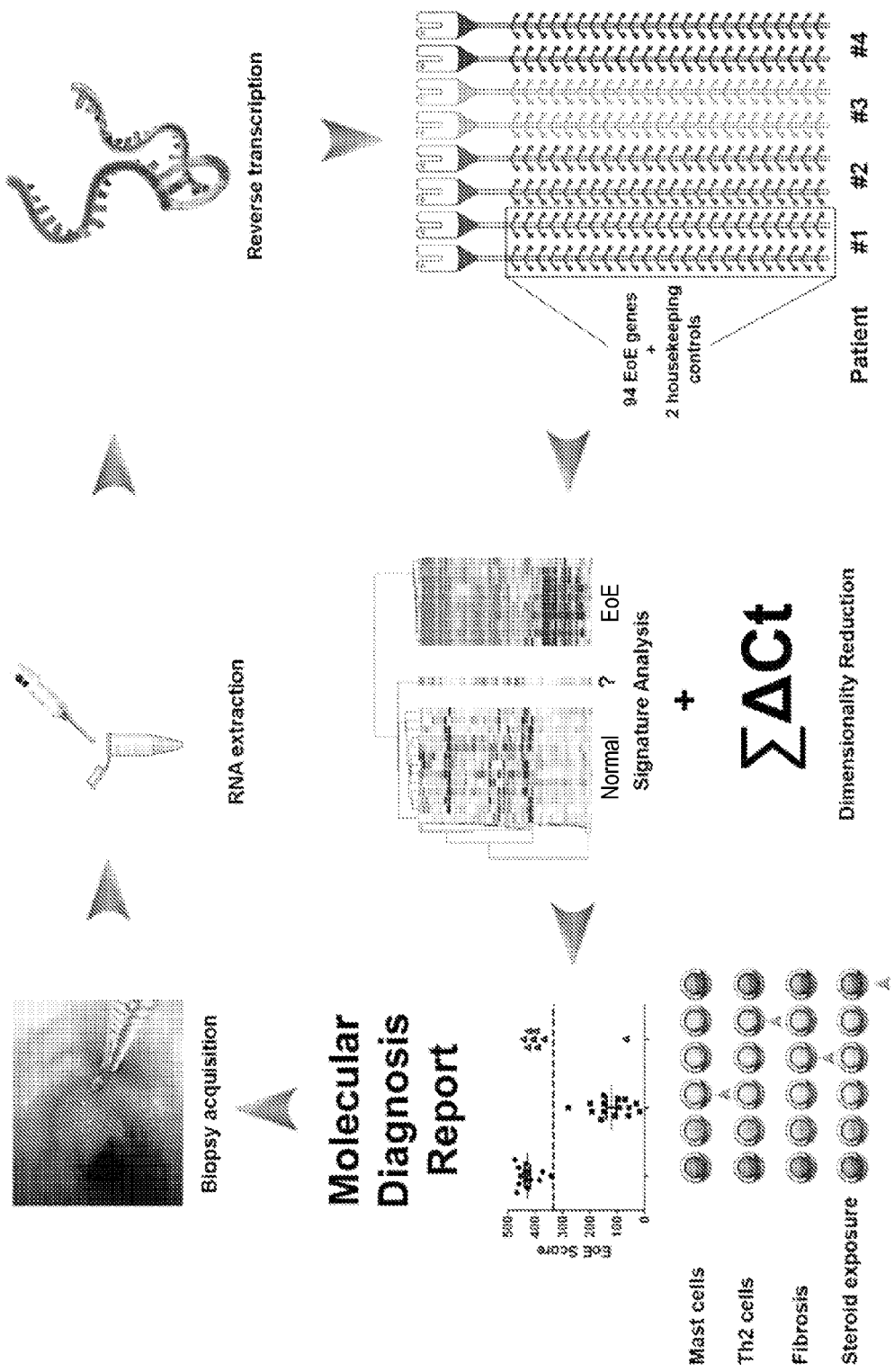
FIG. 1 depicts a schematic of a disclosed embodiment of the inventive subject matter, namely a graphical illustration of the EoE diagnostic panel (EDP) standard operating procedures. The 3 major steps of the EDP, namely RNA extraction, EDP panel qPCR, and data analysis, are shown. The picture in the biopsy acquisition panel was taken from Body-Philosophy (http <colon slash slash> www <dot> body-philosophy <dot> net). The picture in the RNA extraction panel was taken from Clker (http <colon slash slash> www <dot> clker <dot> com). The picture in the reverse transcription panel was taken from Science Photo Library (http <colon slash slash> www <dot> sciencephoto <dot> com).

All references cited herein are incorporated by reference in their entirety. Also incorporated herein by reference in their entirety include: U.S. Patent Application No. 60/633,909, EOTAXIN-3 IN EOSINOPHILIC ESOPHAGITIS, filed on Dec. 27, 2004; U.S. Pat. No. 8,030,003, DIAGNOSIS OF EOSINOPHILIC ESOPHAGITIS BASED ON PRESENCE OF AN ELEVATED LEVEL OF EOTAXIN-3, issued Oct. 4, 2011 and filed as U.S. patent application Ser. No. 11/721,127 on Jun. 7, 2007; U.S. patent application Ser. No. 12/492,456, EVALUATION OF EOSINOPHILIC ESOPHAGITIS, filed on Jun. 26, 2009; U.S. patent application Ser. No. 12/628,992, IL-13 INDUCED GENE SIGNATURE FOR EOSINOPHILIC ESOPHAGITIS, filed on Dec. 1, 2009; U.S. Provisional Application No. 61/430,453, A STRIKING LOCAL ESOPHAGEAL CYTOKINE EXPRESSION PROFILE IN EOSINOPHILIC ESOPHAGITIS, filed on Jan. 6, 2011; U.S. patent application Ser. No. 13/051,873, METHODS AND COMPOSITIONS FOR MITIGATING EOSINOPHILIC ESOPHAGITIS BY MODULATING LEVELS AND ACTIVITY OF EOTAXIN-3, filed on Mar. 18, 2011; U.S. patent application Ser. No. 13/132,884, DETERMINATION OF EOSINOPHILIC ESOPHAGITIS, filed on Jun. 3, 2011; U.S. Provisional Application No. 61/497,796, NEGATIVE REGULATION OF EOSINOPHIL PRODUCTION BY TOLL-LIKE RECEPTORS, filed on Jun. 16, 2011; U.S. patent application Ser. No. 13/132,295, METHODS OF DETERMINING EFFICACY OF GLUCOCORTICOID TREATMENT OF EOSINOPHILIC ESOPHAGITIS, filed on Aug. 22, 2011; PCT Patent Application No. US2012/020556, ESOPHAGEAL CYTOKINE EXPRESSION PROFILES IN EOSINOPHILIC ESOPHAGITIS, filed on Jan. 6, 2012; U.S. Provisional Application No. 61/602,897, ESOPHA- GEAL MICRORNA EXPRESSION PROFILES IN EOSINOPHILIC ESOPHAGITIS, filed on Feb. 24, 2012; and PCT Patent Application No. TBD, BLOCKAGE OF EOSINOPHIL PRODUCTION BY TOLL-LIKE RECEPTORS, filed on Jun. 18, 2012.

Unless otherwise noted, terms are to be understood according to conventional usage by those of ordinary skill in the relevant art.

As used herein, the term "sample" encompasses a sample obtained from a subject or patient. The sample can be of any biological tissue or fluid. Such samples include, but are not limited to, sputum, saliva, buccal sample, oral sample, blood, serum, mucus, plasma, urine, blood cells (e.g., white cells), circulating cells (e.g. stem cells or endothelial cells in the blood), tissue, core or fine needle biopsy samples, cell-containing body fluids, free floating nucleic acids, urine, stool, peritoneal fluid, and pleural fluid, liquor cerebrospinalis, tear fluid, or cells therefrom. Samples can also include sections of tissues such as frozen or fixed sections taken for histological purposes or microdissected cells or extracellular parts thereof. A sample to be analyzed can be tissue material from an esophageal tissue biopsy obtained by aspiration or punctuation, excision or by any other surgical method leading to biopsy or resected cellular material. Such a sample can comprise cells obtained from a subject or patient. In some embodiments, the sample is a body fluid that include, for example, blood fluids, serum, mucus, plasma, lymph, ascitic fluids, gynecological fluids, or urine but not limited to these fluids. In some embodiments, the sample can be a non-invasive sample, such as, for example, a saline swish, a buccal scrape, a buccal swab, and the like.

As used herein, the term "assessing" includes any form of measurement, and includes determining if an element is present or not. The terms "determining," "measuring," "evaluating," "assessing" and "assaying" can be used interchangeably and can include quantitative and/or qualitative determinations.

As used herein, the term "modulated" or "modulation," or "regulated" or "regulation" and "differentially regulated" refers to both up regulation (i.e., activation or stimulation, e.g., by agonizing or potentiating) and down regulation (i.e., inhibition or suppression, e.g., by antagonizing, decreasing or inhibiting), unless otherwise specified or clear from the context of a specific usage.

As used herein, the term "diagnosing or monitoring" with reference to eosinophilic esophagitis (EoE) refers to a method or process of determining if a subject has or does not have EoE, or determining the severity or degree of EoE, or determining the remission status of EoE.

As used herein, the term "subject" refers to any member of the animal kingdom. In some embodiments, a subject is a human patient.

As used herein, the terms "treatment," "treating," "treat," and the like, refer to obtaining a desired pharmacologic and/or physiological effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition.

As used herein, the term "transcriptome" refers to the set of all messenger RNA (mRNA) molecules, or "transcripts," produced in one or a population of cells. This term can also include non-translated RNAs which affect cellular characteristics because of gene regulation functions (silencing or activation or stabilization or degradation of other genes and transcripts). The term can be applied to the total set of transcripts in a given organism, or to the specific subset of transcripts present in a particular cell type. Unlike the genome, which is roughly fixed for a given cell line (excluding mutations), the transcriptome can vary with external environmental conditions. Because it includes all RNA transcripts in the cell, the transcriptome reflects the genes that are being actively expressed at any given time, with the exception of mRNA degradation phenomena such as transcriptional attenuation. It also includes posttranscriptional events such as alternative splicing.

As used herein, the term "expression levels" refers, for example, to a determined level of gene expression. The term "pattern of expression levels" refers to a determined level of gene expression compared either to a reference gene (e.g. a housekeeping gene or inversely regulated genes) or to a computed average expression value (e.g. in DNA-chip analyses). A pattern is not limited to the comparison of two genes but is more related to multiple comparisons of genes to reference genes or samples. A certain "pattern of expression levels" can also result and be determined by comparison and measurement of several genes as disclosed herein and display the relative abundance of these transcripts to each other.

As used herein, a "reference pattern of expression levels" refers to any pattern of expression levels that can be used for the comparison to another pattern of expression levels. In some embodiments of the invention, a reference pattern of expression levels is, for example, an average pattern of expression levels observed in a group of healthy or diseased individuals, serving as a reference group.

As used herein, the term "marker" or "biomarker" refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

Eosinophilic esophagitis (EoE) is an emerging disease, whose diagnostic standards are under debate. Currently, the ability to definitively diagnose EoE from other esophageal diseases is hindered by the overlapping clinical symptoms, endoscopic manifestations, histopathological characteristics, radiological and manometrical features, and perhaps even molecular expression profiles. Although expression levels of esophageal eotaxin-3 in one biopsy can identify the presence of EoE with remarkable sensitivity of 89% of the time, thus differentiating EoE from GERD (Blanchard et al. 2011. *J Allergy Clin Immunol* 127(1): 208-217, 217 e1-7, which is incorporated herein by reference in its entirety), this method is not always optimal in clinical applications.

As described herein, a readily-performed qPCR-based molecular platform called the EoE Diagnostic Panel (EDP) was developed. The EDP is capable of providing a differential diagnosis of EoE vs. normal patients (NL), EoE vs. gastroesophageal reflux disease (GERD) patients, and EoE remission vs. NL patients, by dual algorithms. The EDP was demonstrated to be compatible with formalin-fixed, paraffin-embedded (FFPE) samples by two independent sub-studies, showing that molecular diagnosis using FFPE samples had comparable merit to using fresh samples. The EDP was validated in adult and pediatric patient populations. The EDP data also demonstrated that around a third of the patient population with 6-14 eosinophils have an EoE-like transcriptome, suggesting that they should be tightly monitored as a population with high EoE risk. The EDP can be used alone or can be enhanced by combination with determination of eotaxin-3 mRNA expression levels or eotaxin-3 protein.

Embodiments of the invention are directed to methods for determining whether a subject is suffering from EoE. As described herein, based on a previously identified esophageal EoE transcriptome signature (Blanchard et al. 2006. *J Clin Invest* 116(2):536-547, which is incorporated herein by reference in its entirety) and aided by bioinformatics analysis, a selection of EoE representative genes was incorporated into a new platform, namely a low density Taqman-based qPCR array using a commercial 384-well fluidic card system (the EDP). The EDP was designed to include genes whose levels were indicative of a number of features, including, but not limited to, differentiation of EoE from normal patients as well as from patients suffering from gastroesophageal reflux disease (GERD) and other non-allergic esophageal inflammatory disease, as well as genes that identify specific cellular components (e.g. mast cells, eosinophils, and $T_H$ cells), the presence of tissue remodeling (keratin, collagen), the differentiation state of the epithelium, and whether there was patient exposure to glucocorticoid drugs. Embodiments of the invention also include methods for determining whether a subject is suffering from EoE by combining the results from the EDP with determination of eotaxin-3 mRNA expression levels or eotaxin-3 protein.

As further described herein, methods involving use of the developed EDP are able to provide molecular diagnosis between normal (NL) and EoE adult and pediatric biopsies with high sensitivity (92-100%) and specificity (96-100%). In addition, EoE remission patients (topical steroid responders with no esophageal eosinophila) were readily distinguishable from normal controls by unique molecular expression patterns, a discrimination that conventional methods cannot perform. Methods involving use of the EDP can also analyze mRNA in formalin-fixed paraffin-embedded (FFPE) biopsy samples, as described in an impedance-guided retrospective FFPE study to differentiate GERD from EoE, and therefore can be utilized to provide diagnosis from paraffin blocks with reliable accuracy. Finally, methods involving the EDP can be used to diagnose patients with borderline threshold numbers of eosinophils (i.e. 6-14 eosinophils/high-power field (HPF)), who are not normally diagnosed as having active EoE by histological methods, as 30-50% of such patients exhibit an EoE-like transcriptome. The methods developed herein involving the EDP are able to provide molecular diagnosis in a fast, affordable, objective, and mechanism-based manner and thus offer the opportunity to improve disease diagnosis and to molecularly monitor the degree of disease activity using a personalized medicine approach in patients with esophagitis.

As further described herein, the EDP, which was developed by selecting a representative EoE gene set on the 96-gene panel, was demonstrated to be sufficient to provide EoE diagnosis with high PPV and NPV, based on dual algorithms. Analysis of blinded specimens from routine clinical practice indicated that the EDP had high-merit and reproducibility. EoE remission patients can be readily distinguished from normal (NL) patients using the EDP even though both have no esophageal eosinophilia; this cannot be achieved by the conventional methods. In addition, ~30-50% of patients with equivocal eosinophil levels (6-14 eosinophils/HPF) had a signature suggestive of EoE. The EDP was also shown to be applicable for molecular diagnosis of archived FFPE tissue samples in addition to fresh biopsies and can provide insights about the ambiguous pathological specimens, such as those with eosinophil levels below the recommended diagnostic threshold (<15 eosinophil/HPF criterion), which has always been a debatable population with high risk for EoE. With this capacity and guided by impedance data, the differentiation between GERD and EoE was retrospectively demonstrated at transcriptome level. Adult EoE was also demonstrated to have a comparable signature compared to pediatric cases. These results demonstrate some embodiments of the invention relating to the use of the EDP in the classification of esophagitis and tailoring of personalized medicine.

Accordingly, embodiments of the invention are directed to methods of diagnosing eosinophilic esophagitis in a subject, wherein the methods comprise applying a sample from the subject to a diagnostic panel that includes markers selected from Table 1, analyzing the results to obtain relatedness information relative to an EoE cohort; and making a determination as to the EoE status of the subject, wherein an analysis indicating grouping with an EoE cohort or a quantitative score similar to that of an EoE cohort are indicative of EoE in the subject. In some embodiments, the results are combined with determination of eotaxin-3 mRNA expression levels or eotaxin-3 protein.

Embodiments of the invention are also directed to methods of distinguishing eosinophilic esophagitis from other esophageal disorders in a subject, wherein the methods comprise applying a sample from the subject to a diagnostic panel that includes markers selected from Table 1, analyzing the results to obtain relatedness information relative to an EoE cohort, and making a determination as to the EoE status of the subject, wherein an analysis indicating grouping with an EoE cohort or a quantitative score similar to that of an EoE cohort are indicative of EoE in the subject. In some embodiments, the other esophageal disorder is GERD.

Embodiments of the invention are also directed to methods of determining the presence of eosinophilic esophagitis in association with at least one other eosinophilic gastrointestinal disorder (EGID) or inflammatory gastrointestinal disorder, wherein the methods comprise applying a sample from the subject to a diagnostic panel that includes markers selected from Table 1, analyzing the results to obtain relatedness information relative to an EoE cohort, and making a determination as to the EoE status of the subject, wherein an analysis indicating grouping with an EoE cohort or a quantitative score similar to that of an EoE cohort are indicative of EoE in the subject.

Embodiments of the invention are also directed to methods of monitoring or guiding treatment for a subject suffering from EoE, wherein the methods comprise applying a sample from the subject to a diagnostic panel that includes markers selected from Table 1, analyzing the results to obtain relatedness information relative to an EoE cohort, and making a determination as to the EoE status of the subject, wherein an analysis indicating grouping with an EoE cohort or a quantitative score similar to that of an EoE cohort are indicative of EoE in the subject, and developing or modifying a therapy for the subject based upon the combined results of the diagnostic panel and at least one of the algorithms. In some embodiments, the monitoring of treatment includes identifying exposure to a specific therapy. In some embodiments, the specific therapy is glucocorticoid administration therapy. In some embodiments, the specific therapy is dietary therapy. In some embodiments, the specific therapy is one that targets EoE molecules, or downstream genes affected by the same.

Embodiments of invention relate to methods of determining whether a subject has entered remission from EoE, the methods comprising applying a sample from the subject to a diagnostic panel that includes markers selected from Table 1, analyzing the results to obtain relatedness information relative to an EoE cohort, and making a determination as to the EoE status of the subject, wherein an analysis indicating grouping with an EoE cohort or a quantitative score similar to that of an EoE cohort are indicative of EoE remission in the subject.

Embodiments of invention relate to methods of determining the presence of inactive EoE relative to NL molecular pathology in a subject, the methods comprising applying a sample from the subject to a diagnostic panel that includes markers selected from Table 1, analyzing the results to obtain relatedness information relative to an EoE cohort; and making a determination as to the EoE status of the subject, wherein an analysis indicating grouping with an EoE cohort or a quantitative score similar to that of an EoE cohort are indicative of inactive EoE in the subject.

Embodiments of the invention also relate to methods of analyzing an archival sample obtained from a subject for indication of EoE in the subject, the methods comprising obtaining the archival sample, applying the sample to a diagnostic panel that includes markers selected from Table 1, analyzing the results to obtain relatedness information relative to an EoE cohort; and making a determination as to the EoE status of the subject, wherein an analysis indicating grouping with an EoE cohort or a quantitative score similar to that of an EoE cohort are indicative of EoE in the subject. In some embodiments, the archived sample is an FFPE sample.

Embodiments of the invention also relate to methods of developing or modifying a therapy for a subject in need thereof, the methods comprising applying a sample from the subject to a diagnostic panel that includes markers selected from Table 1, analyzing the results to obtain relatedness information relative to an EoE cohort, making a determination as to the pathological development of EoE in the subject, and developing or modifying a therapy for the subject based upon the determination, wherein an analysis indicating grouping with an EoE cohort or a quantitative score similar to that of an EoE cohort are indicative of EoE in the subject.

Embodiments of the invention also relate to methods of determining compliance with medical management and/or exposure to a specific therapy (e.g., PPI treatment, glucocorticoid administration, dietary therapy, and the like) in a subject undergoing treatment for EoE, the methods comprising applying a sample from the subject to a diagnostic panel that includes markers selected from Table 1, analyzing the results to obtain relatedness information relative to an EoE cohort, making a determination as to the molecular EoE profile of the subject, and determining compliance with medical management based upon the determination, wherein an analysis indicating grouping with an EoE cohort or a quantitative score similar to that of an EoE cohort are indicative of EoE in the subject.

Embodiments of the invention also relate to methods of determining tissue fibrosis and/or remodeling in a subject, including: applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the KRT23, COL1A2, or COL8A2 markers or genes relative to a normal cohort or an EoE cohort can be indicative of tissue fibrosis and/or remodeling.

Embodiments of the invention also relate to methods of treating a subject with tissue fibrosis and/or remodeling, including applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the KRT23, COL1A2, or COL8A2 markers or genes relative to a normal cohort or an EoE cohort can be indicative of tissue fibrosis and/or remodeling, and additionally including administering to the subject a therapy that targets at least one of the KRT23, COL1A2, and COL8A2 markers or genes.

Embodiments of the invention also relate to methods of determining abnormal mast cell function and/or mastocytosis in a subject, including: applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the TPSB2;TPSAB1, CPA3, and CMA1 markers or genes relative to a normal cohort or an EoE cohort can be indicative of abnormal mast cell production and/or mastocytosis.

Embodiments of the invention also relate to methods of treating a subject with abnormal mast cell production and/or mastocytosis, including applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the TPSB2;TPSAB1, CPA3, and CMA1 markers or genes relative to a normal cohort or an EoE cohort can be indicative of abnormal mast cell production and/or mastocytosis, and additionally including administering to the subject an anti-mast cell therapy. In some embodiments, the anti-mast cell therapy can be a therapy that targets at least one of the TPSB2;TPSAB1, CPA3, and CMA1 markers or genes.

Embodiments of the invention also relate to methods of determining abnormal natural killer (NK) cell production in a subject, including: applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the FCGR3B;FCGR3A, SLAMF7, and NCAM1 markers or genes relative to a normal cohort or an EoE cohort can be indicative of abnormal NK cell production.

Embodiments of the invention also relate to methods of treating a subject with abnormal NK cell production, including applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the FCGR3B;FCGR3A, SLAMF7, and NCAM1 markers or genes relative to a normal cohort or an EoE cohort can be indicative of abnormal NK cell production, and additionally including administering to the subject an anti-NK cell therapy. In some embodiments, the anti-NK cell therapy can be a therapy that targets at least one of the FCGR3B; FCGR3A, SLAMF7, and NCAM1 markers or genes.

Embodiments of the invention also relate to methods of determining abnormal T lymphocyte production in a subject, including: applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the IL4, IL5, and IL13 markers or genes relative to a normal cohort or an EoE cohort can be indicative of abnormal T lymphocyte production.

Embodiments of the invention also relate to methods of treating a subject with abnormal T lymphocyte production, including applying a sample from the subject to a diagnostic panel that includes at least one marker or gene selected from Table 1 to obtain a result; and analyzing the results to obtain relatedness information relative to a normal cohort or an EoE cohort, wherein elevated levels of at least one of the IL4, IL5, and IL13 markers or genes relative to a normal cohort or an EoE cohort can be indicative of abnormal T lymphocyte production, and additionally including administering to the subject an anti-T lymphocyte therapy. In some embodiments, the anti-T lymphocyte therapy can be a therapy that targets at least one of the IL4, IL5, and IL13 markers or genes.

Embodiments of the invention also relate to methods of determining abnormal production of a specific type of cell in a subject, including: applying a sample from the subject to a diagnostic panel that includes at least one marker or gene selected from Table 1 to obtain a result; and analyzing the results to obtain relatedness information relative to a normal cohort or an EoE cohort, wherein elevated levels of at least marker or gene associated with the specific cell type relative to a normal cohort or an EoE cohort can be indicative of abnormal production of the specific cell type.

Embodiments of the invention also relate to methods of treating a subject with abnormal production of a specific cell type, including applying a sample from the subject to a diagnostic panel that includes at least one marker or gene selected from Table 1 to obtain a result; and analyzing the results to obtain relatedness information relative to a normal cohort or an EoE cohort, wherein elevated levels of at least marker or gene associated with the specific cell type relative to a normal cohort or an EoE cohort can be indicative of abnormal production of the specific cell type, and additionally including administering to the subject a therapy targeting the specific cell type.

Embodiments of the invention also relate to an EoE molecular diagnostic panel including at least one marker or gene selected from Table 1. Embodiments of the invention also encompass an EoE molecular diagnostic panel including at least one marker or gene selected from Table 2. Embodiments of the invention also encompass an EoE molecular diagnostic panel including at least one marker or gene selected from Table 4. Embodiments of the invention also encompass an EoE molecular diagnostic panel including eotaxin-3 mRNA and at least one marker or gene selected from Table 1.

Embodiments of the invention also relate to a tissue pathology molecular diagnosis panel including at least one marker or gene selected from Table 1. In some embodiments, the tissue pathology molecular diagnosis panel includes at least one marker or gene selected from KRT23, COL1A2, COL8A2, TPSB2;TPSAB1, CPA3, CMA1, FCGR3B;FCGR3A, SLAMF7, and NCAM1. In some embodiments, the tissue pathology molecular diagnosis panel can include all of the KRT23, COL1A2, COL8A2, TPSB2;TPSAB1, CPA3, CMA1, FCGR3B;FCGR3A, SLAMF7, and NCAM1 markers or genes.

FIG. 1 illustrates an exemplary embodiment of the invention. The method disclosed herein can include three steps, which can be finished within 1 working day (6-8 hours with multiple sample capacity). As graphically summarized panel A, RNA extraction can be performed on a patient esophageal biopsy sample. After RNA quantity/quality measurement, RNA from the sample is subjected to reverse transcription (RT) reaction. Next, cDNA corresponding to the reverse-transcribed RNA is mixed with a qPCR cocktail and loaded onto a 384 well fluidic card (for analysis of up to 4 patients per 384 well card with analysis of 96 housekeeping genes per patient, including 94 representative EoE genes and 2 housekeeping genes). The cDNA is then amplified with a real-time qPCR system. The analysis step can be performed in qPCR analysis software, and the qPCR data is subjected to at least one of two algorithms as disclosed herein to establish an EoE diagnosis. The EoE diagnosis can serve as a basis for a final diagnostic report as well as in assisting selection or modification of an appropriate therapy for the patient.

In some embodiments, the EDP markers or genes are measured using a fluidic card loaded with the 96 EDP genes. In some embodiments, the 94 representative EoE genes or a subset of these genes are measured using other methods and/or tools, including for example, but not limited to, NANODROP® technology, and the like. The person of skill in the art will recognize such other formats and tools, which can be commercially available or which can be developed specifically for such analysis.

Embodiments of the invention involve analysis of the result from applying a sample from the subject to a diagnostic panel that comprises at least one marker or gene selected from Table 1 to obtain a result, analyzing the results to obtain relatedness information relative to an EoE cohort and making a determination as to the EoE status of the subject, wherein an analysis indicating grouping with an EoE cohort or a quantitative score similar to that of an EoE cohort are indicative of EoE in the subject. In some embodiments, relatedness information is obtained by at least one algorithm selected from the group of: a cluster analysis algorithm, a cumulative quantification algorithm, and any combination thereof. In some embodiments, a cluster analysis indicating grouping with an EoE cohort and/or a quantitative score based upon mean±about 3SDs for an EoE cohort are indicative of EoE in the subject. In some embodiments, other types of algorithms are used to obtain relatedness information. In some embodiments, relatedness information is obtained by a lookup table. User of any type of determination of relatedness information to analyze results of subjecting a sample from a subject to a diagnostic panel that comprises at least one marker or gene selected from Table 1 is covered by the scope of the invention.

The EoE Diagnostic Panel

In embodiments of the invention, the eosinophilic esophagitis diagnostic panel (EDP) contains markers or genes selected from the representative EoE genes listed in Table 1.

In some embodiments the eosinophilic esophagitis diagnostic panel contains at least one marker or gene selected from Table 1. In some embodiments the eosinophilic esophagitis diagnostic panel contains at least 10 markers or genes selected from Table 1. In some embodiments, the eosinophilic esophagitis diagnostic panel contains at least 20 markers or genes selected from Table 1. In some embodiments, the eosinophilic esophagitis diagnostic panel contains at least 30 markers or genes selected from Table 1. In some embodiments, the eosinophilic esophagitis diagnostic panel contains at least 40 markers or genes selected from Table 1. In some embodiments, the eosinophilic esophagitis diagnostic panel contains at least 50 markers or genes selected from Table 1. In some embodiments, the eosinophilic esophagitis diagnostic panel contains at least 60 markers or genes selected from Table 1. In some embodiments, the eosinophilic esophagitis diagnostic panel contains at least 70 markers or genes selected from Table 1. In some embodiments, the eosinophilic esophagitis diagnostic panel contains at least 80 markers or genes selected from Table 1. In some embodiments, the eosinophilic esophagitis diagnostic panel contains at least 90 markers or genes selected from Table 1.

In some embodiments of the invention, the eosinophilic esophagitis diagnostic panel contains 1, 2, 3, 4, 5, 6, 7, 8, or 9 markers or genes selected from Table 1. In some embodiments of the invention, the eosinophilic esophagitis diagnostic panel contains 10, 11, 12, 13, 14, 15, 16, 17, 18, or 19 markers or genes selected from Table 1. In some embodiments of the invention, the eosinophilic esophagitis diagnostic panel contains 20, 21, 22, 23, 24, 25, 26, 27, 28, or 29 markers or genes selected from Table 1. In some embodiments of the invention, the eosinophilic esophagitis diagnostic panel contains 30, 31, 32, 33, 34, 35, 36, 37, 38, or 39 markers or genes selected from Table 1. In some embodiments of the invention, the eosinophilic esophagitis diagnostic panel contains 40, 41, 42, 43, 44, 45, 46, 47, 48, or 49 markers or genes selected from Table 1. In some embodiments of the invention, the eosinophilic esophagitis diagnostic panel contains 50, 51, 52, 53, 54, 55, 56, 57, 58, or 59 markers or genes selected from Table 1. In some embodiments of the invention, the eosinophilic esophagitis diagnostic panel contains 60, 61, 62, 63, 64, 65, 66, 67, 68, or 69 markers or genes selected from Table 1. In some embodiments of the invention, the eosinophilic esophagitis diagnostic panel contains 70, 71, 72, 73, 74, 75, 76, 77, 78, or 79 markers or genes selected from Table 1. In some embodiments of the invention, the eosinophilic esophagitis diagnostic panel contains 80, 81, 82, 83, 84, 85, 86, 87, 88, or 89 markers or genes selected from Table 1. In some embodiments of the invention, the eosinophilic esophagitis diagnostic panel contains 90, 91, 92, 93, 94, 95, or 96 markers or genes selected from Table 1.

In some embodiments, the eosinophilic esophagitis diagnostic panel contains anywhere between 1 to 32 markers or genes selected from Table 1 or Table 4. In some embodiments, the eosinophilic esophagitis diagnostic panel contains anywhere between 1 to 77 markers or genes selected from Table 1 or Table 2.

In some embodiments, the eosinophilic esophagitis diagnostic panel contains the markers or genes listed in Table 2. In some embodiments, the eosinophilic esophagitis diagnostic panel contains the markers or genes listed in Table 4.

The Tissue Pathology Diagnostic Panel

In embodiments of the invention, the tissue pathology diagnostic panel contains markers or genes selected from the genes listed in Table 1.

In some embodiments, the tissue pathology diagnostic panel includes at least one marker or gene selected from KRT23, COL1A2, COL8A2, TPSB2;TPSAB1, CPA3, CMA1, FCGR3B;FCGR3A, SLAMF7, and NCAM1. In some embodiments, the tissue pathology diagnostic panel can include all of the KRT23, COL1A2, COL8A2, TPSB2; TPSAB1, CPA3, CMA1, FCGR3B;FCGR3A, SLAMF7, and NCAM1 markers or genes.

In some embodiments the tissue pathology diagnostic panel contains at least one marker or gene selected from Table 1. In some embodiments the tissue pathology diagnostic panel contains at least 10 markers or genes selected from Table 1. In some embodiments, the tissue pathology diagnostic panel contains at least 20 markers or genes selected from Table 1. In some embodiments, the tissue pathology diagnostic panel contains at least 30 markers or genes selected from Table 1. In some embodiments, the tissue pathology diagnostic panel contains at least 40 markers or genes selected from Table 1. In some embodiments, the tissue pathology diagnostic panel contains at least 50 markers or genes selected from Table 1. In some embodiments, the tissue pathology diagnostic panel contains at least 60 markers or genes selected from Table 1. In some embodiments, the tissue pathology diagnostic panel contains at least 70 markers or genes selected from Table 1. In some embodiments, the tissue pathology diagnostic panel contains at least 80 markers or genes selected from Table 1. In some embodiments, the tissue pathology diagnostic panel contains at least 90 markers or genes selected from Table 1.

In some embodiments of the invention, the tissue pathology diagnostic panel contains 1, 2, 3, 4, 5, 6, 7, 8, or 9 markers or genes selected from Table 1. In some embodiments of the invention, the tissue pathology diagnostic panel contains 10, 11, 12, 13, 14, 15, 16, 17, 18, or 19 markers or genes selected from Table 1. In some embodiments of the invention, the tissue pathology diagnostic panel contains 20, 21, 22, 23, 24, 25, 26, 27, 28, or 29 markers or genes selected from Table 1. In some embodiments of the invention, the tissue pathology diagnostic panel contains 30, 31, 32, 33, 34, 35, 36, 37, 38, or 39 markers or genes selected from Table 1. In some embodiments of the invention, the tissue pathology diagnostic panel contains 40, 41, 42, 43, 44, 45, 46, 47, 48, or 49 markers or genes selected from Table 1. In some embodiments of the invention, the tissue pathology diagnostic panel contains 50, 51, 52, 53, 54, 55, 56, 57, 58, or 59 markers or genes selected from Table 1. In some embodiments of the invention, the tissue pathology diagnostic panel contains 60, 61, 62, 63, 64, 65, 66, 67, 68, or 69 markers or genes selected from Table 1. In some embodiments of the invention, the tissue pathology diagnostic panel contains 70, 71, 72, 73, 74, 75, 76, 77, 78, or 79 markers or genes selected from Table 1. In some embodiments of the invention, the tissue pathology diagnostic panel contains 80, 81, 82, 83, 84, 85, 86, 87, 88, or 89 markers or genes selected from Table 1. In some embodiments of the invention, the tissue pathology diagnostic panel contains 90, 91, 92, 93, 94, 95, or 96 markers or genes selected from Table 1.

Dual Clustering and Dimensionality Reduction Algorithm

A distance metric calculation was also performed for clustering and dimensionality reduction (>=2-D) of EoE patterns. In this analysis, when sample similarity/dissimilarity are compared, there are two distance metrics employed, namely Pearson-centered and Euclid-centered distances, for heatmap dendrogram assembling and multidimensional scaling (MDS) positioning, respectively. The dual algorithm resulted in nearly identical diagnostic merit, indicating that both are validated and ready for clinical practice in the near future, in either fresh tissue RNA or FFPE formats.

The formulae in the context of qPCR gene expression in n dimensional space are given below. For any given pair of two samples A and B assayed with normalized Ct values on an expression array of n entities/genes are found to be significantly differentially expressed between two cohorts, the n-dimensional EDP array data is represented as {Ai,Bi} (i=1, 2, 3, . . . n). Sample gene expression pattern similarity is compared, and results are illustrated by a hierarchical tree. The Pearson correlation distance between any given pair of samples is calculated based upon formula (1) below, and the Euclid-centered distance is calculated based upon formula (2) below.

$$\text{Pearson } r = \frac{\sum_{i=1}^{n}(Ai - \overline{A})(Bi - \overline{B})}{\sqrt{\sum_{i=1}^{n}(Ai - \overline{A})^2}\sqrt{\sum_{i=1}^{n}(Bi - \overline{B})^2}} \quad (1)$$

$$\text{Euclid distance} = \sqrt{\sum_{i=1}^{n}(Ai - Bi)^2} \quad (2)$$

In some embodiments, n can be any number from 1 to 96 based on the number of representative genes that are found to be significantly differentially expressed between a healthy cohort and a disease state cohort. In some embodiments, n is 1, 2, 3, 4, 5, 6, 7, 8, or 9. In some embodiments, n is 10, 11, 12, 13, 14, 15, 16, 17, 18, or 19. In some embodiments, n is 20, 21, 22, 23, 24, 25, 26, 27, 28, or 29. In some embodiments, n is 30, 31, 32, 33, 34, 35, 36, 37, 38, or 39. In some embodiments, n is 40, 41, 42, 43, 44, 45, 46, 47, 48, or 49. In some embodiments, n is 50, 51, 52, 53, 54, 55, 56, 57, 58, or 59. In some embodiments, n is 60, 61, 62, 63, 64, 65, 66, 67, 68, or 69. In some embodiments, n is 70, 71, 72, 73, 74, 75, 76, 77, 78, or 79. In some embodiments, n is 80, 81, 82, 83, 84, 85, 86, 87, 88, or 89. In some embodiments, n is 90, 91, 92, 93, 94, 95, or 96.

In some embodiments, n is 32. In some embodiments, n is 33. In some embodiments, n is 77. In some embodiments, n is 94. In some embodiments, n is 96.

The Quantitative Scoring Algorithm

The EoE scoring algorithm for detecting EoE patterns is based upon cumulative quantification of Ct. value (i.e. absolute amount of gene product). The advantage of the "one-dimensional" EoE score lies in that this compressed quantification still represents the bi-directional gene dysregulation in digit format without much loss of expression information, rendering comprehension and comparison more user-friendly. The EoE score is given by formula (3) below:

$$\text{EoE Score} = \Sigma \Delta CT = \Sigma(\text{Ct. down genes} - \text{Ct. GAPDH}) - \Sigma(\text{Ct. up genes} - \text{Ct. GAPDH}) \quad (3)$$

The threshold for the disease state can be defined as mean±m standard deviations (SDs) relative to the normal cohort group. In some embodiments, m is 1. In some embodiments, m is 2. In some embodiments, m is 3. In some embodiments, m is 4. In some embodiments, m is 5, or more. In some embodiments, m is 1 to 2. In some embodiments, m is 2 to 3. In some embodiments, m is 3 to 4. In some embodiments, m is 1.25, 1.5, or 1.75. In some embodiments, m is 2.25, 2.5, or 2.75. In some embodiments, m is 3.25, 3.5, or 3.75. In some embodiments, m is 4.25, 4.5, or 4.75.

The threshold for the disease state can alternatively be defined as a 1-D quantitative score, or diagnostic cutoff, based upon receiver operating characteristic (ROC) analysis. The EoE score, and hence the diagnostic cutoff, varies with the selection of genes considered in the equation.

The quantitative score based upon ROC analysis can be used to determine the specificity and/or the sensitivity of a given diagnostic cutoff. In some embodiments, the quantitative score based upon ROC analysis is one that provides an EoE diagnosis with greater than 90% specificity and greater than 90% specificity. In some embodiments, the quantitative score based upon ROC analysis is one that provides an EoE diagnosis with greater than 90% specificity or greater than 90% specificity.

In some embodiments, the quantitative score based upon ROC analysis is one that provides an EoE diagnosis with greater than 80%, 81%, 82%, 83%, 84%, 85%, 86%, 87%, 88%, or 89% specificity. In some embodiments, the quantitative score based upon ROC analysis is one that provides an EoE diagnosis with greater than 90%, 91%, 92%, 93%, 94%, 95%, 96%, 97%, 98%, or 99% specificity.

In some embodiments, the quantitative score based upon ROC analysis is one that provides an EoE diagnosis with greater than 80%, 81%, 82%, 83%, 84%, 85%, 86%, 87%, 88%, or 89% sensitivity. In some embodiments, the quantitative score based upon ROC analysis is one that provides an EoE diagnosis with greater than 90%, 91%, 92%, 93%, 94%, 95%, 96%, 97%, 98%, or 99% sensitivity.

In some embodiments, the quantitative score based upon ROC analysis is one that provides an EoE diagnosis with greater than 85% specificity and greater than 85% specificity. In some embodiments, the quantitative score based upon ROC analysis is one that provides an EoE diagnosis with greater than 86% specificity and greater than 86% specificity. In some embodiments, the quantitative score based upon ROC analysis is one that provides an EoE diagnosis with greater than 87% specificity and greater than 87% specificity. In some embodiments, the quantitative score based upon ROC analysis is one that provides an EoE diagnosis with greater than 88% specificity and greater than 88% specificity. In some embodiments, the quantitative score based upon ROC analysis is one that provides an EoE diagnosis with greater than 89% specificity and greater than 89% specificity.

In an exemplary embodiment, the 77 genes of Table 2 are evaluated, and the quantitative score based upon ROC analysis is one that provides an EoE diagnosis with greater than 90% specificity and greater than 90% specificity, providing a diagnostic cutoff of 333. In some embodiments, the 77 genes of Table 2 are evaluated, and the diagnostic cutoff is greater than 278. In some embodiments, the 77 genes of Table 2 are evaluated, and the diagnostic cutoff is less than 371. In some embodiments, the 77 genes of Table 2 are evaluated, and the diagnostic cutoff is between 278 and 371. In some embodiments, the 77 genes of Table 2 are evaluated, and the diagnostic cutoff is between 304 and 361. In some embodiments, the 77 genes of Table 2 are evaluated, and the diagnostic cutoff is between 316 and 350. In some embodiments, the 77 genes of Table 2 are evaluated, and the diagnostic cutoff is between 325 and 348.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Patient Selection and Bioinformatics

All patient samples were acquired from an eosinophil-associated gastrointestinal disorders (EGID) biobank located at Cincinnati Children's Hospital Medical Center (CCHMC). For algorithm developing cohorts, normal (NL) patients were defined as those with eosinophils/HPF <2, who were not on swallowed or systemic treatment. Eosinophilic esophagitis (EoE) patients were defined as those with eosinophils/HPF >15, who were not on swallowed or systemic treatment. EoE remission patients were selected based on a complete histological eosinophilia remission defined as those with eosinophils/HPF <2 after a topical fluticasone propionate (swallowed FLOVENT®) or budesonide treatment. The selection criteria were based on the peak eosinophil count in distal esophageal biopsies, and a solid histological diagnosis was established for these patients studied. All patients tested were pediatric patients less than 21 years old, with the exception of the adult transcriptome assay, which recruited 12 adults over 22 years old.

Bioinformatic selection of EoE genes for a diagnostic panel was performed based on a set of mRNA microarray results (basis from Blanchard et al. *J Clin Invest* 116:536-47 (2006)), with a larger sample pool size and the factor of topical steroid response included. After a comprehensive expression profile analysis by Genespring GX 11.5 software (Agilent Technologies), a selection of 94 EoE-representative genes was performed based on the following considerations: dysregulation (based on p-value and fold-change), bidirectional dysregulation coverage capacity to predict steroid exposure (glucocorticoid-responsive genes), capacity to differentiate EoE remission from NL (genes not fully reversible by steroid treatment), and fibrosis regulators. In addition, since some of the cytokine producing cells are too scarce to be detected by the microarray but can play an important role in EoE pathogenesis, biomarkers for several immunocytes that are known to affect EoE allergic responses were also included in the panel (Table 1).

Example 2

RNA Extraction and Reverse Transcription

Biopsy mRNA/miRNA extraction was carried out by the miRNeasy RNA extraction kit (Qiagen, 217504) for incoming clinical biopsy samples on a daily basis, archived in the −80° C. EGID research sample library, and registered in the electronic EGID database. Aliquots corresponding to 500 ng of RNA were acquired from the clinical biopsy samples stored at −80° C. in the EGID biobank. The RNA was thawed on ice and reverse-transcribed to cDNA stock by the iScript cDNA Synthesis Kit (BioRad 170-8891), following the manufacturer's protocol. Briefly, 500 ng of RNA was mixed with the reaction mix and reverse transcription (RT) enzyme in a total volume of 20 μl, incubated at 25° C. for 5 min, 42° C. for 30 min, 85° C. for 5 min, and then kept at 4° C. and later −20° C. for storage.

For formalin-fixed, paraffin-embedded (FFPE) samples, from each paraffin block, eight 10-μm sections were cut continuously and then immediately subjected to RNA extraction with the miRNeasy mini kit (Qiagen, 217504), following the manufacturer's protocol. Representative RNA spectrometry analyses indicated that the RNA quality was sufficient for qPCR reaction (typically 260/280 >1.8). Other steps were subsequently the same as the analysis of fresh samples described above.

Example 3

QPCR Amplification with 384-Well Fluidic Card

One of the breakthroughs in understanding EoE pathogenesis was the discovery of the whole genome mRNA esophageal expression profile ("EoE transcriptome," Blanchard et al. 2006. supra). The "EoE transcriptome" consists of approximately 500 EoE genes, the involvement of which uncovered key pathogenic steps, such as the role of eotaxin-3 in eosinophil recruitment, the importance of periostin in facilitating eosinophil recruitment and tissue remodeling (Zuo et al. *J. Immunol.* 185:660-9 (2010); Blanchard et al. *Mucosal. Immunol.* 1:289-96 (2008)), the presence and role of mast cells (Abonia et al. *J. Allergy Clin. Immunol.* 126:140-9 (2010)), T cells (Fuentebella et al. *J. Pediatr. Gastroenterol. Nutr.* 51:283-9 (2010); Mulder et al. *Mucosal. Immunol.* 4:139-47 (2011)), and the locally found cytokines (Blanchard et al. *J. Allergy Clin. Immunol.* 127: 208-17 (2011)) in disease pathogenesis, and evidence for an impaired local barrier function.

The transcriptome data clearly demonstrated that EoE exhibits a distinct gene expression profile from chronic esophagitis and GERD with little overlap, despite the shared esophageal eosinophilia. For example, expression levels of esophageal eotaxin-3 in one biopsy can identify the presence of EoE with remarkable sensitivity of 89% of the time, thus differentiating EoE from GERD (Blanchard et al. 2011. *J Allergy Clin Immunol* 127(1): 208-217, 217 e1-7, which is incorporated herein by reference in its entirety). Although the mRNA microarray can be used to provide a differential diagnosis of EoE, this method is not optimal in clinical applications for diagnostic purposes due to the pronounced transcriptional difference between EoE and GERD, the long turn-around time, the technical complexity of the mRNA microarray, and the associated high cost of the assay.

Accordingly, in order to utilize the diagnostic strength from the microarray expression profile analysis and reduce commercial barriers (e.g. turn-around time and running costs), an EoE molecular Diagnosis Panel (EDP) built on a Taqman qPCR-based low density microarray system was developed. The EDP contains a selection of 96 highly representative EoE genes/biomarkers pre-embedded on a 384 well fluidic card with the ABI 7900HT amplification system for use as disclosed herein. The EDP can be used alone or can be enhanced by combination with determination of eotaxin-3 expression levels.

The Taqman primers/probes for a selection of 94 representative dysregulated EoE genes plus two housekeeping controls (GAPDH, 18S rRNA) were customized to be pre-embedded onto a 384-well fluidic card in 96a format (Applied Biosystems), therefore having up to a 4-patient capacity at 96 genes per patient (FIG. 1). Table 1 contains the list of 96 genes used for the array. Taqman real-time PCR amplification was performed on an ABI 7900HT system (Applied Biosystems) with appropriate heating block. For each patient sample (fresh or FFPE), 25 µl of cDNA aliquot corresponding to 125-500 ng of starting RNA-equivalent cDNA was adjusted to 100 µl with nuclease-free $H_2O$ and mixed with 100 µl of TaqMan Universal PCR Master Mix II No. UNG (4440040, Applied Biosystems) and loaded onto the fluidic card by centrifugation following standard fluidic card procedures in order to amplify the 96 genes. The standard fluidic card amplification protocol consisted of a ramp at 50° C. for 2 minutes, followed by a hot start of 95° C. for 10 min, followed by 40 cycles of 30 seconds at 97° C. and 1 minute at 59.7° C. After the qPCR was completed, raw Ct. values for each sample/each gene were exported into Genespring GX 11.5 (Agilent Technologies) for algorithm development by statistical and bioinformatics analysis to provide diagnostic information.

FIG. 1. The EDP standard operating procedures consist of 3 major steps, namely RNA extraction, EDP panel qPCR, and data analysis, which can be finished within 1 working day (6-8 hours with multiple sample capacity). RNA is extracted from a fresh patient esophageal biopsy or FFPE tissue section, followed by RNA quantity/quality assessment by NanoDrop (Thermo Scientific). An aliquot of the RNA sample (500 ng) is subjected to reverse transcription (RT) reaction, and the resulting cDNA is mixed with a Taqman Master Mix and loaded onto the 384 well fluidic card (96A format: 4 patients per 384 well card with 96 genes per patient) for amplification with the ABI 7900HT real-time qPCR system (Applied Biosystems). The expression analysis is performed in Genespring GX11 software (Agilent), and the raw qPCR data is subjected to dual algorithms, namely signature analysis (heatmap clustering) and dimensionality reduction (EoE score) to establish molecular EoE diagnosis, which forms the basis for the final diagnostic report. The molecular diagnosis report is designed to provide diagnosis and appropriate therapy decision making and prognosis.

Table 1 lists the representative EoE genes that were defined as the diagnostic panel. This unique and highly representative panel was selected based on the microarray results by bioinformatics means (Example 1), serving a diagnostic purpose as indicated in the table. The magnitude of dysregulation vs. NL group is shown in the format of fold change, with positive and negative numbers indicating up- and down-regulation, respectively.

TABLE 1

List of 96 genes on the EDP

| Gene Symbol | Fold change (EoE vs. NL) | AB AssayID | Purpose | SEQ ID NO. |
| --- | --- | --- | --- | --- |
| TNFAIP6 | 414.9697 | Hs01113602_m1 | EoE diagnosis | 1 |
| ALOX15 | 293.0993 | Hs00609608_m1 | EoE diagnosis | 2 |
| NEFL | 79.928955 | Hs00196245_m1 | EoE diagnosis | 3 |
| PMCH | 69.93395 | Hs00173595_m1 | EoE diagnosis | 4 |
| CXCL1 | 65.62399 | Hs00236937_m1 | EoE diagnosis | 5 |
| NEFM | 56.782463 | Hs00193572_m1 | EoE diagnosis | 6-7 |
| APOBEC3A | 46.007984 | Hs00377444_m1 | EoE diagnosis | 8-9 |
| POSTN | 31.321604 | Hs00170815_m1 | EoE diagnosis | 10-13 |
| IL8 | 27.459871 | Hs01553824_g1 | EoE diagnosis | 14 |
| ANO1 | 26.078642 | Hs00216121_m1 | EoE diagnosis | 15-16 |
| SLC26A4 | 23.281775 | Hs01070620_m1 | EoE diagnosis | 17 |
| SUSD2 | 20.296898 | Hs00219684_m1 | EoE diagnosis | 18 |
| CPA3 | 14.141504 | Hs00157019_m1 | EoE diagnosis, mast cell marker | 19 |
| IGJ | 13.747173 | Hs00950678_g1 | EoE diagnosis | 20 |
| CXCL6 | 12.157768 | Hs00237017_m1 | EoE diagnosis | 21 |
| PHLDB2 | 11.460421 | Hs00377503_m1 | EoE diagnosis | 22-23 |
| HPGDS | 8.6371 | Hs00183950_m1 | EoE diagnosis | 24 |
| UBD | 8.064061 | Hs00197374_m1 | EoE diagnosis | 25 |
| SAMSN1 | 7.4895926 | Hs00223275_m1 | EoE diagnosis | 26 |
| RTP4 | 5.130961 | Hs00223342_m1 | EoE diagnosis | 27 |
| KCNJ2 | 4.9398546 | Hs01876357_s1 | EoE diagnosis | 28 |
| MMP12 | 3.9932182 | Hs00899668_m1 | EoE diagnosis | 29 |
| UPK1B | 3.3796203 | Hs00199583_m1 | EoE diagnosis | 30 |
| GRK5 | 2.860464 | Hs00992173_m1 | EoE diagnosis | 31 |
| SYNPO2 | −2.015054 | Hs02786674_s1 | EoE diagnosis | 32-34 |
| ACPP | −2.4676523 | Hs00173475_m1 | EoE diagnosis | 35-36 |
| CITED2 | −3.0311375 | Hs01897804_s1 | EoE diagnosis | 37-39 |
| CTNNAL1 | −5.1087794 | Hs00972098_m1 | EoE diagnosis | 40 |
| MSRB3 | −5.2393684 | Hs00827017_m1 | EoE diagnosis | 41-44 |
| FLG | −6.70856 | Hs00863478_g1 | EoE diagnosis | 45 |
| SPINK7 | −7.1268573 | Hs00261445_m1 | EoE diagnosis | 46 |
| TSPAN12 | −7.2738805 | Hs01113125_m1 | EoE diagnosis | 47 |
| ALOX12 | −9.068814 | Hs00167524_m1 | EoE diagnosis | 48 |
| PNLIPRP3 | −9.584329 | Hs00406604_m1 | EoE diagnosis | 49 |
| MT1M | −9.983593 | Hs00828387_g1 | EoE diagnosis | 50 |
| UPK1A | −10.927818 | Hs01086736_m1 | EoE diagnosis | 51 |
| ENDOU | −11.909287 | Hs00195731_m1 | EoE diagnosis | 52 |
| EML1 | −13.01767 | Hs00270014_m1 | EoE diagnosis | 53-54 |
| IGFL1 | −14.203143 | Hs01651089_g1 | EoE diagnosis | 55 |
| ARG1 | −14.377323 | Hs00968979_m1 | EoE diagnosis | 56 |
| CRISP2 | −14.585883 | Hs00162960_m1 | EoE diagnosis | 57-61 |
| ACTG2 | −15.12598 | Hs01123712_m1 | EoE diagnosis | 62-63 |
| CDA | −24.242752 | Hs00156401_m1 | EoE diagnosis | 64 |
| CLDN10 | −30.316372 | Hs01075312_m1 | EoE diagnosis | 65-67 |
| CRYM | −34.084908 | Hs00157121_m1 | EoE diagnosis | 68-69 |
| DSG1 | −69.92507 | Hs00355084_m1 | EoE diagnosis | 70 |
| CCL26 | 107.07061 | Hs00171146_m1 | EoE diagnosis, DDX | 71 |

TABLE 1-continued

List of 96 genes on the EDP

| Gene Symbol | Fold change (EoE vs. NL) | AB AssayID | Purpose | SEQ ID NO. |
|---|---|---|---|---|
| LRRC31 | 59.492077 | Hs00226845_m1 | EoE diagnosis, DDX | 72 |
| GLDC | 34.990837 | Hs01580586_g1 | EoE diagnosis, DDX | 73 |
| CD200R1 | 31.68025 | Hs00708558_s1 | EoE diagnosis, DDX | 74-75 |
| CDH26 | 20.827156 | Hs00375371_m1 | EoE diagnosis, DDX | 76-77 |
| EPPK1 | 15.982675 | Hs02379935_s1 | EoE diagnosis, DDX | 78 |
| RUNX2 | 9.24365 | Hs00298328_s1 | EoE diagnosis, DDX | 79-81 |
| HRH1 | 8.50056 | Hs00911670_s1 | EoE diagnosis, DDX | 82-85 |
| CTSC | 7.199942 | Hs00175188_m1 | EoE diagnosis, DDX | 86-88 |
| CA2 | 7.1597824 | Hs00163869_m1 | EoE diagnosis, DDX | 89 |
| CFI | 5.1003084 | Hs00989715_m1 | EoE diagnosis, DDX | 90 |
| GPR160 | 4.8567142 | Hs01878570_s1 | EoE diagnosis, DDX | 91 |
| MUC4 | 4.773386 | Hs00366414_m1 | EoE diagnosis, DDX | 92-94 |
| CFB; C2 | 4.424164 | Hs00156060_m1 | EoE diagnosis, DDX | 95 |
| CHL1 | 2.663009 | Hs00544069_m1 | EoE diagnosis, DDX | 96 |
| GCNT3 | 2.298165 | Hs00191070_m1 | EoE diagnosis, DDX | 97 |
| SLC16A6 | -2.5263813 | Hs00190779_m1 | EoE diagnosis, DDX | 98-99 |
| GRPEL2 | -3.237536 | Hs00537120_s1 | EoE diagnosis, DDX | 100 |
| ZNF365 | -10.4442835 | Hs00209000_m1 | EoE diagnosis, DDX | 101 |
| C7orf68 | -11.64081 | Hs00203383_m1 | EoE diagnosis, DDX | 102 |
| GYS2 | -17.05968 | Hs00608677_m1 | EoE diagnosis, DDX | 102 |
| CRISP3 | -55.189964 | Hs00195988_m1 | EoE diagnosis, DDX | 104-105 |
| EPB41L3 | 2.3694193 | Hs00202360_m1 | DDX | 106 |
| TRIM2 | 1.9073116 | Hs00209620_m1 | DDX | 107 |
| PTGFRN | 1.7017435 | Hs01385989_m1 | DDX | 108 |
| SYNPO2L | -1.4880642 | Hs00227561_m1 | DDX | 109 |
| CDH20 | -2.2144973 | Hs00230412_m1 | DDX | 110 |
| IL5RA | 3.0407522 | Hs00236871_m1 | EoE diagnosis, EOS maker | 111-112 |
| CLC | 15.6791 | Hs00171342_m1 | EoE diagnosis, EOS marker | 113 |
| CCR3 | 4.2005568 | Hs99999027_s1 | EoE diagnosis, EOS marker | 114-117 |
| TSLP | -1.1459398 | Hs00263639_m1 | EoE diagnosis, epithelial drive monitor | 118-119 |
| COL8A2 | 7.968154 | Hs00697025_m1 | EoE diagnosis, fibrosis marker | 120 |
| KRT23 | 3.3364804 | Hs00210096_m1 | EoE diagnosis, fibrosis marker | 121 |
| IL32 | 1.725982 | Hs00992441_m1 | EoE diagnosis, IL-8 inducer | 122-129 |
| TPSB2; TPSAB1 | 7.7080927 | Hs02576518_gH | EoE diagnosis, mast cell marker | 130 |
| CMA1 | 4.8942575 | Hs00156558_m1 | EoE diagnosis, mast cell marker | 131 |
| FCGR3B; FCGR3A | 4.515885 | Hs00275547_m1 | EoE diagnosis, NK marker | 132-136 |
| IL13 | 17.897106 | Hs01124272_g1 | EoE diagnosis, TH2 marker | 137 |
| IL5 | 5.1750216 | Hs00174200_m1 | EoE diagnosis, TH2 marker, DDX | 138 |
| IL4 | 1.9009488 | Hs99999030_m1 | TH2 marker, DDX | 139-140 |
| EPX | 1.5585572 | Hs00166795_m1 | EOS marker | 141 |
| COL1A2 | -1.5572102 | Hs01028971_m1 | Fibrosis marker | 142 |
| CCL8 | 1.5585572 | Hs00271615_m1 | Allergic chemokine marker | 143 |
| SLAMF7 | -1.0235873 | Hs00900280_m1 | NK marker | 144 |
| NCAM1 | 1.5785906 | Hs00287831_s1 | NK marker, DDX | 145-147 |
| H19 | 1.2154144 | Hs00262142_g1 | Steroid prediction | 148 |
| F3 | 1.1785437 | Hs01076032_m1 | Steroid prediction, DDX | 149 |
| FKBP5 | -1.0142508 | Hs00296750_s1 | Steroid prediction, DDX | 150-152 |
| GAPDH | 1 | Hs03929097_g1 | Primary housekeeping gene | 153 |
| 18S | 1.1119206 | Hs99999901_s1 | Auxiliary housekeeping gene | 154 |

Positive fold change values indicate up-regulation; negative fold change values indicate down-regulation.
EoE diagnosis = differential diagnosis between active EoE and NL.
DDX = differential diagnosis for distinction between EoE, EoE remission, and NL.

Example 4

QPCR Data Analysis

The raw amplification data was group acquired/analyzed by RQ manager 2.0 (Applied Biosystems), then exported into Genespring GX 11.5 for further relative expression analysis and algorithm development. A false discovery rate (FDR)-corrected two-tailed student T-test (corrected $p<0.05$) was performed between the 14 normal (NL) and 15 EoE algorithm-developing cohorts simultaneously with a 2-fold change filter, which resulted in the identification of 77 genes that are significantly dysregulated bi-directionally out of the 94 genes of the diagnostic panel. These 77 genes provided the foundation for the dual algorithm development.

For the cluster analysis algorithm, the gene of interest (GOI) Ct. values were first normalized to GAPDH Ct. and then normalized to the median of all samples for each given gene. In Genespring software, cluster analysis was performed by a hierarchical clustering design algorithm, with the Pearson-centered distance metric and centroid linkage rule. Both condition and gene entity were 2-D clustered in conjunction with an expression heat map.

For the $\Sigma\Delta CT$ algorithm, a dimensionality reduction formula was used to address the bi-directional signature in 1-D space (i.e. a number). The expression Ct. value of the housekeeping gene GAPDH was first subtracted from each EoE GOI Ct. value to acquire the $\Delta CT$. The sums of the $\Delta CT$ were taken respectively for up-regulated and down-regulated gene groups. Considering the direction of the dysregulation, a negative weight was endowed to the up-gene sum before the addition of the two $\Sigma\Delta CT$ values to establish the "EoE Score" to reflect the gene signature and disease severity.

$$\text{EoE Score} = \Sigma\Delta CT = \Sigma(\text{Ct. down genes} - \text{Ct. GAPDH}) - \Sigma(\text{Ct. up genes} - \text{Ct. GAPDH}) \quad (3)$$

TABLE 2

Selection of 77 EoE genes identified as being significantly dysregulated

| GeneSymbol | AB AssayID | Regulation |
|---|---|---|
| ACPP | Hs01113602_m1 | down |
| ACTG2 | Hs00609608_m1 | down |
| ALOX12 | Hs00171146_m1 | down |
| ALOX15 | Hs00196245_m1 | up |
| ANO1 | Hs00173595_m1 | up |
| APOBEC3A | Hs00236937_m1 | up |
| ARG1 | Hs00226845_m1 | down |
| C7orf68 | Hs00193572_m1 | down |
| CA2 | Hs00377444_m1 | up |
| CCL26 | Hs01580586_g1 | up |
| CCR3 | Hs00708558_s1 | up |
| CD200R1 | Hs00170815_m1 | up |
| CDA | Hs01553824_g1 | down |
| CDH20 | Hs00230412_m1 | down |
| CDH26 | Hs00216121_m1 | up |
| CFB; C2 | Hs01070620_m1 | up |
| CFI | Hs00375371_m1 | up |
| CHL1 | Hs00219684_m1 | up |
| CITED2 | Hs01124272_g1 | down |
| CLC | Hs02379935_s1 | up |
| CLDN10 | Hs00171342_m1 | down |
| CMA1 | Hs00157019_m1 | up |
| COL8A2 | Hs00950678_g1 | up |
| CPA3 | Hs00237017_m1 | up |
| CRISP2 | Hs00377503_m1 | down |
| CRISP3 | Hs00298328_s1 | down |
| CRYM | Hs00183950_m1 | down |
| CTNNAL1 | Hs00911670_s1 | down |
| CTSC | Hs00197374_m1 | up |
| CXCL1 | Hs00697025_m1 | up |
| CXCL6 | Hs02576518_gH | up |
| DSG1 | Hs00223275_m1 | down |
| EML1 | Hs00175188_m1 | down |
| ENDOU | Hs00163869_m1 | down |
| EPPK1 | Hs00174200_m1 | up |
| FCGR3B; FCGR3A | Hs00223342_m1 | up |
| FLG | Hs00989715_m1 | down |
| GCNT3 | Hs01876357_s1 | up |
| GLDC | Hs00156558_m1 | up |
| GPR160 | Hs01878570_s1 | up |
| GRK5 | Hs00366414_m1 | up |
| GRPEL2 | Hs00275547_m1 | down |
| GYS2 | Hs00156060_m1 | down |
| HPGDS | Hs99999027_s1 | up |
| HRH1 | Hs00199583_m1 | up |
| IGFL1 | Hs00210096_m1 | down |
| IGJ | Hs00236871_m1 | up |
| IL13 | Hs00992173_m1 | up |
| IL5 | Hs00544069_m1 | up |
| IL5RA | Hs00191070_m1 | up |
| IL8 | Hs00355084_m1 | up |
| KCNJ2 | Hs00195988_m1 | up |
| KRT23 | Hs00157121_m1 | up |
| LRRC31 | Hs01075312_m1 | up |
| MMP12 | Hs00899668_m1 | up |
| MT1M | Hs00156401_m1 | down |
| MUC4 | Hs00608677_m1 | up |
| NEFL | Hs01123712_m1 | up |
| NEFM | Hs00162960_m1 | up |
| PHLDB2 | Hs00968979_m1 | up |
| PMCH | Hs01651089_g1 | up |
| PNLIPRP3 | Hs00270014_m1 | down |
| POSTN | Hs00195731_m1 | up |
| RTP4 | Hs00203383_m1 | up |
| RUNX2 | Hs01086736_m1 | up |
| SAMSN1 | Hs00209000_m1 | up |
| SLC16A6 | Hs00828387_g1 | down |
| SLC26A4 | Hs00406604_m1 | up |
| SPINK7 | Hs00167524_m1 | down |

TABLE 2-continued

Selection of 77 EoE genes identified as being significantly dysregulated

| GeneSymbol | AB AssayID | Regulation |
|---|---|---|
| SUSD2 | Hs01113125_m1 | up |
| TNFAIP6 | Hs00261445_m1 | up |
| TPSB2; TPSAB1 | Hs00863478_g1 | up |
| TSPAN12 | Hs00972098_m1 | down |
| UBD | Hs00537120_s1 | up |
| UPK1A | Hs01897804_s1 | down |

Example 5

Development and Use of the EDP and Algorithms to Differentiate EoE Patients from Normal Patients A random set of 29 samples from pediatric patients (age <21), including 14 normal (NL) and 15 EoE samples without exposure to topical or systemic glucocorticoid treatment, was selected for initial EDP analysis. The Taqman amplification reagents for the diagnostic panel of 94 representative EoE genes plus 2 housekeeping genes were selected to be embedded onto the 384 well fluidic card, as listed in Table 1 and described in Example 3. Arrayed expression data on these 96 genes per patient was then acquired by the 7900HT qPCR system (Applied Biosciences), as described in Example 3.

Figure 2A:
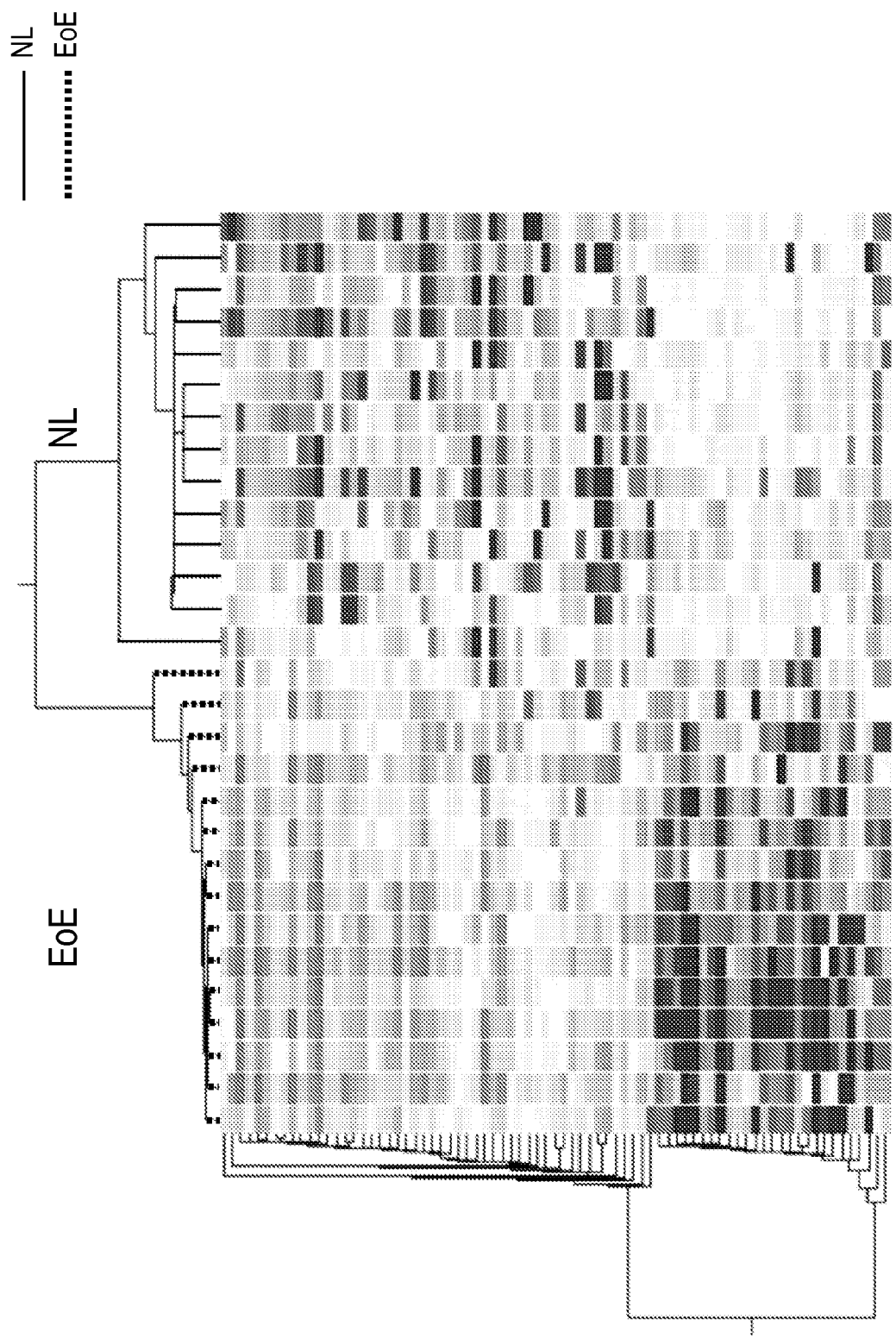
FIGS. 2A-G depict results from dual EDP algorithms for the molecular diagnosis of EoE.

Given the fact that EoE is a disorder with the involved genes regulated in bi-directions, the unique expression pattern can be used to derive a cluster analysis algorithm (also known as a dendogram algorithm), in which EoE and NL form disparate clusters. As shown in FIG. 2A, 14 NL samples and 15 EoE samples having a established histological diagnoses were initially analyzed by the cluster analysis algorithm, and the results were set up in a two-dimensional (2D) dendrogram. Clustering of both entities (genes) and conditions (EoE status) was then carried out, based on a Pearson-centered similarity algorithm.

The dendrogram clustering on the Y-axis demonstrates that the up-regulated and down-regulated EoE genes were well-represented in the EDP platform, with a similar magnitude of dysregulation compared to the mRNA microarray data. The first branch of the X-axis dendrogram serves to diagnose EoE based on the similarity of gene expression patterns, i.e. samples with the closest gene expression patterns are grouped together. As illustrated by the first branch of the dendrogram on the X-axis (clustering by condition), the EoE pattern can be readily recognized with a long distance metric separation on top of the dendrogram. All of the NL samples are clustered together on the right side of FIG. 2A, while all of the EoE samples are grouped together to the left.

Figure 2B:
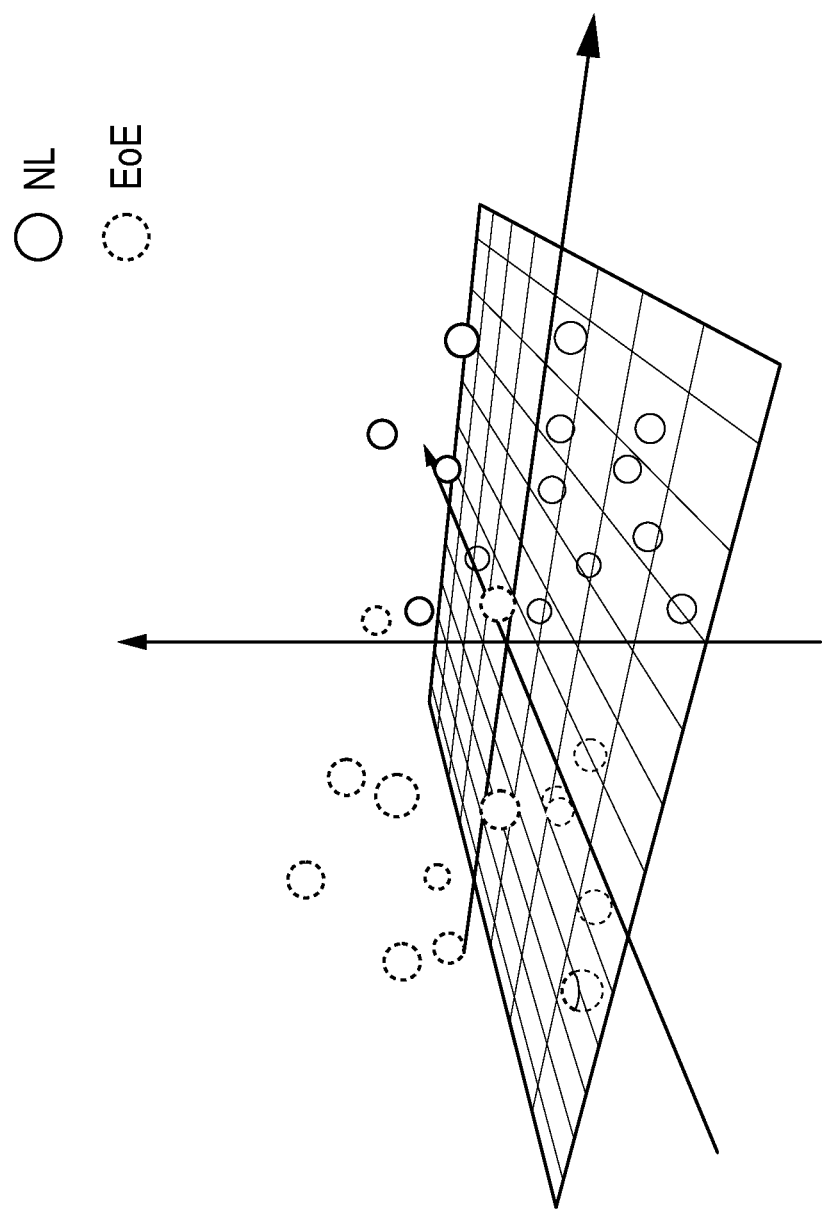
Figure 2:
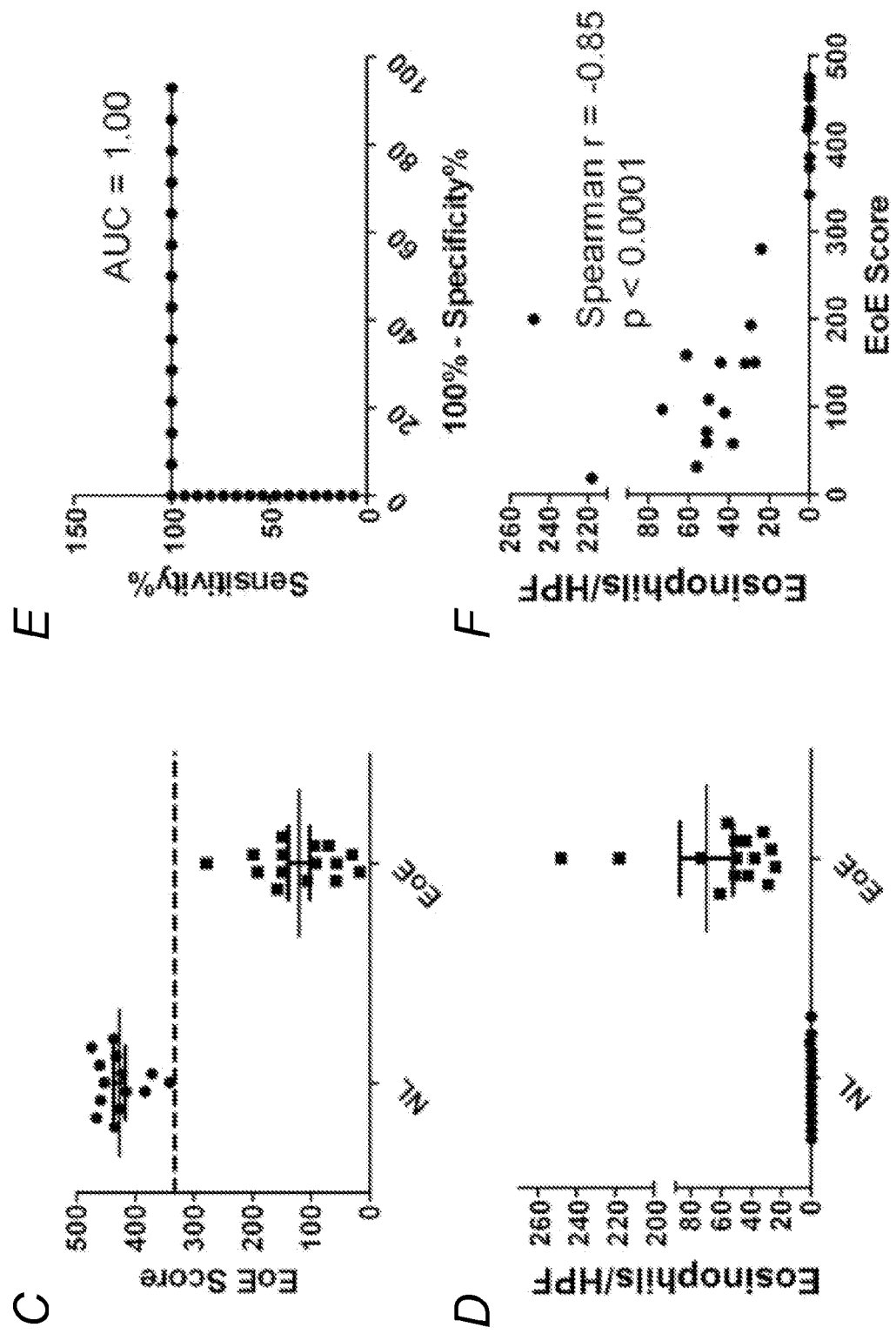
Figure 2:
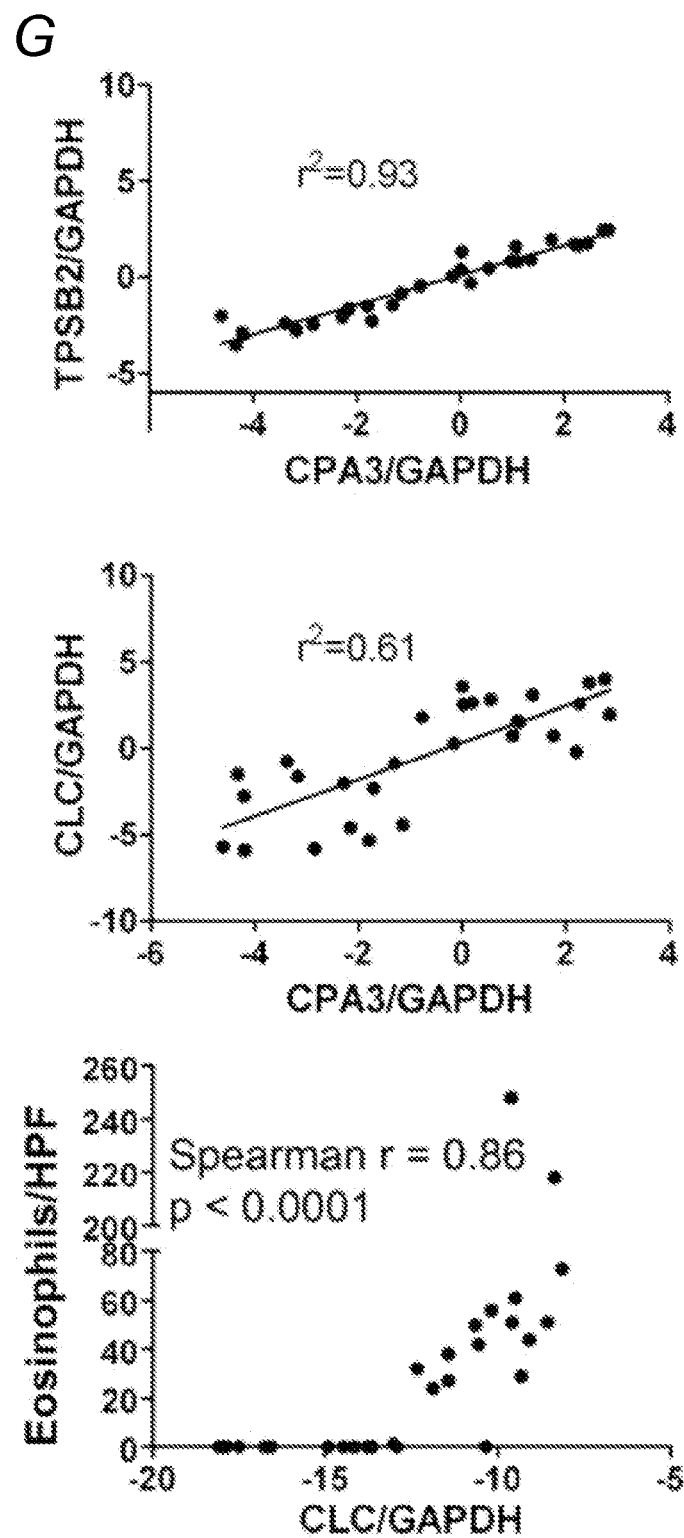

MDS analysis was performed on the same data set of 14 NL and 15 EoE samples, and the 77-gene expression was reduced to 3-D visualization representing the 77-D Euclid distance between samples (FIG. 2B). This analysis showed clear separation of EE and NL gene expression.

In addition to the dendrogram clustering algorithm, a parallel dimensionality reduction algorithm to acquire an "EoE score" was also developed to ascertain a quantitative diagnosis threshold value. Formula (3) was used to calculate the EoE score for each sample based on their raw Ct. values.

$$\text{EoE Score} = \Sigma\Delta CT = \Sigma(\text{Ct. down genes} - \text{Ct. GAPDH}) - \Sigma(\text{Ct. up genes} - \text{Ct. GAPDH}) \quad (3)$$

As demonstrated in FIG. 2C, the EoE score of the two cohorts is well separated with no overlap. Because the EoE score in this case is $\log_2$-based, the actual expression differences are larger than they appear on the Y-axis.

The EoE score strongly correlated with the eosinophil density (e.g. peak eosinophils/HPF) (FIG. 2D). With the "ΣΔCT" algorithm, receiver operating characteristic (ROC) analysis indicated that the analysis had an excellent diagnostic merit, with the area under curve (AUC) being 1.00 (FIG. 2E). A significant correlation was found between the EoE score and esophageal eosinophil levels (FIG. 2F), a surrogate marker of disease severity.

The EDP was designed to contain cell-specific markers. For instance, the two mast cell markers carboxypeptidase A3 and tryptase correlated well with each other (FIG. 2G, upper panel), indicating intra-panel reproducibility. Also, the gene for eosinophil lysophospholipase (CLC), the only highly expressed eosinophil granule gene, positively correlated with the mast cell gene (FIG. 2G, middle panel), as well as eosinophil levels (FIG. 2G, lower panel), corroborating prior findings.

FIG. 2A. After expression analysis of the raw qPCR data based on the 94 EoE genes (Table 1), a statistical screening was performed between the 14 NL patients and 15 EoE patients, resulting in 77 genes with FDR-corrected p<0.05 and fold change >2.0. Based on these 77 genes, a 2-D heatmap was created with Pearson-centered distance metrics. The hierarchical tree (dendrogram) was established on both gene entities and sample conditions. On the X-axis, the first branch of the sample condition (top) tree is utilized to differentially predict EoE or NL.

FIG. 2B. The 77-gene/dimension expression data on 14 NL and 15 EoE patients were reduced to 3-D presentation by Euclid distance-based multi-dimensional scaling (MDS) analysis for visual presentation of the expression distance between any two given samples.

FIG. 2C. An EoE scoring system was developed based on dimensionality reduction to differentiate the 15 EoE samples vs. 14 NL samples based on Formula 2 and to quantify EoE disease severity. A diagnosis cut-off line was drawn at EoE score 333 (as indicated by the dashed line); this cut-off line was derived from larger-scale studies by ROC analysis.

FIG. 2D. Levels of distal esophagus eosinophilia in units of eosinophils/HPF.

FIG. 2E. ROC curve based on FIG. 2C and the EoE score=333 diagnostic cut-off line, with an area under curve (AUC) of 1.0.

FIG. 2F. A linear correlation was established between eosinophils/HPF and EoE score, with spearman r and p values shown.

FIG. 2G. To demonstrate intra-panel target gene accuracy, based on the total of 29 patients tested herein, a representative linear regression regarding the gene intra-correlation of mast cells (CPA3 vs. tryptase), mast cell gene/eosinophil gene inter-correlation (CPA3 vs. CLC) and eosinophil gene/eosinophilia correlation (CLC vs. Eosinophils/HPF) are shown in the upper, middle and lower panels, respectively. Spearman r was displayed together with p value.

TABLE 3

| Relationship between ROC diagnostic cutoff and sensitivity and specificity (CI: confidence interval) | | | | | |
|---|---|---|---|---|---|
| Diagnostic Cutoff | Sensitivity % | 95% CI | Specificity % | 95% CI | Likelihood ratio |
| <−50.16 | 1.22 | 0.03087% to 6.608% | 100 | 92.89% to 100.0% | |
| <−46.27 | 2.439 | 0.2968% to 8.534% | 100 | 92.89% to 100.0% | |
| <−34.48 | 3.659 | 0.7609% to 10.32% | 100 | 92.89% to 100.0% | |
| <−22.41 | 4.878 | 1.345% to 12.02% | 100 | 92.89% to 100.0% | |
| <−18.10 | 6.098 | 2.009% to 13.66% | 100 | 92.89% to 100.0% | |
| <−2.336 | 7.317 | 2.732% to 15.25% | 100 | 92.89% to 100.0% | |
| <11.29 | 8.537 | 3.501% to 16.80% | 100 | 92.89% to 100.0% | |
| <15.11 | 9.756 | 4.307% to 18.32% | 100 | 92.89% to 100.0% | |
| <19.64 | 10.98 | 5.143% to 19.82% | 100 | 92.89% to 100.0% | |
| <21.46 | 12.2 | 6.006% to 21.29% | 100 | 92.89% to 100.0% | |
| <22.47 | 13.41 | 6.891% to 22.74% | 100 | 92.89% to 100.0% | |
| <26.81 | 14.63 | 7.797% to 24.17% | 100 | 92.89% to 100.0% | |
| <30.63 | 15.85 | 8.720% to 25.58% | 100 | 92.89% to 100.0% | |
| <31.85 | 17.07 | 9.661% to 26.98% | 100 | 92.89% to 100.0% | |
| <32.95 | 18.29 | 10.62% to 28.37% | 100 | 92.89% to 100.0% | |
| <34.79 | 19.51 | 11.58% to 29.74% | 100 | 92.89% to 100.0% | |
| <36.72 | 20.73 | 12.57% to 31.11% | 100 | 92.89% to 100.0% | |
| <43.51 | 21.95 | 13.56% to 32.46% | 100 | 92.89% to 100.0% | |
| <50.94 | 23.17 | 14.56% to 33.79% | 100 | 92.89% to 100.0% | |
| <54.68 | 24.39 | 15.58% to 35.12% | 100 | 92.89% to 100.0% | |
| <57.68 | 25.61 | 16.60% to 36.45% | 100 | 92.89% to 100.0% | |
| <58.33 | 26.83 | 17.64% to 37.76% | 100 | 92.89% to 100.0% | |
| <59.09 | 28.05 | 18.68% to 39.06% | 100 | 92.89% to 100.0% | |
| <64.12 | 29.27 | 19.74% to 40.35% | 100 | 92.89% to 100.0% | |
| <70.24 | 30.49 | 20.80% to 41.64% | 100 | 92.89% to 100.0% | |
| <71.53 | 31.71 | 21.87% to 42.92% | 100 | 92.89% to 100.0% | |
| <74.61 | 32.93 | 22.94% to 44.19% | 100 | 92.89% to 100.0% | |
| <80.07 | 34.15 | 24.03% to 45.45% | 100 | 92.89% to 100.0% | |
| <84.27 | 35.37 | 25.12% to 46.70% | 100 | 92.89% to 100.0% | |
| <87.77 | 36.59 | 26.22% to 47.95% | 100 | 92.89% to 100.0% | |
| <90.09 | 37.8 | 27.32% to 49.19% | 100 | 92.89% to 100.0% | |
| <91.76 | 39.02 | 28.44% to 50.43% | 100 | 92.89% to 100.0% | |
| <93.13 | 40.24 | 29.56% to 51.66% | 100 | 92.89% to 100.0% | |
| <94.41 | 41.46 | 30.68% to 52.88% | 100 | 92.89% to 100.0% | |
| <96.02 | 42.68 | 31.82% to 54.10% | 100 | 92.89% to 100.0% | |
| <100.0 | 43.9 | 32.95% to 55.30% | 100 | 92.89% to 100.0% | |
| <105.4 | 45.12 | 34.10% to 56.51% | 100 | 92.89% to 100.0% | |
| <110.0 | 46.34 | 35.25% to 57.70% | 100 | 92.89% to 100.0% | |
| <113.3 | 47.56 | 36.41% to 58.89% | 100 | 92.89% to 100.0% | |

TABLE 3-continued

Relationship between ROC diagnostic cutoff and sensitivity and specificity (CI: confidence interval)

| Diagnostic Cutoff | Sensitivity % | 95% CI | Specificity % | 95% CI | Likelihood ratio |
|---|---|---|---|---|---|
| <120.4 | 48.78 | 37.58% to 60.08% | 100 | 92.89% to 100.0% | |
| <136.7 | 50 | 38.75% to 61.25% | 100 | 92.89% to 100.0% | |
| <146.9 | 51.22 | 39.92% to 62.42% | 100 | 92.89% to 100.0% | |
| <148.1 | 52.44 | 41.11% to 63.59% | 100 | 92.89% to 100.0% | |
| <149.4 | 53.66 | 42.30% to 64.75% | 100 | 92.89% to 100.0% | |
| <149.9 | 54.88 | 43.49% to 65.90% | 100 | 92.89% to 100.0% | |
| <152.5 | 56.1 | 44.70% to 67.05% | 100 | 92.89% to 100.0% | |
| <156.8 | 57.32 | 45.90% to 68.18% | 100 | 92.89% to 100.0% | |
| <162.9 | 58.54 | 47.12% to 69.32% | 100 | 92.89% to 100.0% | |
| <169.9 | 59.76 | 48.34% to 70.44% | 100 | 92.89% to 100.0% | |
| <178.0 | 60.98 | 49.57% to 71.56% | 100 | 92.89% to 100.0% | |
| <183.5 | 62.2 | 50.81% to 72.68% | 100 | 92.89% to 100.0% | |
| <188.1 | 63.41 | 52.05% to 73.78% | 100 | 92.89% to 100.0% | |
| <193.3 | 64.63 | 53.30% to 74.88% | 100 | 92.89% to 100.0% | |
| <196.8 | 65.85 | 54.55% to 75.97% | 100 | 92.89% to 100.0% | |
| <203.5 | 67.07 | 55.81% to 77.06% | 100 | 92.89% to 100.0% | |
| <208.0 | 68.29 | 57.08% to 78.13% | 100 | 92.89% to 100.0% | |
| <211.4 | 69.51 | 58.36% to 79.20% | 100 | 92.89% to 100.0% | |
| <220.5 | 70.73 | 59.65% to 80.26% | 100 | 92.89% to 100.0% | |
| <230.6 | 71.95 | 60.94% to 81.32% | 100 | 92.89% to 100.0% | |
| <238.1 | 73.17 | 62.24% to 82.36% | 100 | 92.89% to 100.0% | |
| <243.1 | 74.39 | 63.55% to 83.40% | 100 | 92.89% to 100.0% | |
| <246.6 | 75.61 | 64.88% to 84.42% | 100 | 92.89% to 100.0% | |
| <249.0 | 76.83 | 66.21% to 85.44% | 100 | 92.89% to 100.0% | |
| <258.0 | 76.83 | 66.21% to 85.44% | 98 | 89.35% to 99.95% | 38.41 |
| <272.2 | 78.05 | 67.54% to 86.44% | 98 | 89.35% to 99.95% | 39.02 |
| <277.7 | 79.27 | 68.89% to 87.43% | 98 | 89.35% to 99.95% | 39.63 |
| <278.8 | 80.49 | 70.26% to 88.42% | 98 | 89.35% to 99.95% | 40.24 |
| <280.1 | 81.71 | 71.63% to 89.38% | 98 | 89.35% to 99.95% | 40.85 |
| <287.2 | 82.93 | 73.02% to 90.34% | 98 | 89.35% to 99.95% | 41.46 |
| <295.2 | 84.15 | 74.42% to 91.28% | 98 | 89.35% to 99.95% | 42.07 |
| <304.2 | 85.37 | 75.83% to 92.20% | 98 | 89.35% to 99.95% | 42.68 |
| <312.1 | 86.59 | 77.26% to 93.11% | 98 | 89.35% to 99.95% | 43.29 |
| <316.4 | 87.8 | 78.71% to 93.99% | 98 | 89.35% to 99.95% | 43.9 |
| <325.0 | 89.02 | 80.18% to 94.86% | 98 | 89.35% to 99.95% | 44.51 |
| <330.4 | 89.02 | 80.18% to 94.86% | 96 | 86.29% to 99.51% | 22.26 |
| <331.7 | 90.24 | 81.68% to 95.69% | 96 | 86.29% to 99.51% | 22.56 |
| <333.7 | 91.46 | 83.20% to 96.50% | 96 | 86.29% to 99.51% | 22.87 |
| <335.8 | 91.46 | 83.20% to 96.50% | 94 | 83.45% to 98.75% | 15.24 |
| <338.9 | 92.68 | 84.75% to 97.27% | 94 | 83.45% to 98.75% | 15.45 |
| <343.3 | 92.68 | 84.75% to 97.27% | 92 | 80.77% to 97.78% | 11.59 |
| <346.3 | 92.68 | 84.75% to 97.27% | 90 | 78.19% to 96.67% | 9.27 |
| <350.1 | 92.68 | 84.75% to 97.27% | 88 | 75.69% to 95.47% | 7.72 |
| <356.1 | 92.68 | 84.75% to 97.27% | 86 | 73.26% to 94.18% | 6.62 |
| <361.1 | 92.68 | 84.75% to 97.27% | 84 | 70.89% to 92.83% | 5.79 |
| <365.7 | 92.68 | 84.75% to 97.27% | 82 | 68.56% to 91.42% | 5.15 |
| <370.6 | 92.68 | 84.75% to 97.27% | 80 | 66.28% to 89.97% | 4.63 |
| <374.7 | 92.68 | 84.75% to 97.27% | 78 | 64.04% to 88.47% | 4.21 |
| <378.5 | 93.9 | 86.34% to 97.99% | 78 | 64.04% to 88.47% | 4.27 |
| <382.0 | 93.9 | 86.34% to 97.99% | 76 | 61.83% to 86.94% | 3.91 |
| <385.1 | 93.9 | 86.34% to 97.99% | 74 | 59.65% to 85.37% | 3.61 |
| <386.7 | 93.9 | 86.34% to 97.99% | 72 | 57.51% to 83.77% | 3.35 |
| <387.7 | 93.9 | 86.34% to 97.99% | 70 | 55.39% to 82.14% | 3.13 |
| <388.8 | 93.9 | 86.34% to 97.99% | 68 | 53.30% to 80.48% | 2.93 |
| <390.3 | 95.12 | 87.98% to 98.66% | 68 | 53.30% to 80.48% | 2.97 |
| <392.4 | 95.12 | 87.98% to 98.66% | 66 | 51.23% to 78.79% | 2.8 |
| <395.1 | 96.34 | 89.68% to 99.24% | 66 | 51.23% to 78.79% | 2.83 |
| <399.5 | 96.34 | 89.68% to 99.24% | 64 | 49.19% to 77.08% | 2.68 |
| <403.4 | 96.34 | 89.68% to 99.24% | 62 | 47.18% to 75.35% | 2.54 |
| <405.0 | 97.56 | 91.47% to 99.70% | 62 | 47.18% to 75.35% | 2.57 |
| <405.6 | 98.78 | 93.39% to 99.97% | 62 | 47.18% to 75.35% | 2.6 |
| <407.5 | 98.78 | 93.39% to 99.97% | 60 | 45.18% to 73.59% | 2.47 |
| <409.4 | 98.78 | 93.39% to 99.97% | 58 | 43.21% to 71.81% | 2.35 |
| <411.2 | 98.78 | 93.39% to 99.97% | 56 | 41.25% to 70.01% | 2.25 |
| <414.6 | 98.78 | 93.39% to 99.97% | 54 | 39.32% to 68.19% | 2.15 |
| <416.5 | 98.78 | 93.39% to 99.97% | 52 | 37.42% to 66.34% | 2.06 |
| <416.6 | 98.78 | 93.39% to 99.97% | 50 | 35.53% to 64.47% | 1.98 |
| <417.0 | 98.78 | 93.39% to 99.97% | 48 | 33.66% to 62.58% | 1.9 |
| <418.4 | 98.78 | 93.39% to 99.97% | 46 | 31.81% to 60.68% | 1.83 |
| <420.5 | 98.78 | 93.39% to 99.97% | 44 | 29.99% to 58.75% | 1.76 |
| <421.6 | 98.78 | 93.39% to 99.97% | 42 | 28.19% to 56.79% | 1.7 |
| <422.1 | 98.78 | 93.39% to 99.97% | 40 | 26.41% to 54.82% | 1.65 |
| <423.0 | 98.78 | 93.39% to 99.97% | 38 | 24.65% to 52.82% | 1.59 |
| <425.5 | 98.78 | 93.39% to 99.97% | 36 | 22.92% to 50.81% | 1.54 |
| <427.7 | 98.78 | 93.39% to 99.97% | 34 | 21.21% to 48.77% | 1.5 |
| <428.1 | 98.78 | 93.39% to 99.97% | 32 | 19.52% to 46.70% | 1.45 |

TABLE 3-continued

Relationship between ROC diagnostic cutoff and sensitivity and specificity (CI: confidence interval)

| Diagnostic Cutoff | Sensitivity % | 95% CI | Specificity % | 95% CI | Likelihood ratio |
|---|---|---|---|---|---|
| <429.9 | 98.78 | 93.39% to 99.97% | 30 | 17.86% to 44.61% | 1.41 |
| <432.4 | 98.78 | 93.39% to 99.97% | 28 | 16.23% to 42.49% | 1.37 |
| <434.2 | 98.78 | 93.39% to 99.97% | 26 | 14.63% to 40.35% | 1.33 |
| <436.2 | 98.78 | 93.39% to 99.97% | 24 | 13.06% to 38.17% | 1.3 |
| <439.7 | 98.78 | 93.39% to 99.97% | 22 | 11.53% to 35.96% | 1.27 |
| <442.0 | 100 | 95.60% to 100.0% | 22 | 11.53% to 35.96% | 1.28 |
| <442.2 | 100 | 95.60% to 100.0% | 20 | 10.03% to 33.72% | 1.25 |
| <442.6 | 100 | 95.60% to 100.0% | 18 | 8.576% to 31.44% | 1.22 |
| <442.7 | 100 | 95.60% to 100.0% | 16 | 7.170% to 29.11% | 1.19 |
| <445.1 | 100 | 95.60% to 100.0% | 14 | 5.819% to 26.74% | 1.16 |
| <450.1 | 100 | 95.60% to 100.0% | 12 | 4.534% to 24.31% | 1.14 |
| <455.8 | 100 | 95.60% to 100.0% | 10 | 3.328% to 21.81% | 1.11 |
| <459.2 | 100 | 95.60% to 100.0% | 8 | 2.223% to 19.23% | 1.09 |
| <460.5 | 100 | 95.60% to 100.0% | 6 | 1.255% to 16.55% | 1.06 |
| <463.9 | 100 | 95.60% to 100.0% | 4 | 0.4881% to 13.71% | 1.04 |
| <470.7 | 100 | 95.60% to 100.0% | 2 | 0.05062% to 10.65% | 1.02 |

Example 6

Development and Use of the EDP and Algorithms to Diagnose EoE

To examine the validity of the dual algorithms, the diagnostic capacity of EDP was tested by processing 8 blinded samples with varying eosinophil numbers from symptomatic new patients. For the cluster analysis algorithm, the 8 unknown samples were mixed with the previously described EoE and NL cohorts (Example 5) and established the dendrogram shown on the X-axis of FIG. 3A. Of the 8 unknown samples, seven were grouped into the NL cluster, while the one remaining sample was grouped into the EoE cluster. These findings were 100% consistent with the clinical pathology count (0, 0, 0, 0, 0, 0, 1, 2, and 73 eosinophils/HPF, respectively).

With the ΣΔCT algorithm, EoE scores for the 8 unknown patients were juxtaposed to reference NL and EoE algorithm cohorts with a previously determined diagnostic cut-off (absolute value=333), as shown in FIG. 3B. All of the 8 diagnoses were successfully predicted by the ΣΔCT algorithm as well.

To evaluate the inter-panel reproducibility, two patient RNA samples were selected (986 and 990) with intermediate transcriptome (up and down-regulated genes). The reverse transcription was re-performed, and their cDNA was processed six months later (Dec. 23, 2010 and May 20, 2011) with different EDP fluidic cards. After clustering with the reference NL and EoE algorithm cohorts, the heatmaps for the two samples were aligned side-by-side, indicating little signature difference (FIG. 3C).

In order to confirm the highly reproducible gene expression signature down to each gene at the raw Ct. level, a Bland-Altman analysis plotting was performed on the raw Ct. value of each of the 96 genes (x-axis) and the Ct. value difference between the older run and the average of both runs (FIG. 3D, A: early run, B: later run; top panel, sample I; bottom panel, sample II). The flat line distribution along the x-axis (difference=0) for both samples indicates that the raw Ct. value between different EDP amplifications are highly stable for the 96 embedded genes. To further test the correlation between the two EDP analyses, the linear correlation was performed on the raw Ct. values of each of the 96 genes with the Spearman r correlation plus 95% CI on the graph (FIG. 3E), indicating a highly correlated signature analysis for each gene.

Figure 3A:
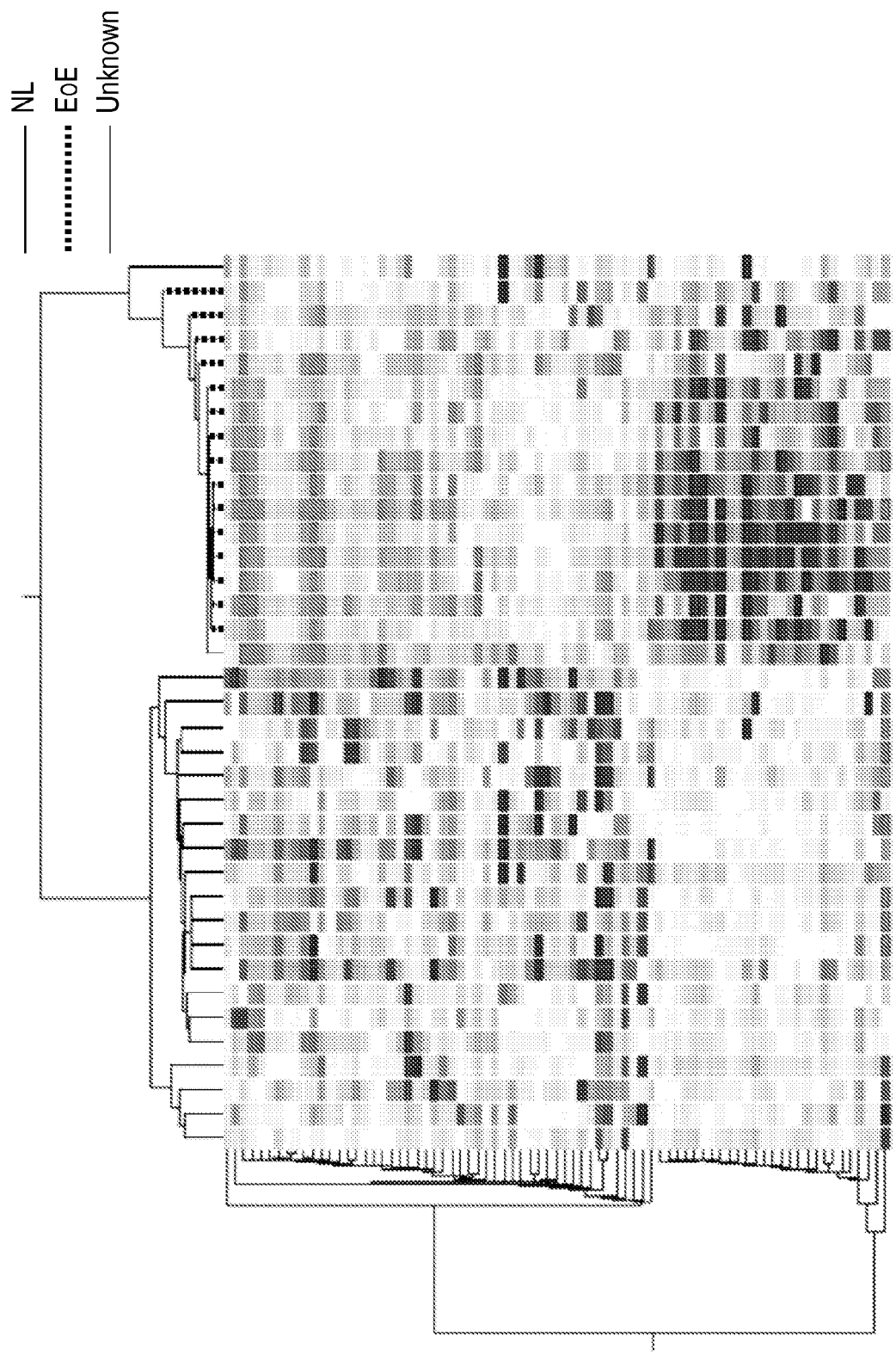
FIGS. 3A-E depict a clinical utility evaluation with blinded patient cohorts using the dual algorithms, as well as the reproducibility of the EDP analysis. Results evaluated the 77 core EoE genes for 8 unknown samples.
Figure 3:
Figure 3:
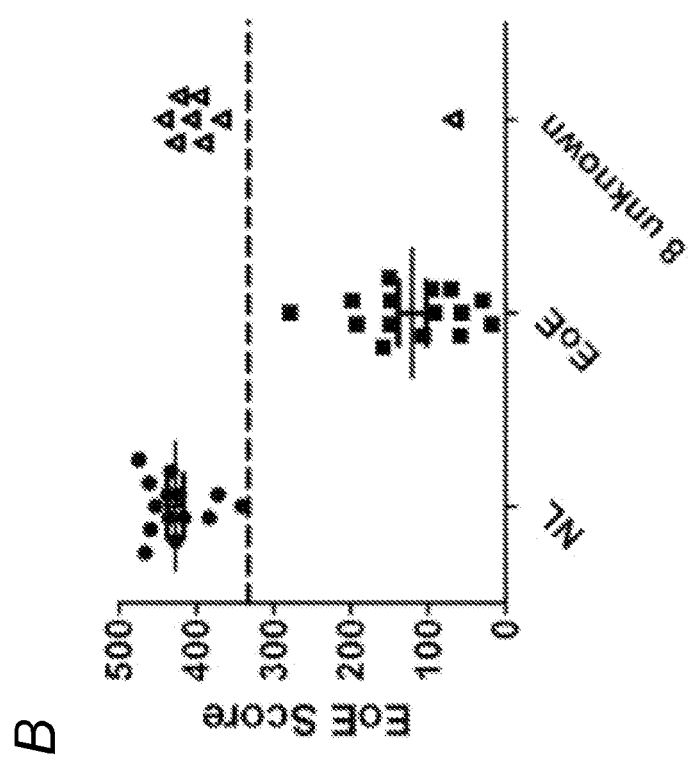

FIG. 3A. The clinical utility of the EDP was assessed in a blinded fashion on 8 new incoming patients with the dual algorithms developed as described herein. Based on the 77 core EoE genes acquired statistically as disclosed above (Example 5), the cluster analysis was performed on a heatmap to provide a diagnosis for 8 unknown samples (tree colors: EoE, red; NL, blue; 8 unknown samples, green). The 8 blinded samples were co-cluster-analyzed (Pearson centered distance metric) with the previously mentioned 15 EoE (labeled red) and 14 NL samples (labeled blue). Of the 8 unknown samples, 7 grouped with the NL cluster, while only one clustered with the EoE cohorts. These results were 100% consistent with the clinical pathology findings and the pathology diagnosis.

FIG. 3B. EoE scores were calculated in the unknown 8 patients with NL and EoE algorithm developing cohorts as reference. The cut-off of 333 (dashed line) clearly demarcated the separation of 7 inactive and 1 active samples.

FIG. 3C. The reproducibility of the EDP results was tested by reverse-transcribing and PCR-amplifying two RNA samples (I and II) with a different fluidic card at different times a half-year apart (data A and data B). The heatmap of the two samples run in different batches exhibits a highly comparable transcriptome when co-clustering with NL and EoE reference cohorts.

Figure 3D:
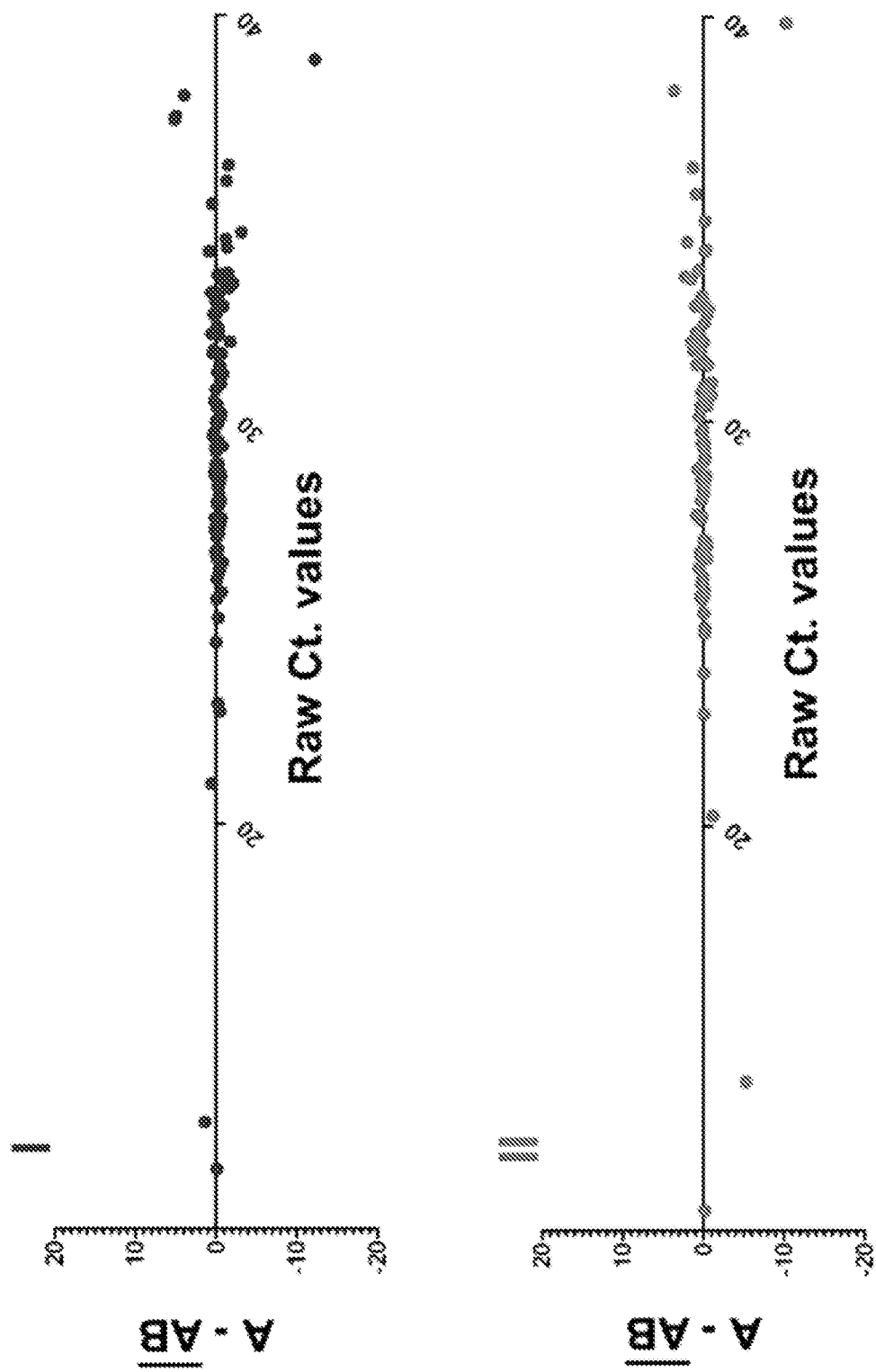

FIG. 3D. The repetitive sets of expression data from sample I (top panel) and II (bottom panel) were plotted by raw Ct value of 96 genes (X-axis) vs. the difference between raw Ct value A and the average of Ct value A and B by Bland-Altman analysis, demonstrating the variance between the two data sets.

Figure 3E:
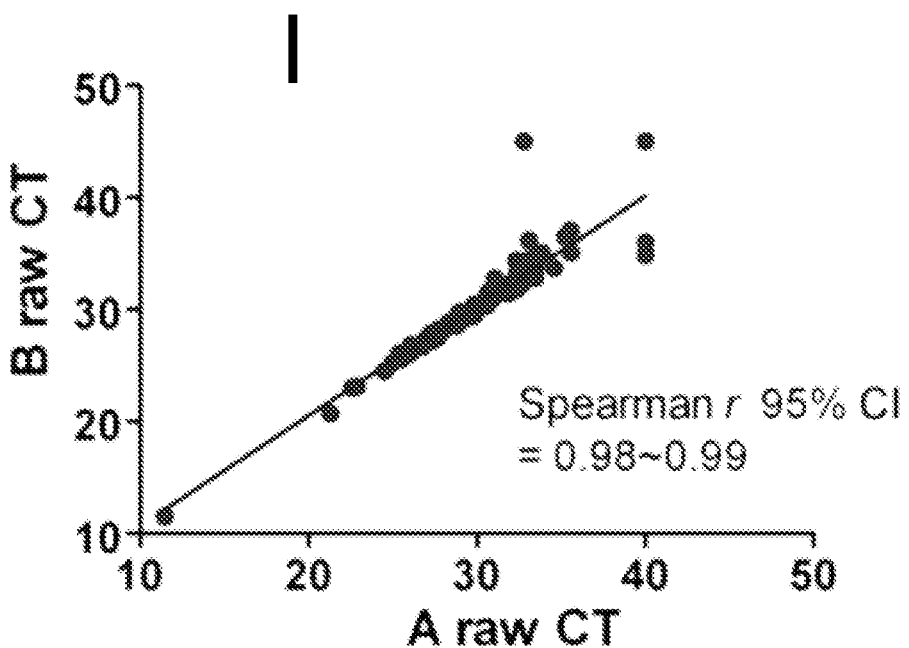
Figure 3E:
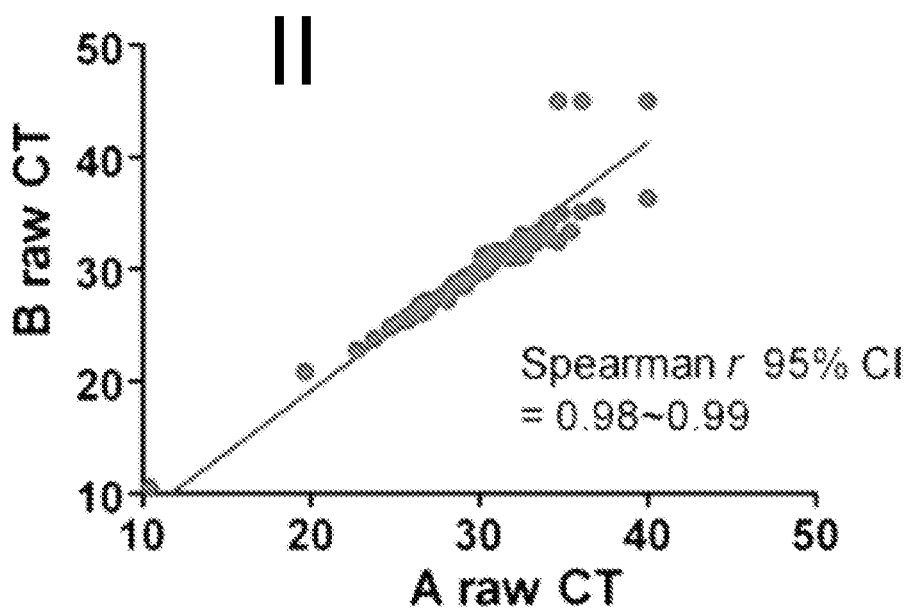

FIG. 3E. Raw Ct values on each of the 96 genes from sample I (top panel) and II (bottom panel) were double plotted between the two repetitions and subjected to linear regression analysis. Spearman r values with 95% CI are indicated on the chart.

Example 7

Use of the EDP and Algorithms to Distinguish Between Normal Samples and EoE Remission Samples Previous microarray data has identified a subset of EoE genes that are resistant to steroid therapy regardless of the absence of eosinophils, as well as a unique set of genes that are upregulated in response to glucocorticoid exposure (Blanchard et al. 2007. *J Allergy Clin Immunol* 120:1292-1300, which is incorporated herein by reference in its entirety). Therefore, the EDP panel was designed to include a selection of the EoE genes resistant to steroid therapy, termed "EoE remission genes," as well as several steroid-induced EoE genes in order to determine if the panel is also able to distinguish between EoE remission and NL samples and to assess glucocorticoid exposure (for genes related to these purposes, see Table 1).

Figure 4A:
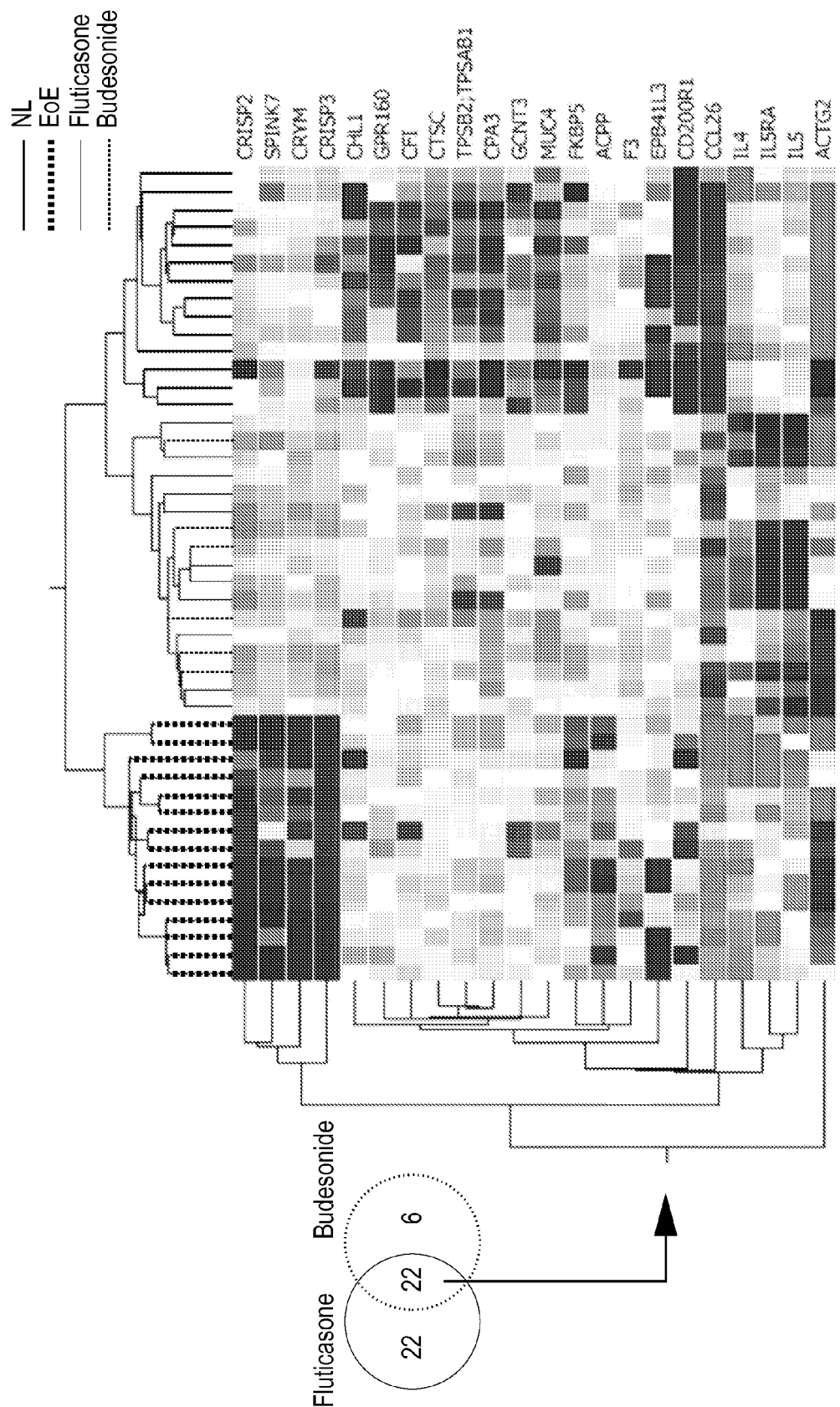
FIGS. 4A-D depict the ability of the EDP to discriminate EoE remission patients from normal patients, using the EoE transcriptome profile from 17 EoE remission patients on either fluticasone or budesonide.
Figure 4:
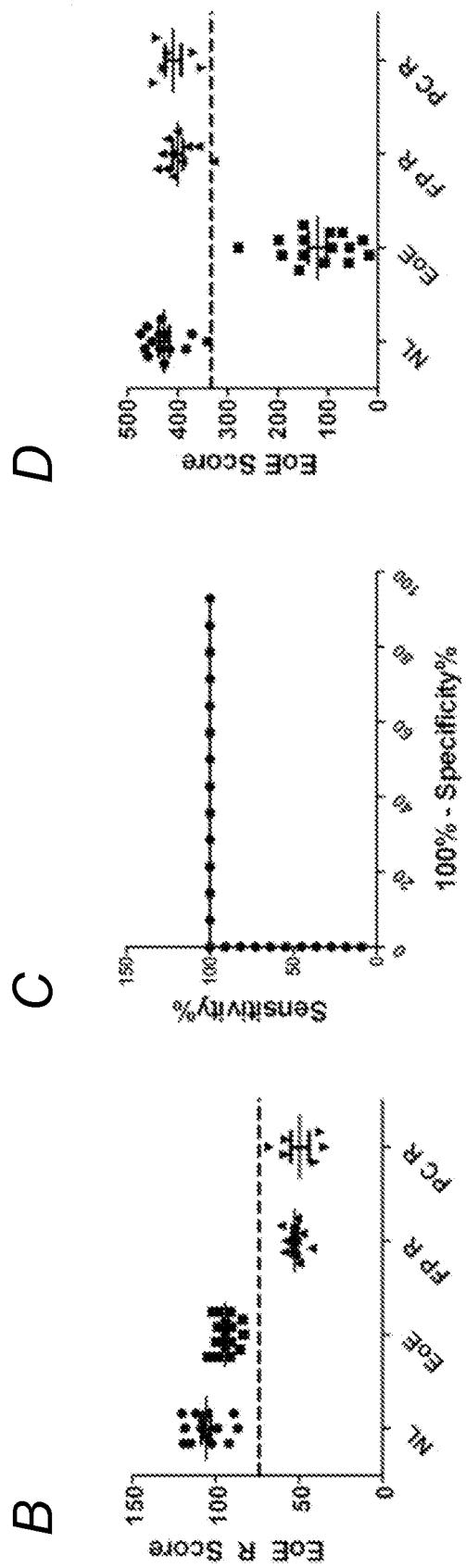

For this investigation, 11 EoE patients responding well to swallowed topical fluticasone propionate (FLOVENT®) therapy and 6 EoE patients responding well to budesonide (PULMICORT RESPULES®) were recruited; these patients had 0-2 eosinophils/HPF, verifying their remission status. In order to acquire the related genes for these purpose, a screening was performed between NL and EoE remission cohorts (Example 3, FDR-corrected p<0.05, fold change >2.0), resulting in the identification of 44 significant genes for fluticasone responders and 28 significant genes for budesonide responders. The overlapping 22 genes that were significantly different between NL and EoE remission patients in both fluticasone and budesonide cases were then selected. A dendrogram was developed on the heat map based on this 22-gene set, and 3 different clusters were readily observed (FIG. 4A). Both EoE remission cohorts separated as a unique cluster, serving as the diagnostic identity signature for EoE remission with the cluster analysis algorithm.

Within the scope of the EoE remission 22-gene subset, the $\Sigma\Delta CT$ algorithm was used to derive an EoE remission (EoE R) score to quantitatively differentiate between NL and EoE remission. Using a ROC-selected cutoff of EoE R score=74, as shown in FIG. 4B, NL and the two EoE remission cohorts were well discriminated. The rectangular-shaped ROC curve indicates little overlap (FIG. 4C). When the $\Sigma\Delta CT$ algorithm was used on the 77 core EoE genes serving for EoE diagnosis, the two cohorts of remission patients exhibited a normal signature/EoE score indistinguishable from NL (FIG. 4D).

FIG. 4A. The EoE transcriptome profiles of the biopsies from 17 EoE remission patients (treated with swallowed fluticasone propionate, at n=11, or budesonide, at n=6) were acquired by running the EDP (Example 3). Statistical analysis between NL and the two EoE remission cohorts was performed, resulting in the identification of 22 significant genes present in both fluticasone- and budesonide-regulated gene sets (FDR-corrected p<0.05, fold change >2.0). Based on this set of 22 remission genes, a double-clustered analysis heatmap was generated to evaluate the gene expression pattern of EoE remission (fluticasone and budesonide) compared to NL and EoE patients.

FIG. 4B. Based on the set of 22 steroid remission genes, the remission score (EoE R score) for each patient was calculated by 1-D reduction to quantitatively differentiate the remission patients from NL patients. A diagnostic cutoff line of EoE R score=74 was derived from ROC analysis as shown in C.

FIG. 4C. A ROC curve with a diagnostic cutoff line of EoE R score=74 is shown.

FIG. 4D. Based on the 77 EoE diagnostic genes, EoE scores were also calculated to assess the EoE status of these remission patients. The EoE score=333 cut-off line is indicated on the graph.

TABLE 4

Subset of 22 EoE genes for remission score

| GeneSymbol | Regulation |
|---|---|
| CRISP2 | down |
| CHL1 | down |
| GPR160 | down |
| CFI | down |
| FKBP5 | down |
| CTSC | down |
| CD200R1 | down |
| TPSB2; TPSAB1 | down |
| SPINK7 | down |
| CCL26 | down |
| CRISP3 | down |
| F3 | down |
| CPA3 | down |
| MUC4 | down |
| EPB41L3 | down |
| GCNT3 | down |
| ACPP | down |
| CRYM | down |
| IL4 | up |
| ACTG2 | up |
| IL5RA | up |
| IL5 | up |

Example 8

Use of the EDP and Algorithms to Analyze FFPE Samples

Molecular analysis of previously collected clinically archived formalin-fixed paraffin-embedded (FFPE) samples is particularly valuable for multiple reasons, including the access to longitudinal clinical follow-up information, potentially reducing the need for extra biopsies for molecular diagnosis, as well as definitive retrospective diagnosis. Accordingly, the disclosed eosinophilic esophagitis diagnostic panel (EDP) was tested to determine whether it is capable of analyzing FFPE biopsy samples.

Paraffin-embedded samples were obtained from 4 patients diagnosed with EoE (>15 eosinophils/HPF) and 4 patients having a NL diagnosis (0 eosinophils/HPF). Within the scope of the previously mentioned 77 core EoE genes, the double-clustered heat map for the 4 FFPE NL and 4 FFPE EoE samples demonstrates a pronounced separation between NL and EoE in FFPE format with the up and down expression patterns retained (FIG. 5A).

In order to evaluate the FFPE diagnostic potential, the 8 blinded FFPE samples were then cluster-analyzed together with the fresh 15 EoE and 14 NL samples based on the 77 significant EoE genes derived from fresh EoE-NL analysis (Example 5) to determine if EoE and NL diagnoses from FFPE samples group with those corresponding fresh samples. The dendrogram successfully predicted the disease status of the 8 blinded FFPE samples (FIG. 5B). The FFPE samples cannot be readily distinguished from fresh samples on the heat map, which indicates a retained expression signature after years of paraffin archiving. Therefore, despite the fact that FFPE RNA is highly degraded, the diagnostic panel is able to provide significant diagnostic value for FFPE samples.

FIG. 5C illustrates a representative spectrometry results for RNA isolated from FFPE sections with high RNA purity despite low integrity. With the $\Sigma\Delta CT$ algorithm, the EoE score was calculated based on the Ct. value of the 77 core EoE genes in reference to fresh NL and EoE algorithm cohorts (FIG. 5D); as shown, FFPE NL and FFPE EoE cohorts are well-separated on the EoE score scale, and the 333 EoE diagnostic cut-off line applied for fresh tissue diagnosis is readily applicable to the FFPE samples. Together, these data demonstrate that the dual diagnostic algorithms derived from fresh samples can be readily applied to clinically archived FFPE samples without modification.

Figure 5A:
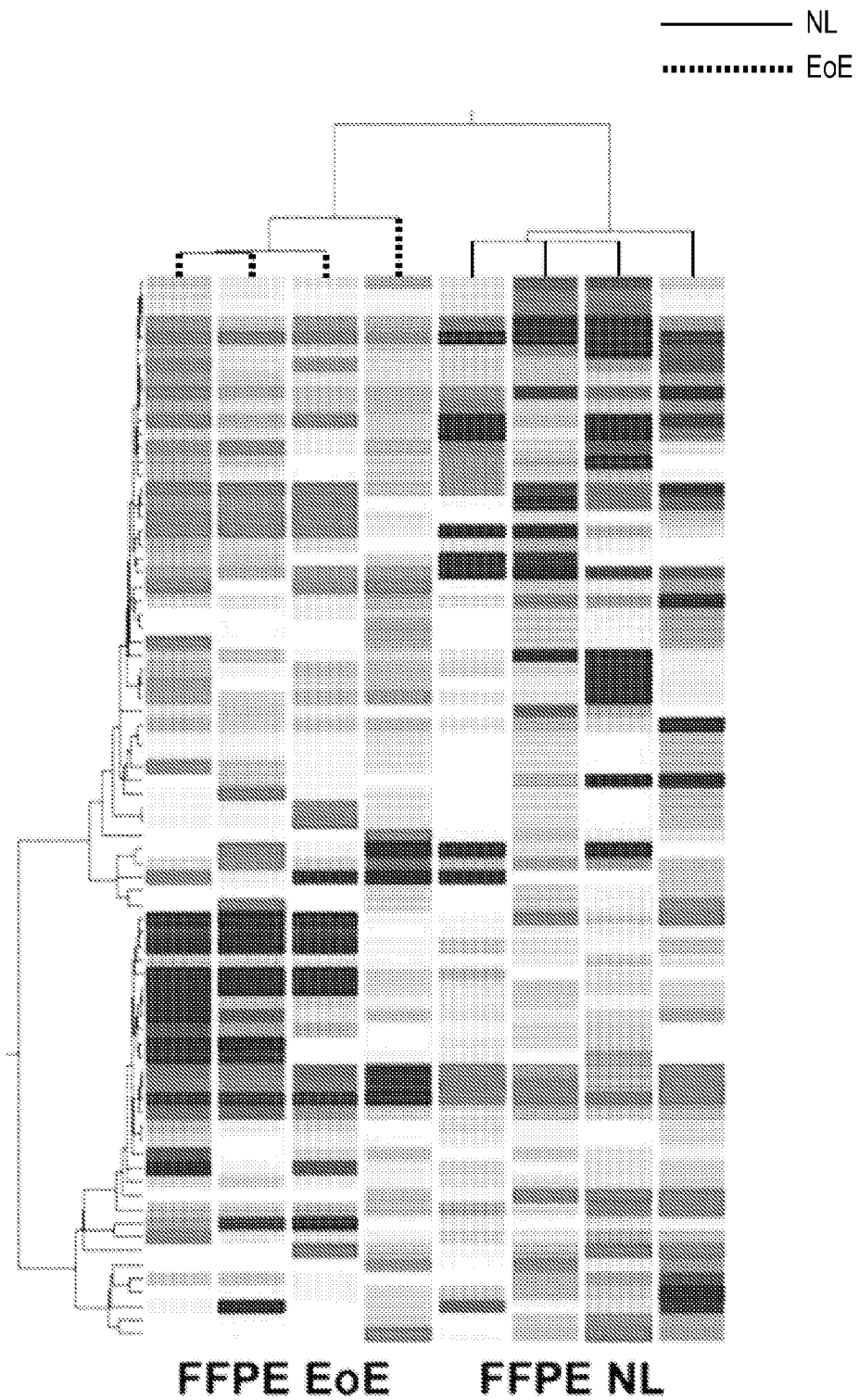
FIGS. 5A-D depict the capacity of the EDP to evaluate formalin-embedded paraffin-fixed (FFPE) samples with both algorithms.
Figure 5B:
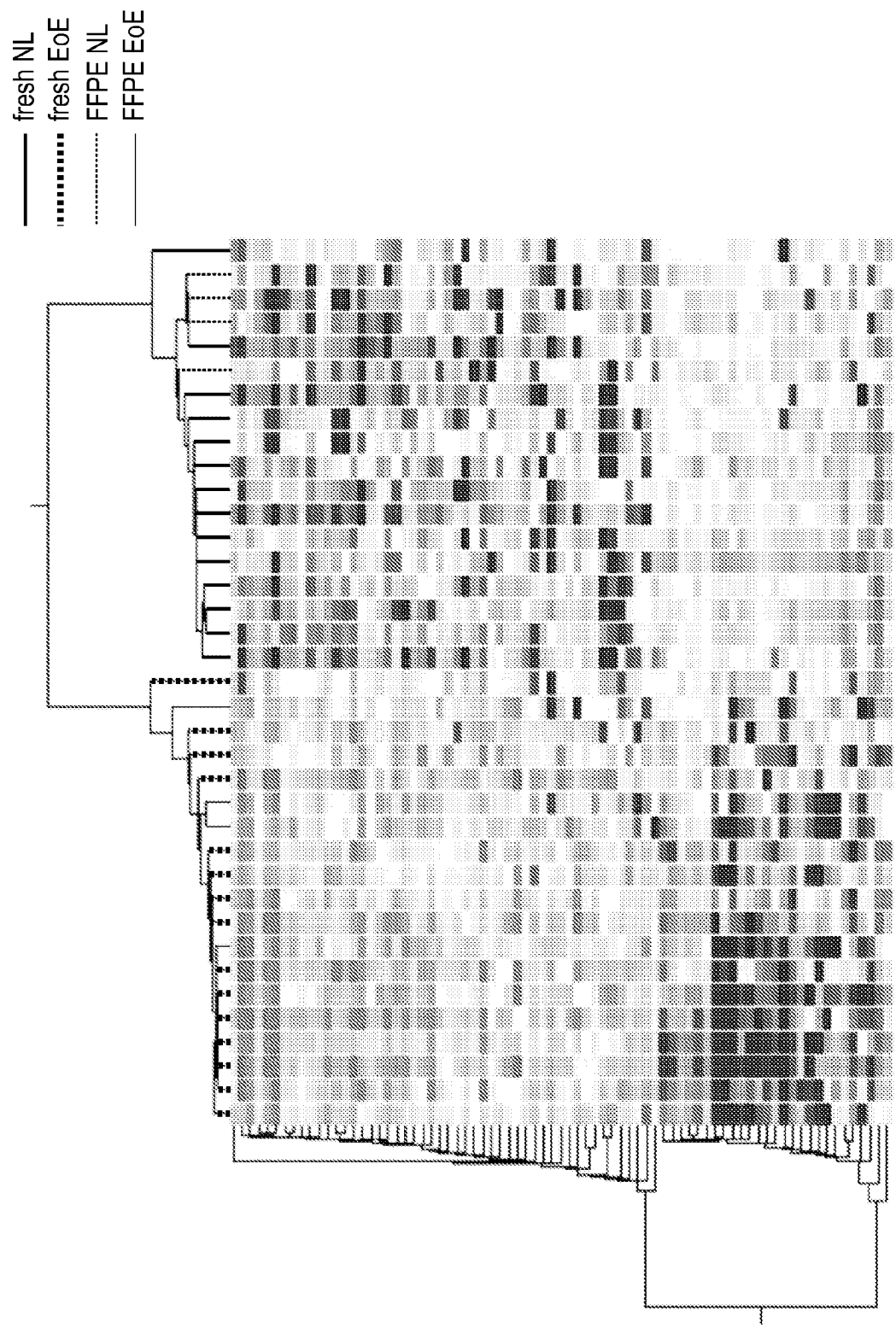
Figure 5:
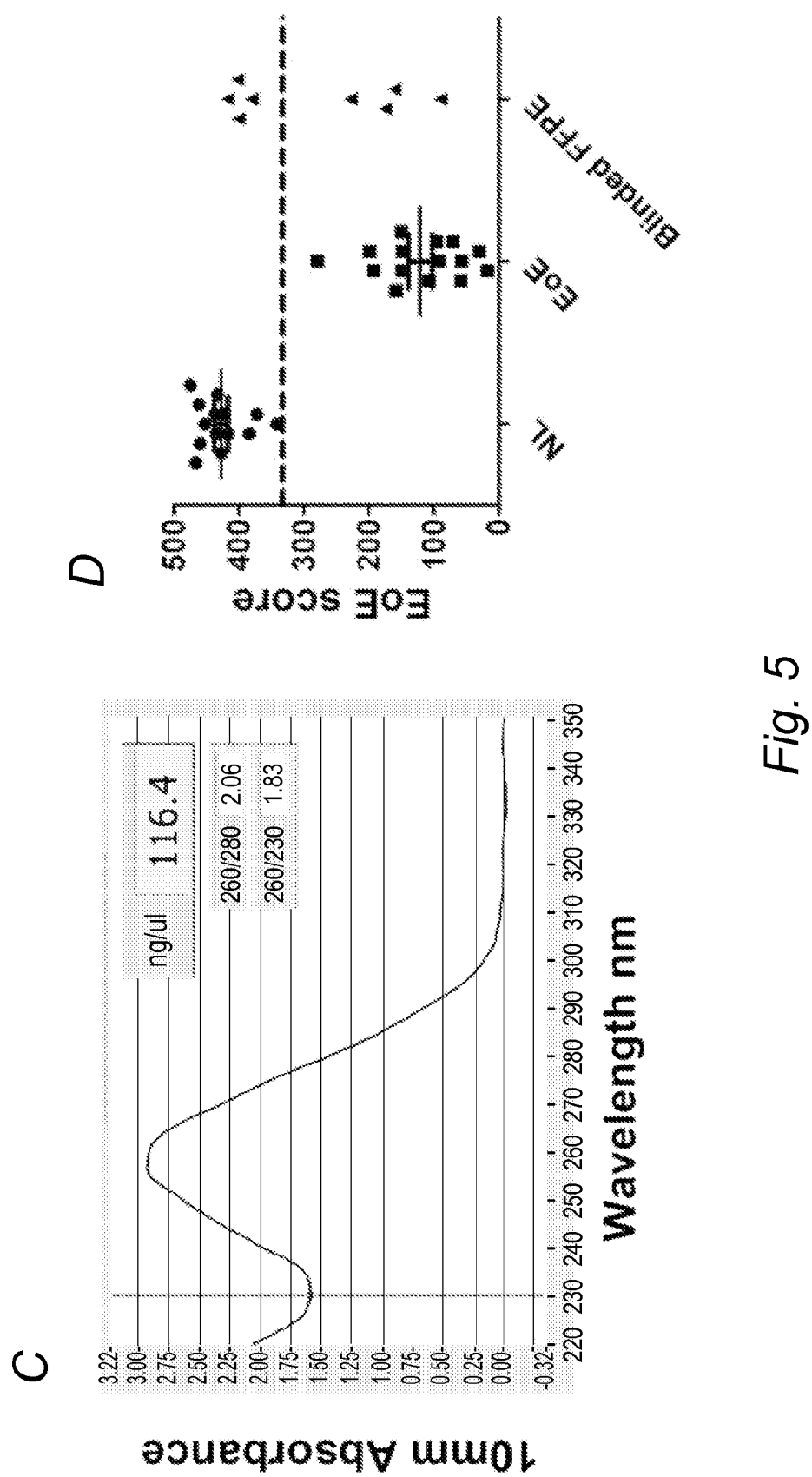

FIG. 5A. In order to evaluate the capacity of the diagnostic panel (Example 3) to diagnose formalin-fixed paraffin-embedded (FFPE) samples, 4 EoE and 4 NL FFPE samples were selected, and total RNA was extracted from 80 μm of paraffin sections from single biopsies. The EDP was performed using the same amplification protocol as conducted for fresh biopsy samples (Example 3). The heatmap for the 8 blinded FFPE samples is shown based on the 77 core EoE genes. The cluster algorithm discrimination is shown at the top of the heatmap.

FIG. 5B. To further examine the diagnostic potential for FFPE samples and to compare these samples to the fresh transcriptome, cluster analysis was performed on the 8 FFPE samples with the fresh EoE and NL sample pool based on the 77 genes identified as significant from fresh samples (Example 5). The 4 FFPE samples in each group clustered with the corresponding group after blinding was removed (i.e., FFPE NL clusters with fresh NL, and FFPE EE clusters with fresh EE), resulting in indistinguishable patterns.

FIG. 5C. Representative RNA quality from FFPE tissues was shown with high purity.

FIG. 5D. Using the same 1-D reduction method as was used to calculate EoE score in fresh samples, the EoE score was determined for the 8 FFPE samples in order to compare to the algorithm developed for fresh NL and EoE samples. The 333 EoE score cut-off line is shown.

Example 9

Use of the EDP and Algorithms to Identify a Patient Population with EoE but Having a Borderline Diagnosis as Defined by Conventional Methods The traditional histological examination of the biopsy section largely depends on the number of eosinophils present in order to draw a diagnostic conclusion. Consensus recommendation of EoE experts have defined EoE as a clinicopathological disease requiring a peak eosinophil count of 15 cells in any HPF. However, in clinical practice, physicians often face a diagnostic dilemma where the patients have strong clinical symptoms for EoE with family history but have less than the diagnostic threshold of 15 eosinophils/HPF. As such, the cutoff line of 15 eosinophils has been questioned by clinicians and histologists regarding its sensitivity of diagnosing EoE. Moreover, it is possible that the infiltrating eosinophils are not evenly distributed in the distal esophagus. Even within a single biopsy, the eosinophil number can vary from locus to locus. Accordingly, the peak eosinophil number read from a single biopsy may not represent the disease status. Therefore, the number of EoE patients that were misdiagnosed for being below the 15 eosinophil cutoff line was determined by examining the molecular expression of patients with 6-14 eosinophils/HPF.

In order to clarify the percentage of potential EoE patients within this "sub-diagnosis zone," the EDP (Example 3) and the associated algorithms were utilized to evaluate the gene signature of this ambiguous borderline population. Two cohorts of pediatric patients (<21 years old) with 6-14 eosinophils/HPF were recruited; such eosinophil counts do not form an EoE diagnosis according to a recent consensus recommendation (Liacouras, C. et al. 2011. *J Allergy Clin Immunol* 128:3-20, Epub 2011 Apr. 7), which is incorporated herein by reference in its entirety). One cohort consisted of patients without a known prior EoE diagnosis/history whose previous test results had an eosinophil number of 6-14 eosinophils/HPF (6-14, n=10). The second cohort consisted of ambiguous EoE patients having an eosinophil number of 6-14 eosinophils/HPF following treatment (Remission 6-14, n=20).

The expression signatures of the aforementioned 4 cohorts were juxtaposed using the transcriptome acquired by EDP (FIG. 6A), demonstrating that patients with 6-14 eosinophils/HPF have a unique signature with up-genes modestly increased but down-genes largely unchanged. When analyzed by the $\Sigma\Delta CT$ algorithm, 30% and 50% of the initially encountered and EoE remission patient cohorts, respectively, had a positive EDP score (FIG. 6B).

After dimensionality reduction, a 3-D expression plot (summarizing the 77-D expression) suggested that the ambiguous patients with 6-14 eosinophils/HPF form a distinguishable signature in contrast to normal and EoE patients, with their Euclid distance closer to normal. In order to test whether this initial signature change could be predicative for long-term prognosis of EoE, a longitudinal study was also performed on the clinical outcomes of the remission patients with 6-14 eosinophils/HPF by tracking their medical records; this study demonstrated that 60% of these patients (based on 12 trackable cases out of 20 cases total) developed an active disease state with >15 eosinophils/HPF after the collection date.

Figure 6A:
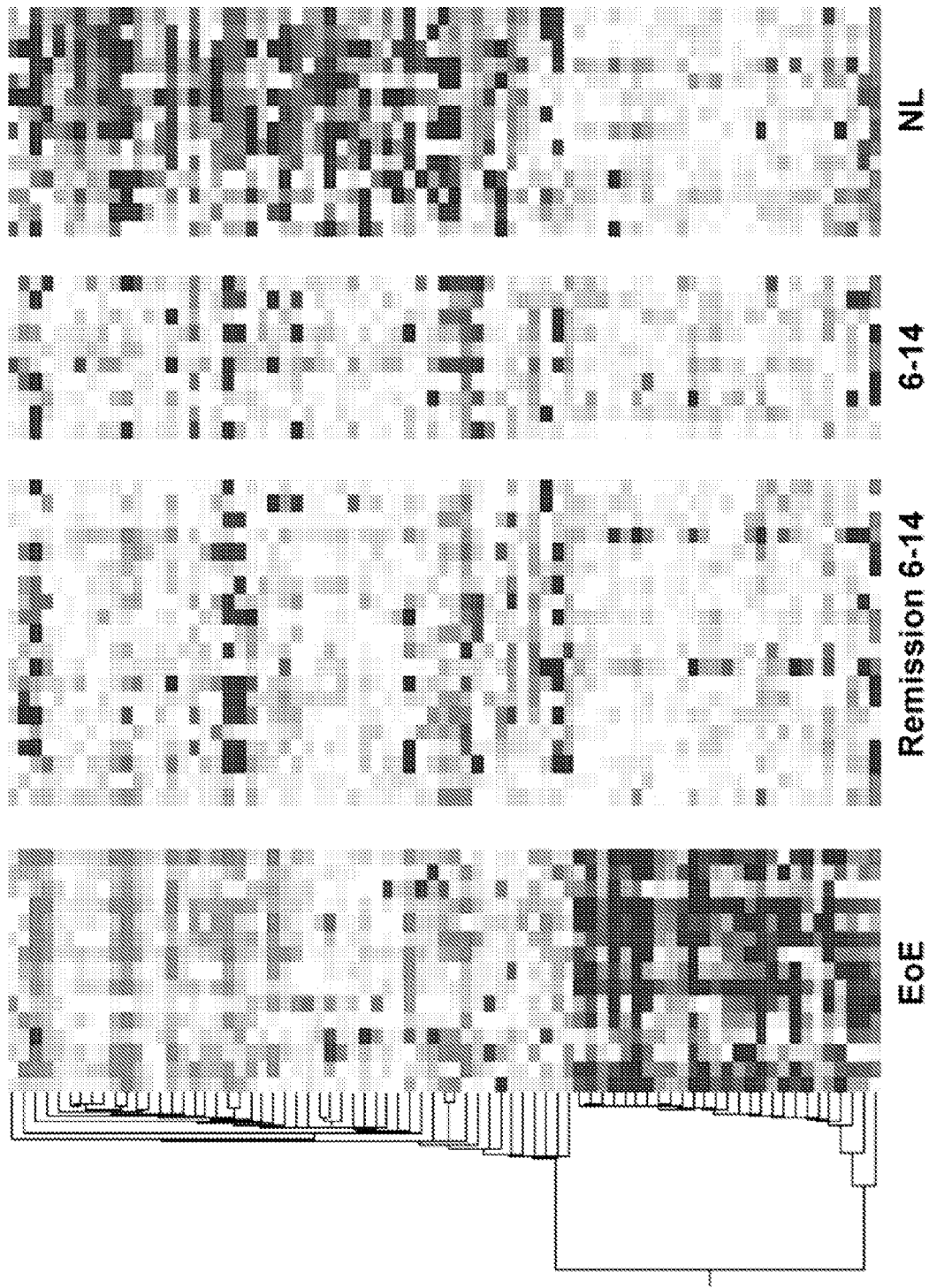
FIGS. 6A-D depict an exploration of the EoE transcriptome pattern in the ambiguous patient population with 6-14 eosinophils/HPF.
Figure 6:
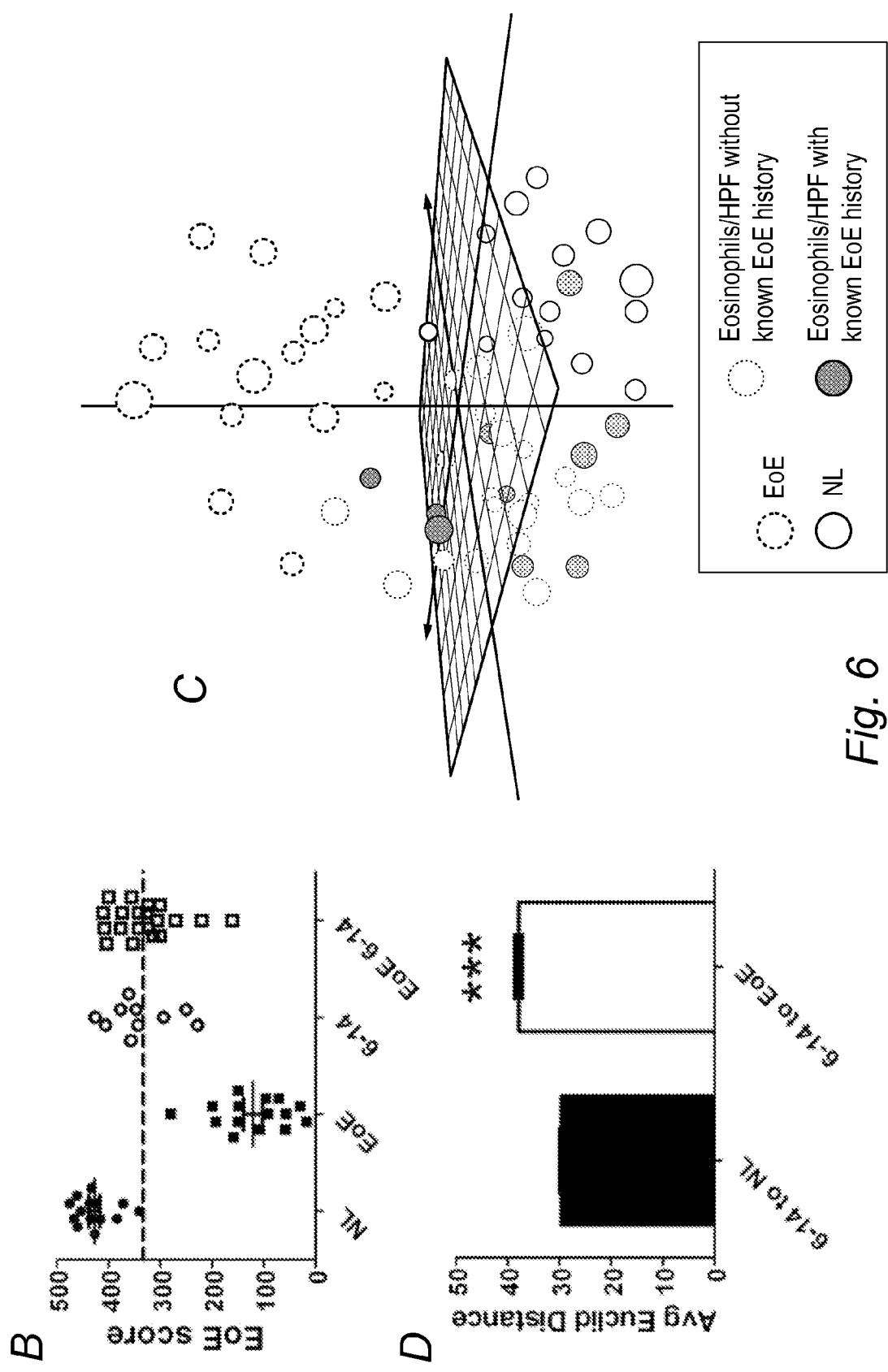

FIG. 6A. To assess the EoE signature of two cohorts of equivocal patients, namely patients with esophageal biopsies that demonstrate 6-14 eosinophils/HPF without known previous diagnosis of EoE (6-14) and EoE patients in remission with 6-14 eosinophils/HPF (Remission 6-14), EDP-based expression signatures were juxtaposed with the algorithm developing NL and EoE cohorts for visual comparison.

FIG. 6B. The $\Sigma\Delta Ct$ algorithm was utilized to assess EoE transcriptome occurrence within both ambiguous 6-14 eosinophils populations. The EoE score scatter plot indicates that 30% (3/10) and 50% (10/20) of patients indicated an EoE signature by EDP in the newly diagnosed cohort and remission cohort, respectively, by the 333 EoE diagnostic cut-off (dashed line).

FIG. 6C. Multi-dimensional scaling (MDS) analyses were carried out to visualize the expression of the 77 core EoE genes on a 3-D plot for NL, EoE, 6-14 eosinophils/HPF without known EoE history, and 6-14 eosinophils/HPF with EoE history (pink).

FIG. 6D. The average Euclid distances (permutation of all possible pairs) from both 6-14 cohorts (combined, with and without EoE history) to NL and EoE, respectively, were graphed as Mean±95% CI, revealing their collective Euclid distance to NL and EoE reference cohorts, respectively. (*** $p<0.001$)

Example 10

Comparison of the Eosinophilic Esophagitis Transcriptome Between Adult and Pediatric Samples EoE is an inflammatory condition that affects all age groups clinically. Therefore, given that all the samples being studied were pediatric, a subsequent study was designed to determine whether the adult EDP EoE transcriptome is different from that for pediatric EoE.

Figure 7A:
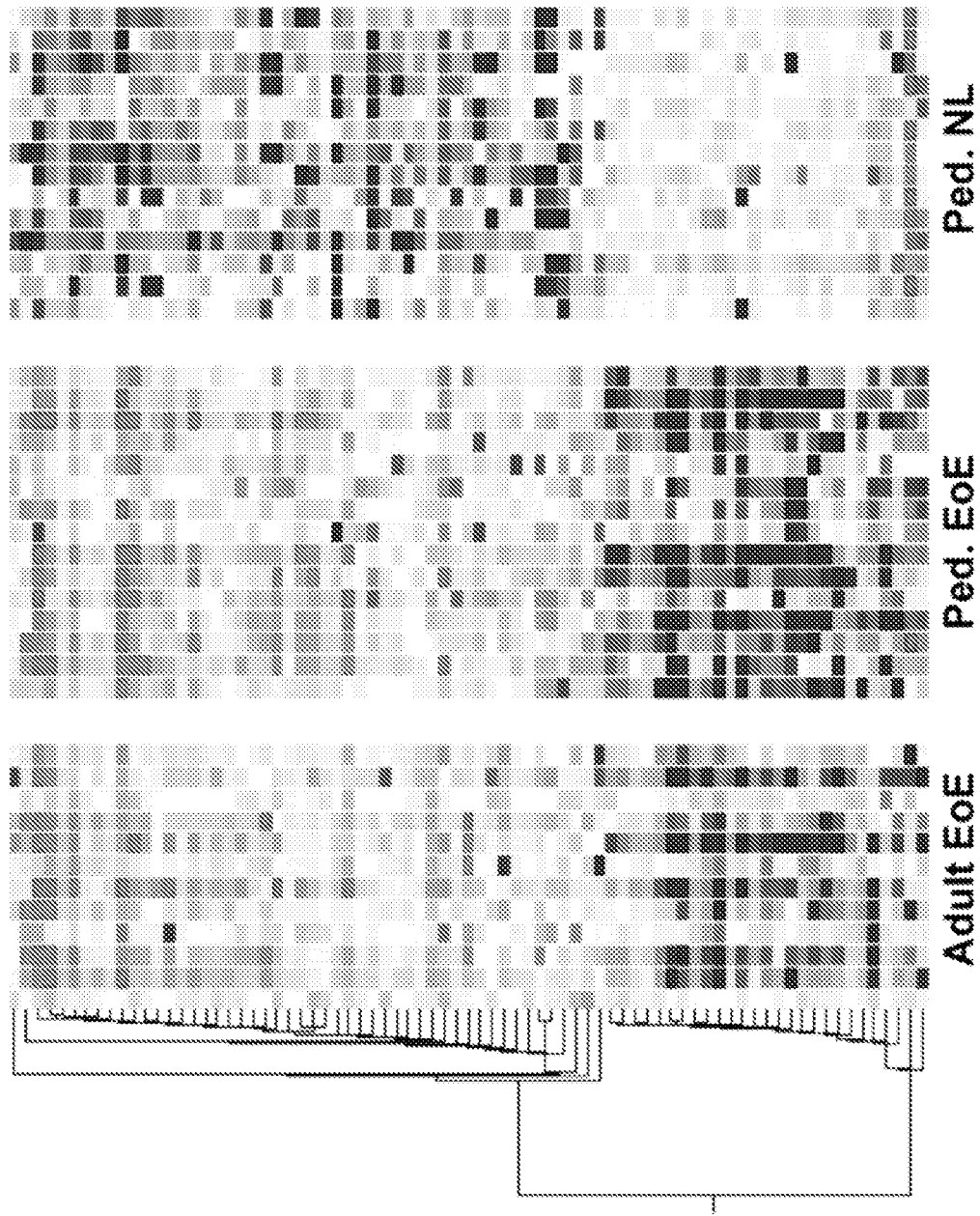
FIGS. 7A-F depict the comparable transcriptome between adult and pediatric EoE populations.
Figure 7:
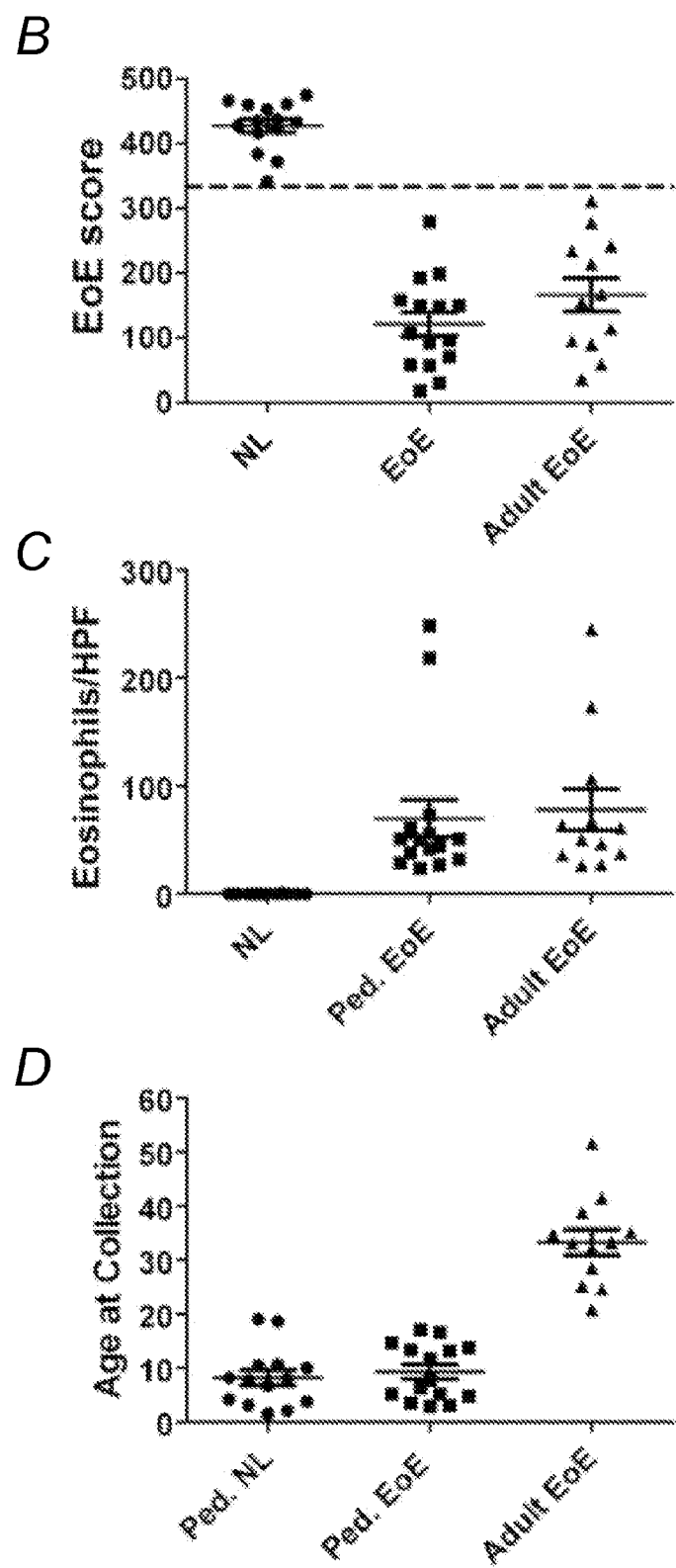

Twelve adult EoE patients were recruited with tissue eosinophil counts matched with pediatric groups (FIG. 7D); samples from these patients were then subjected to the EDP test. The 77 core gene-based expression signatures of adult EoE, pediatric EoE, and pediatric NL were compared side by side in a heat map (FIG. 7A), demonstrating a similar expression pattern between adult and pediatric onsets. After dimensionality reduction, the EoE score indicated a comparable signature between the two EoE cohorts as well (FIG. 7B). The eosinophils/HPF information and the age match for these 3 cohorts of patients were graphed in FIGS. 7C and 7D, respectively.

Figure 7E:
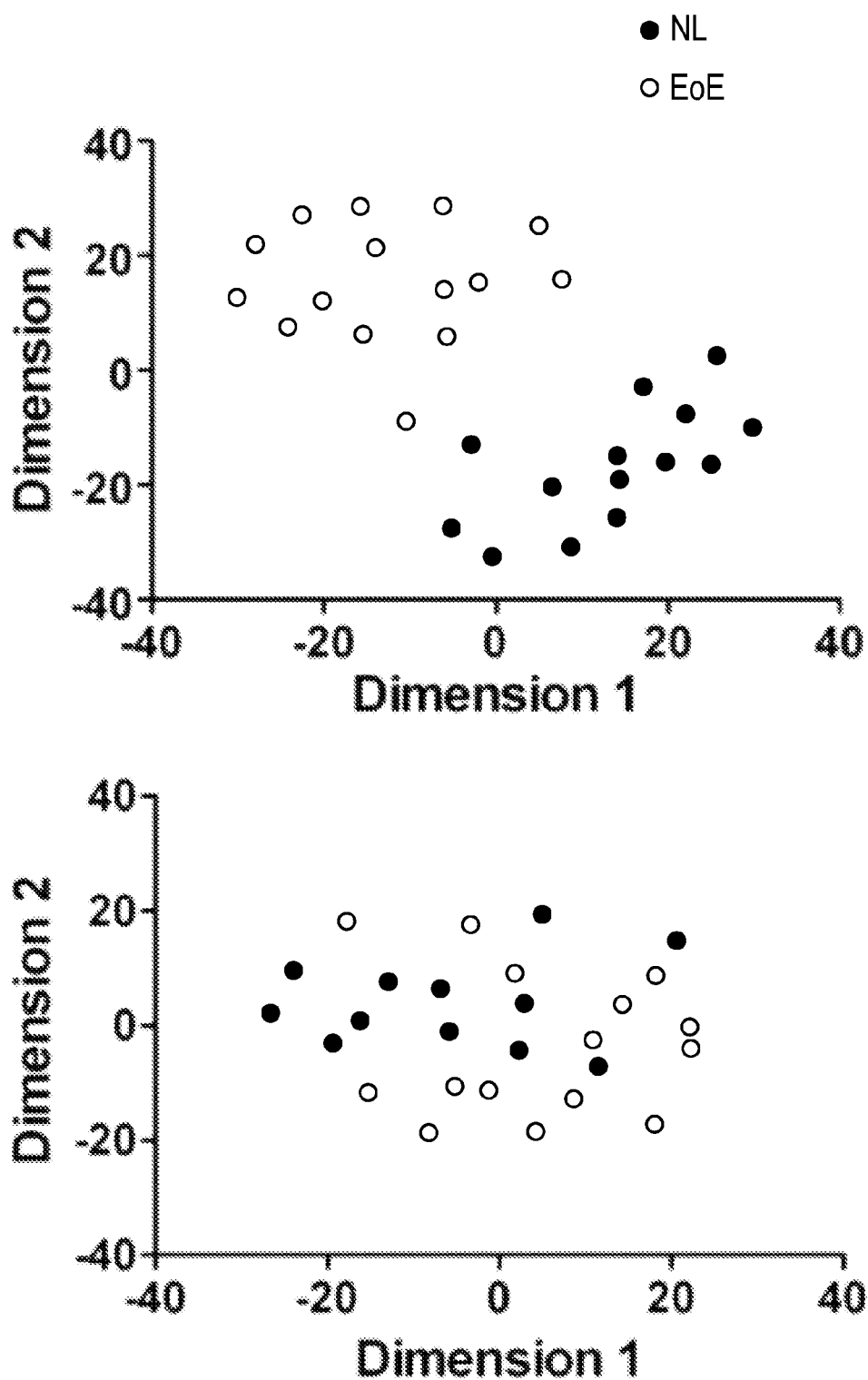

From a statistical perspective, MDS analysis showed two distinct groups when NL and pediatric EoE samples were analyzed on a 2-D plot, indicating a large Euclid distance (FIG. 7E, upper panel). In contrast, on the same scale, 2-D MDS analysis resulted in a co-mingled result between pediatric and adult EoE patients (FIG. 7E, lower panel).

Figure 7F:
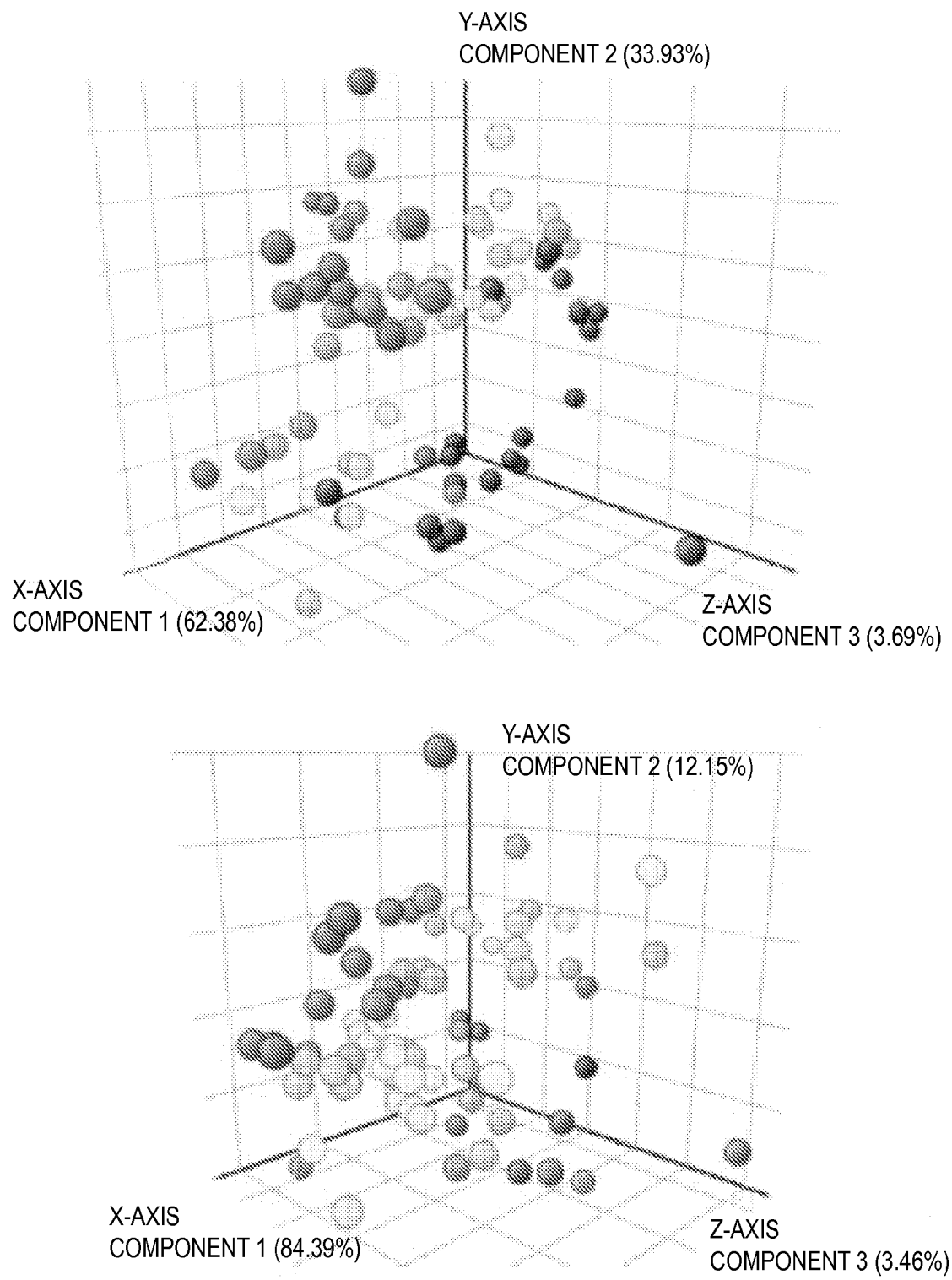

In order to further demonstrate the similarities between adult EoE and pediatric EoE, the principle component analysis (PCA) was performed on the 77 core EoE genes to address their contribution in distinguishing NL vs. pediatric EoE (FIG. 7F, upper panel) and pediatric EoE vs. adult EoE (FIG. 7F, lower panel). In the FIG. 7F PCA plots, the first 3 major components contributing to the variance of total samples compared were graphed on a 3-D plot heated on fold change. Similar results were observed on the MDS plot when NL was compared to pediatric EoE. The Y-component on the PCA 3-D plot largely reflects EoE "up and down" signature; however, no such trend on the Y-axis was readily observed when pediatric EoE were compared to adult ones.

FIG. 7A. Molecular expression heatmaps from 12 eosinophilia-matched adult active EoE patients were acquired via the EDP and juxtaposed to the heatmaps of the algorithm developed for pediatric EoE and pediatric NL cohorts for expression signature comparison.

FIG. 7B. EoE scores were calculated for adult EoE and pediatric EoE cohorts, along with a pediatric NL cohort, to compare the EoE signature in 1-D quantification.

FIG. 7C. Eosinophils/HPF were graphed for all 3 groups to show the eosinophilia match in the two active EoE cohorts.

FIG. 7D. The age distribution chart for all 3 groups analyzed herein.

FIG. 7E. The upper panel depicts the expression profiles of the 77 core EoE genes from pediatric EoE and NL cohorts as reduced to 2-D visualization by MDS analysis, with distance between two given points reflecting expression difference in 2-D space (Euclidean metric). The lower panel depicts the MDS analysis performed between adult EoE and pediatric EoE, with 2-D data plotted on the same scale.

FIG. 7F. The upper panel depicts expression of the 77 core EoE genes as analyzed by PCA to examine if the unique EoE dysregulation pattern is present between pediatric EoE and NL, and the top 3 components were graphed in 3-D space (heated by fold change), with the Y-axis component reflecting the direction of dsyregulation. Lower panel: PCA analysis was performed between adult EoE and pediatric EoE on the expression profile of the 77 genes with no comparably-strong component readily observed.

Example 11

A Retrospective Impedance-Based Case Study for Differentiating Between Eosinophilic Esophagitis and GERD In order to demonstrate the true capacity of the EDP to differentiate EoE from GERD and further validate the FFPE compatibility, a population of 43 patients with upper GI symptoms who underwent both EGD and esophageal impedance analysis was acquired. The endoscopic biopsy sampling was done within the same year as impedance measurement (with a mean of X+/−months). The retrospective nature of this sub-study required that the EDP was performed on archived FFPE samples.

Figure 8A:
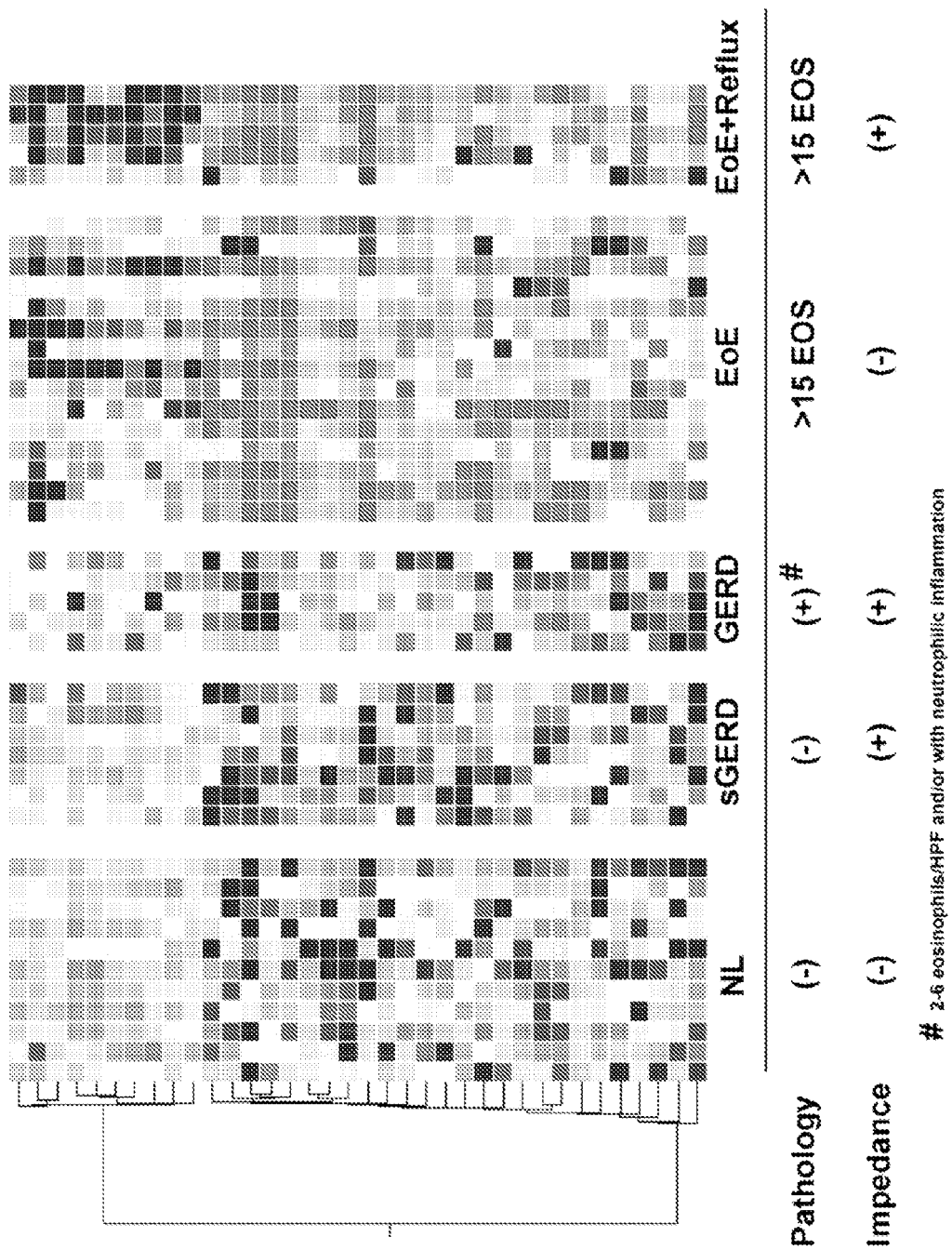
FIGS. 8A-B depict an impedance-guided EDP analysis aiming to discriminate GERD from EoE.

The 43 patients were divided into 5 different study cohorts based on their histological report and concurrent esophageal pH probe data, as illustrated in FIG. 8A; the 5 cohorts identified were normal (NL, normal pathology, normal impedance), symptomatic GERD (sGERD, normal pathology, abnormal impedance), GERD (abnormal pathology, specifically 2-6 eosinophils/HPF with inflammatory infiltrate, abnormal impedance), EoE (>15 eosinophils/HPF, normal impedance), and EoE+Reflux (>15 eosinophils/HPF, abnormal impedance). The abnormal pathology in GERD includes pathological inflammatory infiltration (<5 eosinophils/HPF, no EoE history). Statistical screening (FDR-corrected p<0.05, fold change >2) between NL and EoE was performed to identify core EoE genes in this sub-study, which yielded 44 FFPE significant genes.

Figure 8B:
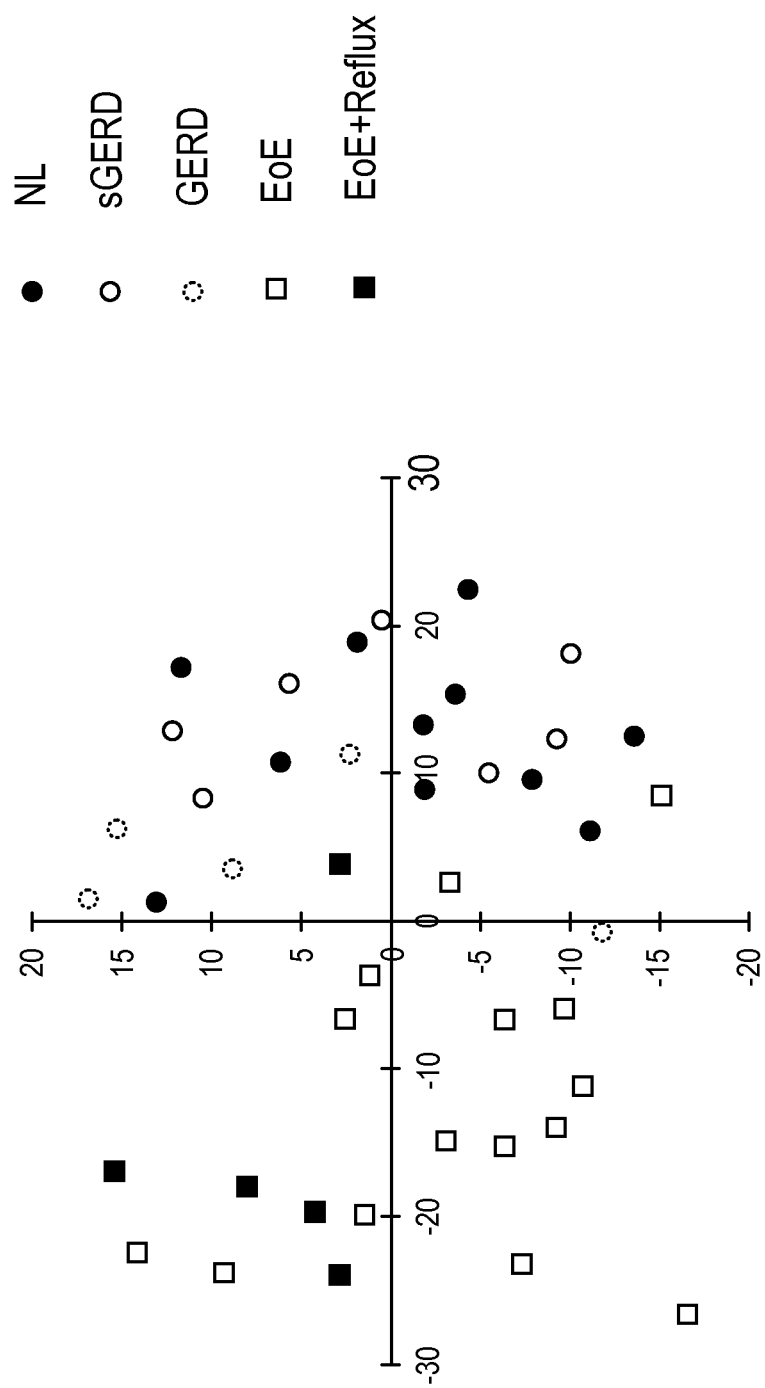

An expression heapmap was juxtaposed based on these 44 genes and patient grouping conditions (FIG. 8A). As indicated on the figure, normal and pure EoE formed two distinct heat patterns with bi-directional dysregulation. The symptomatic GERD group was highly comparable to normal controls, and the expression pattern of the pathological GERD group looked largely similar to normal. Additionally, EoE+Reflux patients exhibited a typical EoE signature as defined by the EoE group. From a 2-D perspective, MDS analysis was also performed to position all 43 patients in 5 groups in relevance to their Euclid distance matrix (FIG. 8B). Generally inspecting, two populations oppose each other at the frontline of 5 o'clock to 11 o'clock, with the NL, sGERD, and GERD cohorts in quadrants I-IV and the EoE and EoE+Reflux cohortsin quadrants II-III.

FIG. 8A. The EDP was performed on a selected cohort of 43 patients with impedance results at the time of endoscope procedure, who were categorized into 5 different cohorts based on pathology findings and impedance test. An expression heatmap was generated based on 44 significant genes after a statistical screening between NL and EoE resulted in (FDR corrected p<0.05, fold change >2.0). Five study cohorts, namely normal (NL), symptomatic GERD (sGERD), GERD, EoE, and EoE plus gastroesophageal reflux (EoE+Reflux) were juxtaposed for visual comparison.

FIG. 8B. The above 44 gene expression profiles of the five categories of patients were subject to MDS analysis to reveal their 2-D-simulated Euclid distance of all 44 genes. The EDP was performed on FFPE-derived RNA in this retrospective study.

Example 12

Replication Study for the Overall Assessment of the Merit of the EDP

The diagnostic merits of the EDP were then evaluated by examining the transcription signatures from 166 fresh RNA samples encountered at CCHMC. Among the 166 patients, 132 had eosinophils/HPF <2 or >15, forming the NL and EoE pool to be diagnosed.

Figure 9A:
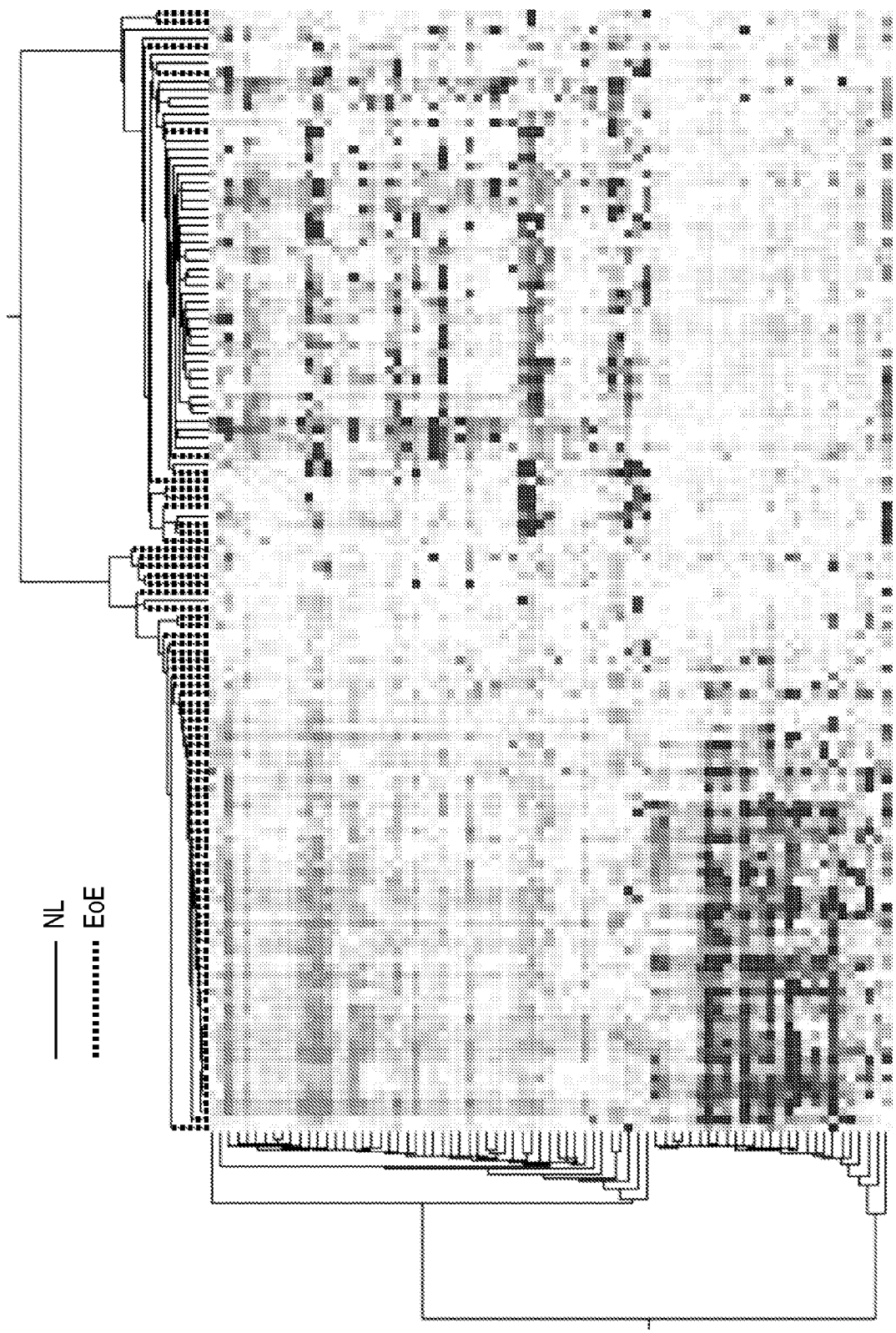
FIGS. 9A-D depict an overall assessment of EDP merit with a clinical practice with incoming by collecting an EDP signature on a total of 166 patients, consisting of 83 EoE (>15 EOS) and 50 NL (<2 EOS) by histology.
Figure 9:
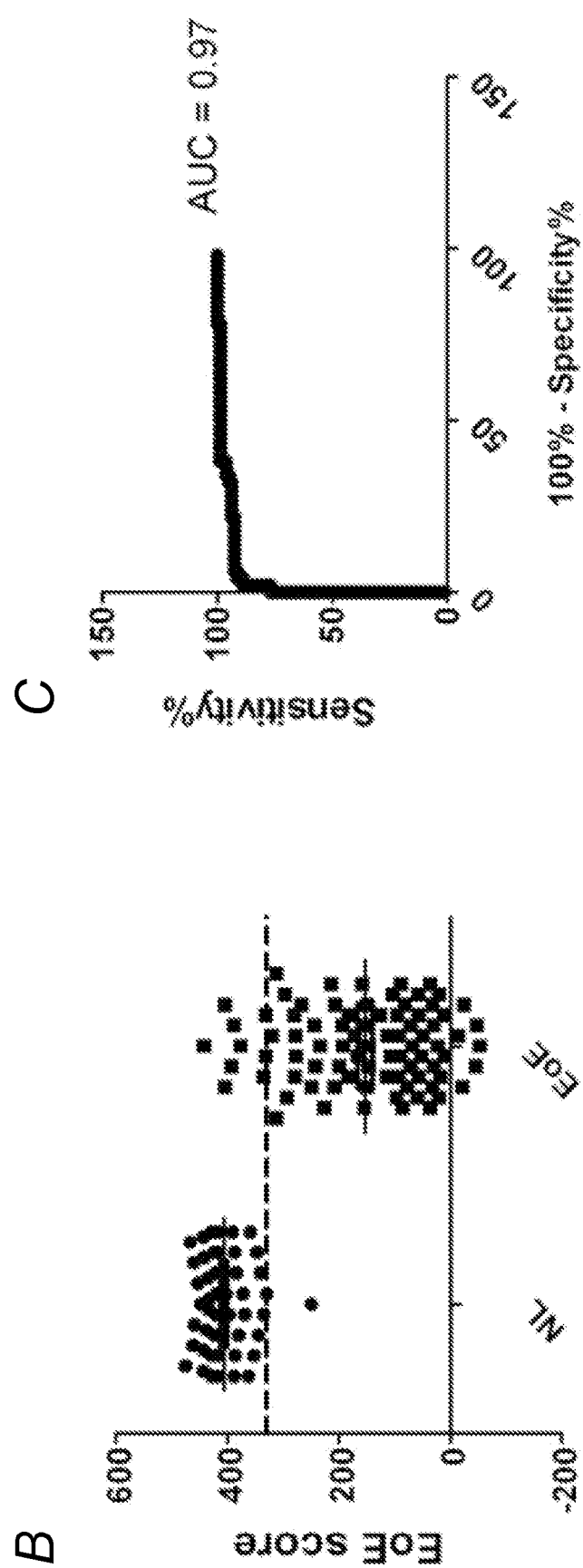

Performing the clustering analysis on the 77 core EoE genes derived from the algorithm indicated the presence of two distinct cohorts, namely the EoE transcriptome and the NL transcriptome (FIG. 9A). Under the first degree dendrogram, the uniformity of tree color represents diagnostic merits.

The EoE score was then calculated based on the differential expression of the 77 core EoE genes (FIG. 9B). Using ROC cut-off optimization, the EoE score=333 cut-off used throughout all experiments was derived (FIG. 9C), which demonstrated an excellent coverage between sensitivity and specificity (FIG. 9D) of the EDP test, with an ultra-high area under curve (AUC) of 0.97 (FIG. 9D).

FIG. 9A. To assess the dual algorithms of the EDP at larger scale, EDP signatures were collected on a total of 166 patients, which consist 83 EoE (>15 EOS) and 50 NL (<2 EOS) by histology. With the clustering algorithm by first branch, a double clustered heat map was generated, indicating that the EDP clustering algorithm is highly competent at EoE prediction (PPV advantage), with only one NL misdiagnosed as EoE (single blue line in the EoE cluster), at the cost of reduced NPV values.

FIG. 9B. EoE scores from histology-definded 50 NL and 82 EoE patients were plotted over the 333 diagnostic cut-off, resulting in an optimized balance between sensitivity and specificity.

FIG. 9C. A ROC curve with the diagnostic cutoff line of EoE R score=333 is depicted.

FIG. 9D. Based on the EoE score analysis in FIG. 9C, the EDP diagnostic merit was summarized in specificity vs. sensitivity and PPV vs. NPV, reflecting the EDP diagnostic power in clinical practice.

Example 13

Diagnosis of a Patient for Eosinophilic Esophagitis

The EoE gene transcriptome (Blanchard, et al. *J. Clin. Invest.* 116:536-47 (2006)) identified a molecular signature that readily distinguished EoE patients from control individuals (normal patients and patients with other forms of chronic esophagitis) and has provided a promising diagnostic foundation for EoE, as molecular analysis will provide a shorter turn-around time, reduced diagnostic cost, higher sensitivity/specificity, and relatively better objectivity and consistency compared with manual microscopic analysis. Furthermore, it has the capacity to reduce the overall number of biopsy samples required for diagnosis and reveal EoE pathogenesis that could vary from patient to patient, forming the basis for the practice of personal medicine.

As described herein, a dual set of algorithms was used to visualize and quantify EoE transcriptional signature for diagnostic purposes. The EDP demonstrated markedly discernible molecular gene expression differences between EoE and NL patients and pH-confirmed GERD patients. The traditional histological examination of the biopsy section largely depends on drawing a diagnostic conclusion based on the number of eosinophils present in the sample. The consensus recommendation of EoE experts has defined EoE as a clinico-pathological disease requiring a peak eosinophil count of 15 cells in any HPF (Furuta, et al. *Gastroenterology* 133:1342-63 (2007)). However, in clinical practice, physicians often face a diagnostic dilemma where the patients have strong clinical symptoms for EoE and have less than 15 eosinophils/HPF. As such, the cutoff line of 15 eosinophils/HPF has been questioned by clinicians and histologists regarding its sensitivity for diagnosing EoE. Moreover, it is conceivable that the infiltrating eosinophils are not evenly distributed in the esophageal mucosa. Even within one biopsy, the eosinophil number varies from locus to locus. Therefore, the peak eosinophil number read from one biopsy might not represent the disease status.

As described herein, studies were designed to determine how many EoE patients were perhaps mislabeled using the 15 eosinophil cutoff (by examining the molecular expression of patients with 6-14 eosinophils). Both the dual algorithms indicated that there were 30-50% patients within the 6-14 eosinophils/HPF population that resemble active EoE patients. A similar percentage of positive cases and a similar signature between the newly recruited and remission patients with 6-14 eosinophils were observed. As the up-genes are increased earlier than the down-regulated genes, the unique signature of 6-14 eosinophils/HPF patients can represent a transitioning or intermediate disease status. Sixty percent of these remission 6-14 eosinophils/HPF remission patients developed active EoE (>15 eosinophils/HPF) later, further supporting this finding and demonstrating the potential of using the EDP for personal medicine. Clinicians should note this non-negligible percentage of patients who do not meet the CR 2007 diagnosis criteria while exhibiting an EoE gene expression pattern, who can thus more likely represent EoE from a clinical follow-up point of view. These data are consistent with the recent finding that long-term consequences of esophageal eosinophilia emerge at eosinophils levels >5/HPF (DeBrosse, et al. *J. Allergy Clin. Immunol.* 126:112-9 (2010)) and another study showing that up to 50% of equivocal cases are truly EoE.

EoE is a morbidity affecting all age groups. Since some reports suggested adult and pediatric cases have different clinical manifestations (Straumann, et al. *Allergy* 67:477-90 (2011), Epub 2012 Feb. 8), symptomatic variation can be due to a disparate pathogenesis or different interpretation of esophageal pathology between adult and children. As described herein, adult EoE patients share the same transcriptome as pediatric ones, suggesting that the clinically observed difference may be due to functional interpretation and social-environmental compounding factors in children vs. adults, rather than a different pathological pathway. Moreover, these data also support the application of EDP diagnosis in adult populations, since the existing algorithms were all validated as well.

The diagnostic method is carried out on a patient to determine if the patient has eosinophilic esophatigis (EoE). RNA extraction is performed on a patient esophageal biopsy tissue sample. After RNA quantity/quality measurement by nanodrop, 1000 ng of the RNA sample is measured for the reverse transcription (RT) reaction. cDNA corresponding to 500 ng RNA is mixed with a qPCR amplification cocktail (such as, for example, Taqman Master Mix) and loaded onto the 384 well fluidic card (4 patients per 384 well card with 96 genes per patient). The cDNA is amplified with a real-time qPCR system (e.g. ABI 7900 HT system). The analysis step is performed in qPCR analysis software (e.g. Genespring software), and the qPCR raw data is subjected to the dendogram and/or EoE scoring algorithms as disclosed herein, or other algorithms, or other analysis of the results to obtain relatedness information relative to an EoE cohort, in order to establish an EoE diagnosis, which serves as the basis for the final diagnostic report.

Example 14

Diagnosis of a Patient for EoE

As Distinguished from Other Esophageal Disorders

In addition to GERD, there are more than 10 other clinical diseases that are also associated with esophageal eosinophilia (Liacouras, et al. *J. Allergy Clin. Immunol.* 128:3-20 (2011)), whose clinical symptoms do not always provide consistent and reliable clues for differential diagnosis. The EoE transcriptome essentially represents a comprehensive adaptation of the esophageal epithelium to the immunological challenges initiated by allergens; therefore, use of the EDP will provide a significantly improved EoE differential diagnosis given the unique gene expression profile of this disease. Although tentative treatment (e.g. proton-pump inhibitors, or PPIs) can also differentiate between EoE and GERD to certain degree, there are certain exceptions (Molina-Infante, et al. *World J. Gastroenterol.* 13:1463-6 (2008)), requiring a much longer time and resulting in sub-optimal diagnostic and treatment timing hence negatively affecting the quality of life for EoE patients.

As described herein, the molecular signature of normal and EoE patients was acquired, which forms a solid and consistent basis for differential diagnosis. Since GERD is the clinician's primary concern regarding EoE differential diagnosis (Furuta, et al. *Gastroenterology* 133:1342-63 (2007); Molina-Infante, et al. *World J. Gastroenterol.* 13:1463-6 (2008)), a retrospective study was designed using multiple impedance-guided patient cohorts to demonstrate that esophageal eosinophilia in GERD patients can be well-distinguished from esophageal eosinophilia due to EoE. In additional to differentiation between GERD and EoE, this sub-study also can provide clinicians with multiple lines of information regarding the diagnosis and treatment of upper GI morbidity.

The diagnostic method is carried out on a patient to determine if the patient has eosinophilic esophatigis (EoE) instead of other esophageal disorders, such as gastroesophageal reflux disease (GERD). RNA extraction is performed on a patient esophageal biopsy tissue sample. After RNA quantity/quality measurement by nanodrop, 1000 ng of the RNA sample is measured for the reverse transcription (RT) reaction. cDNA corresponding to 500 ng RNA is mixed with a qPCR amplification cocktail (such as, for example, Taqman Master Mix) and loaded onto the 384 well fluidic card (4 patients per 384 well card with 96 genes per patient). The cDNA is amplified with a real-time qPCR system (e.g. ABI 7900 HT system). The analysis step is performed in qPCR analysis software (e.g. Genespring software), and the qPCR raw data is subjected to the dendogram and/or EoE scoring algorithms as disclosed herein, or other algorithms, or other analysis of the results to obtain relatedness information relative to an EoE cohort, in order to establish an EoE diagnosis, which serves as the basis for the final diagnostic report.

Example 15

Diagnosis of a Patient for Esophageal Eosinophilia Associated with Other Gastrointestinal Disorders A patient can experience EoE in association with other eosinophilic gastrointestinal disorders (EGIDs), which can be outside of the esophagus. For example, a patient having another gastrointestinal (GI) disorder, such as, for example, eosinophilic colitis, or the like, can also have esophageal eosinophilia. The other GI disorder can be, for example, an eosinophilic GI disorder (EGID) or an inflammatory GI disorder, such as celiac disease, inflammatory bowel disease, and the like. The esophageal eosinophilia can occur refractory to PPI therapy. Such a condition can be termed eosinophilic gastroenteritis (EG). The EDP can diagnose "EoE" in such a patient.

The diagnostic method is carried out on a patient to determine if the patient has eosinophilic esophatigis (EoE) in association with other gastrointestinal disorders. RNA extraction is performed on a patient esophageal biopsy tissue sample. After RNA quantity/quality measurement by nanodrop, 1000 ng of the RNA sample is measured for the reverse transcription (RT) reaction. cDNA corresponding to 500 ng RNA is mixed with a qPCR amplification cocktail (such as, for example, Taqman Master Mix) and loaded onto the 384 well fluidic card (4 patients per 384 well card with 96 genes per patient). The cDNA is amplified with a real-time qPCR system (e.g. ABI 7900 HT system). The analysis step is performed in qPCR analysis software (e.g. Genespring software), and the qPCR raw data is subjected to the dendogram and/or EoE scoring algorithms as disclosed herein, or other algorithms, or other analysis of the results to obtain relatedness information relative to an EoE cohort, in order to establish an EoE diagnosis, which serves as the basis for the final diagnostic report.

Example 16

Diagnosis of a Patient for Remission from Eosinophilic Esophagitis

Remission from active EoE disease is commonly observed clinically following a variety of factors. Even though the esophagus eosinophil number can drop to zero, the patient can continue to be at high risk to relapse when environmental factors are re-engaged. Remission from active EoE can be induced by a variety of treatments, including steroid- and diet-induced reversal (Straumann, et al. *Gastroenterology* 139:1526-37 (2010); Chehade, et al. *Curr. Opin. Allergy Clin. Immunol.* 10:231-7 (2010)). However, even though the esophageal eosinophil number may normalize, the patient is still at high risk to relapse when environmental factors change (Straumann, et al. *Clin. Gastroenterol. Hepatol.* 9:400-9 (2011); Lucendo, et al. *Dig. Dis. Sci.* 56:3551-8 (2011)). Previous mRNA microarray studies have indicated that there is a particular cohort of genes remaining dysregulated in EoE remission patients (patients who responded to fluticasone with complete normalization of esophageal eosinophilia) compared to NL; meanwhile, there is another gene cohort responding to glucocorticoid exposure serving as the usage markers (Blanchard, et al. *J. Allergy Clin. Immunol.* 120:1292-300 (2007)).

When analyzing specific gene sets on the 96A panel, topical steroid-induced EoE remission samples were readily differentiated from NL samples by either the cluster analysis or the $\Sigma\Delta CT$ algorithms described herein (Example 7). The potential clinical significance of this is multi-fold. First, subjective steroid usage/compliance can be objectively predicted with steroid responding biomarkers, such as FKBP51 (Caldwell, et al. *J. Allergy Clin. Immunol.* 120:1292-300 (2007)). Secondly, in clinical practice, physicians need to differentiate EoE remission from NL patients because their therapy, prognosis, and follow-up plans are quite different, and the conventional histological examination cannot perform this type of discrimination due to the dependence on eosinophil numbers to provide diagnostic insight.

Depending on distinct gene clusters used on the EDP, the EoE remission cohort showed a pronounced difference compared to NL and no difference compared to active EoE with the remission scoring system (22 genes); in terms of the EoE scoring system (77 genes), the EoE remission cohort does not differ from NL but differs significantly from active EoE.

EoE remission is therefore an intermediate status in between active EoE and NL and is distinguishable from both EoE and NL depending on the gene set usage on the panel. Certain top EoE upregulated genes remain highly dysregulated in EoE remission patients, such as the top EoE genes CCL26 and CDH26, suggesting that the molecular-pathological drive is still partially present during remission, rendering the patient susceptible to another allergic attack in the absence of steroid therapy and likely contributing to relapse propensity (Sprenger, et al. Neth. J. Med. 67:8-12 (2009)).

The diagnostic method is carried out on a patient to determine if a patient has entered remission of eosinophilic esophatigis (EoE). RNA extraction is performed on a patient esophageal biopsy tissue sample. After RNA quantity/quality measurement by nanodrop, 1000 ng of the RNA sample is measured for the reverse transcription (RT) reaction. cDNA corresponding to 500 ng RNA is mixed with a qPCR amplification cocktail (such as, for example, Taqman Master Mix) and loaded onto the 384 well fluidic card (4 patients per 384 well card with 96 genes per patient). The cDNA is amplified with a real-time qPCR system (e.g. ABI 7900 HT system). The analysis step is performed in qPCR analysis software (e.g. Genespring software), and the qPCR raw data is subjected to the dendogram and/or EoE scoring algorithms as disclosed herein, or other algorithms, or other analysis of the results to obtain relatedness information relative to an EoE cohort, in order to establish an EoE diagnosis, which serves as the basis for the final diagnostic report.

Example 17

Determination of a Patient's Degree of Tissue Fibrosis and/or Remodeling

One of the major advantages of the EDP over the histological examination is the potential to rapidly understand the molecular pathogenesis of individual patients. The EDP, being highly representative of the whole EoE transcriptome, can greatly facilitate expression correlation studies and reveal new pathogenic pathways at effective but affordable costs compared to regular genome-wide screening. In terms of the expression pattern of the 94 genes, there was some variation within the EoE cohort (e.g. IL-4 levels), which can account for the distinct pathogenesis for individual patients. Accordingly, the differentiated $T_H2$ cell markers (IL5, IL4, and IL13) and mast cell markers (tryptase, carboxypeptidase A3, and chymase, or TPSB2;TPSAB1, CPA3, CMA1, respectively) have been incorporated on the EDP, and their expression is significantly increased.

Fibrosis is one of the features of EoE which significantly affect the life quality of EoE patient. Collagen and keratin formation mirror fibrosis in patients and can therefore be used to study fibrosis and tissue remodeling. Genes associated with keratin and collagen have been incorporated into the EDP, allowing the EDP to be used to study tissue pathogenesis and the involvement of these factors with disease progression and disease status.

As described herein, keratin 23 (KRT23), collagen 1A2 (COL1A2), and collagen 8A2 (COL8A2) were used as the markers for esophageal fibrosis, and both are shown to be significantly upregulated in EoE biopsies. This finding has the potential to influence treatment, as a better understanding of gene significance and specific therapy can be developed. The degree of fibrosis can be related to EoE or to another condition.

The diagnostic method is carried out on a patient to determine the involvement of fibrosis with the patient's condition and to determine patient's degree of fibrosis and/or tissue remodeling. RNA extraction is performed on a patient esophageal biopsy tissue sample. After RNA quantity/quality measurement by nanodrop, 1000 ng of the RNA sample is measured for the reverse transcription (RT) reaction. cDNA corresponding to 500 ng RNA is mixed with a qPCR amplification cocktail (such as, for example, Taqman Master Mix) and loaded onto the 384 well fluidic card (4 patients per 384 well card with 96 genes per patient). The cDNA is amplified with a real-time qPCR system (e.g. ABI 7900 HT system). The analysis step is performed in qPCR analysis software (e.g. Genespring software), and the qPCR raw data is subjected to the dendogram and/or EoE scoring algorithms as disclosed herein, or other algorithms, or other analysis of the results to obtain relatedness information relative to an EoE cohort. Alternatively, the qPCR raw data is evaluated by obtaining relatedness information relative to a normal patient cohort. The KRT23, COL1A2, and COL8A2 genes are identified from the result set and evaluated further in order to determine the involvement of tissue fibrosis and/or remodeling with EoE or to determine the patient's degree of tissue fibrosis and/or remodeling.

The patient is re-evaluated with the diagnostic method following a period of treatment. The treatment can be a therapy that targets at least one of the KRT23, COL1A2, and COL8A2 genes. The KRT23, COL1A2, and COL8A2 genes are identified from the result set and evaluated further in order to determine any changes in the patient's degree of fibrosis and/or tissue remodeling. Such information is then used to determine disease progression and to adjust medication dosage and treatment protocol accordingly.

Example 18

Determination of Disease Progression by Monitoring Involvement of Various Cell Types Development of the EDP allowed for the determination of the functions of the genes on the panel. A number of genes were found to be associated with different cell types (see Table 1). For example, as described in Example 17 and as shown in Table 1, the genes TPSB2;TPSAB1, CPA3, and CMA1 were found to be associated with mast cells, the genes FCGR3B;FCGR3A, SLAMF7, and NCAM1 were found to be associated with natural killer (NK) cells, and the genes IL4, IL5, and IL13 were found to be associated with $T_H2$ cells, or T lymphocytes. Mast cells are associated with mastocytosis. Therefore, the EDP can be used to determine the involvement of these cells with EoE or with another condition, in addition to being used to determine the patient's degree of mastocytosis. Involvement with a condition can include an elevated level of production and/or abnormal function.

The diagnostic method is carried out on a patient to determine the involvement of mast cells and/or NK cells and/or T lymphocytes with the patient's condition and/or to determine the patient's degree of mastocytosis. RNA extraction is performed on a patient esophageal biopsy tissue sample. After RNA quantity/quality measurement by nanodrop, 1000 ng of the RNA sample is measured for the reverse transcription (RT) reaction. cDNA corresponding to 500 ng RNA is mixed with a qPCR amplification cocktail (such as, for example, Taqman Master Mix) and loaded onto the 384 well fluidic card (4 patients per 384 well card with 96 genes per patient). The cDNA is amplified with a real-time qPCR system (e.g. ABI 7900 HT system). The analysis step is performed in qPCR analysis software (e.g. Genespring software), and the qPCR raw data is subjected to the dendogram and/or EoE scoring algorithms as disclosed herein, or other algorithms, or other analysis of the results to obtain relatedness information relative to an EoE or a normal cohort. Alternatively, the qPCR raw data is evaluated by obtaining relatedness information relative to a normal patient cohort. The TPSB2;TPSAB1, CPA3, CMA1, FCGR3B;FCGR3A, SLAMF7, NCAM1, IL4, IL5, and IL13 genes are identified from the result set and evaluated further in order to determine the involvement of mast cells and/or NK cells and/or T lymphocytes with the patient's condition and/or determine the patient's degree of mastocytosis.

A patient with an elevated mast cell-related transcriptome, e.g., elevated levels of TPSB2;TPSAB1, CPA3, and/or CMA1, is treated with one or more anti-mast cell therapy. The anti-mast cell therapy can be a therapy that targets at least one of the TPSB2;TPSAB1, CPA3, and CMA1 genes. A patient with an elevated NK cell-related transcriptome, e.g., elevated levels of FCGR3B;FCGR3A, SLAMF7, and/or NCAM1, is treated with one or more anti-NK cell therapy. The anti-NK cell therapy can be a therapy that targets at least one of the FCGR3B;FCGR3A, SLAMF7, and NCAM1 genes. A patient with an elevated T lymphocyte-related transcriptome, e.g., elevated levels of IL4, IL5, and/or IL13, is treated with one or more anti-T lymphocyte therapy. The anti-T lymphocyte therapy can be a therapy that targets at least one of the IL4, IL5, and IL13 genes.

The patient is re-evaluated with the diagnostic method following a period of treatment. The TPSB2;TPSAB1, CPA3, CMA1, FCGR3B;FCGR3A, SLAMF7, NCAM1, IL4, IL5, and IL13 genes are identified from the result set and evaluated further in order to determine any changes in the involvement of mast cells and/or NK cells and/or T lymphocytes with the patient's condition and/or determine the patient's degree of mastocytosis. Such information is then used to determine disease progression and to adjust medication dosage and treatment protocol accordingly.

The EDP can therefore also be used to determine the involvement of specific types of cells with EoE or with one or more other condition. Genes of the EDP are correlated with at least one specific cell type, and a patient is evaluated using the diagnostic method to determine the involvement of the at least one specific cell type with the patient's condition.

Example 19

Evaluation of a Patient to Provide a Prognosis and Guidance on Selection and Modification of Eosinophilic Esophagitis Medication Dosage and Treatment Protocols With an EDP analysis on 132 NL (50) and EoE (82) patients, the EoE score (ΣΔCT) algorithm achieved the high ~96% specificity and ~92% sensitivity, superior to the published single-gene-based diagnostic methods (Blanchard, et al. *J. Allergy Clin. Immunol.* 127:208-17 (2011)). To prevent false positives, the clustering algorithm can be used, as it emphasizes specificity (98%) yet with acceptable sensitivity (83%).

The 15 eosinophils/HPF cut-off itself is debatable, due to the variability of counting and shared eosinophilia with non-EoE diseases. As such, redefining EoE using a molecular pathology perspective in addition to histology and clinical symptoms can provide better characterization of this disorder relative to other eosinophilic GI diseases.

In the larger-scale evaluation of the EDP test with 50 NL and 82 EoE pathology-defined patients, the EDP was highly predictive for EoE (high PPV >97%), i.e. patients are highly likely to be positive for EoE once the EDP shows bi-directional dysregulation. The sensitivity was 91.4% and the specificity was 96%.

The EDP can therefore be used as a personal medicine prediction device. Based on the molecular profile for each EoE patient, personalized medicine can be performed to enhance treatment efficiency. The EDP can be used as an accurate, rapid, informative, and low-cost diagnosis based on the EoE transcriptome and can be used alone or in conjunction with an eosinophil number-based histological diagnosis and an empirical eosinophilia cutoff line.

A molecular understanding of the pathogenesis of EoE can not only aid the diagnosis dilemma (Example 12), but can also improve the mechanistic study of EoE that can ultimately be used to provide personalized treatments based on the unique expression of each patient. Such personalized treatments include guidance for determining appropriate medication dosages or treatment protocols to use in a given patient. Personalized treatment also allows for the modification of medication dosage or treatment protocols as necessary.

The diagnostic method is carried out on a patient to determine if the patient has eosinophilic esophatigis (EoE). RNA extraction is performed on a patient esophageal biopsy tissue sample. After RNA quantity/quality measurement by nanodrop, 1000 ng of the RNA sample is measured for the reverse transcription (RT) reaction. cDNA corresponding to 500 ng RNA is mixed with a qPCR amplification cocktail (such as, for example, Taqman Master Mix) and loaded onto the 384 well fluidic card (4 patients per 384 well card with 96 genes per patient). The cDNA is amplified with a real-time qPCR system (e.g. ABI 7900 HT system). The analysis step is performed in qPCR analysis software (e.g. Genespring software), and the qPCR raw data is subjected to the dendogram and/or EoE scoring algorithms as disclosed herein, or other algorithms, or other analysis of the results to obtain relatedness information relative to an EoE cohort, in order to establish an EoE diagnosis, which serves as the basis for the final diagnostic report. Based on the final diagnostic report, prognosis is provided, and/or a specific therapy is developed, and/or an ongoing therapy is modified, based upon the specific EoE transcription profile generated for the patient.

Example 20

Evaluation of an Archived Sample from a Patient

The EDP panel also has the capacity to differentiate the EoE and NL transcriptome from FFPE samples (Example 8). While FFPE samples are normally associated with relatively degraded RNA due to oxidation degradation during archiving (April, et al. *PloS One* 4:e8162 (2009)), the data presented herein indicate that the EDP is practically tolerant to the poor RNA integrity of FFPE samples. With RNA extraction from FFPE samples becoming a more readily available technique, molecular diagnosis from FFPE biopsy samples will allow for the retrospective study of the large amount of archived FFPE samples in various institution. FFPE samples are also normally associated with longer follow-up and more clinical outcomes, rendering them suitable for a long-term clinical study focusing on prognosis. Despite the poor RNA integrity of FFPE-derived RNA, the corresponding short-amplicon design of the EDP enables an unaffected capture of the EoE expression signature. There are fewer significant genes between EoE and NL in FFPE samples due to the smaller sample size rather than a degradation-related call rate issue because when co-clustered with fresh samples based on the 77 genes, a retained signature was acquired, rendering the FFPE samples undistinguishable from their fresh counterparts.

The FFPE capacity of the EDP as disclosed herein can make long term retrospective study possible without recruiting new samples. In addition, since FFPE sections can be sent at ambient temperature and are relatively less sensitive to decay, multi-centered studies can be performed in a more convenient manner in terms of logistics. The usage of already obtained clinical biopsy specimens combined with the merits of molecular diagnosis can reduce the number of biopsies procured during endoscopy.

Example 21

Determination of Inactive Eosinophilic Esophagitis in a Patient

The diagnostic method is carried out on a patient to determine if a patient has inactive eosinophilic esophatigis (EoE) molecular pathology as distinguished from normal molecular pathology. RNA extraction is performed on a patient esophageal biopsy tissue sample. After RNA quantity/quality measurement by nanodrop, 1000 ng of the RNA sample is measured for the reverse transcription (RT) reaction. cDNA corresponding to 500 ng RNA is mixed with a qPCR amplification cocktail (such as, for example, Taqman Master Mix) and loaded onto the 384 well fluidic card (4 patients per 384 well card with 96 genes per patient). The cDNA is amplified with a real-time qPCR system (e.g. ABI 7900 HT system). The analysis step is performed in qPCR analysis software (e.g. Genespring software), and the qPCR raw data is subjected to the dendogram and/or EoE scoring algorithms as disclosed herein to determine the EoE status in the patient, which serves as the basis for the final diagnostic report.

The diagnostic method is carried out on an archived FFPE sample from a patient to evaluate the patient's condition for EoE. RNA extraction is performed on the archived sample. After RNA quantity/quality measurement by nanodrop, 1000 ng of the RNA sample is measured for the reverse transcription (RT) reaction. cDNA corresponding to 500 ng RNA is mixed with a qPCR amplification cocktail (such as, for example, Taqman Master Mix) and loaded onto the 384 well fluidic card (4 patients per 384 well card with 96 genes per patient). The cDNA is amplified with a real-time qPCR system (e.g. ABI 7900 HT system). The analysis step is performed in qPCR analysis software (e.g. Genespring software), and the qPCR raw data is subjected to the dendogram and/or EoE scoring algorithms as disclosed herein, or other algorithms, or other analysis of the results to obtain relatedness information relative to an EoE cohort, in order to establish an EoE diagnosis, which serves as the basis for the final diagnostic report.

Example 22

Determination of EDP Genes Targeted by Therapeutics

The EDP can be used to determine if a particular drug is engaging a specific target on the EDP. For example, the EDP can be used to determine if an anti-IL-13 treatment down-regulated IL-13-related markers within the EDP.

The diagnostic method is carried out on a patient to determine the genes of the EDP with which a particular therapeutic is interacting. RNA extraction is performed on an esophageal biopsy tissue sample from a patient to whom a therapeutic has been administered. After RNA quantity/quality measurement by nanodrop, 1000 ng of the RNA sample is measured for the reverse transcription (RT) reaction. cDNA corresponding to 500 ng RNA is mixed with a qPCR amplification cocktail (such as, for example, Taqman Master Mix) and loaded onto the 384 well fluidic card (4 patients per 384 well card with 96 genes per patient). The cDNA is amplified with a real-time qPCR system (e.g. ABI 7900 HT system). The analysis step is performed in qPCR analysis software (e.g. Genespring software), and the qPCR raw data is subjected to the dendogram and/or EoE scoring algorithms as disclosed herein, or other algorithms, or other analysis of the results to obtain relatedness information relative to an EoE cohort, in order to establish an EoE diagnosis, which serves as the basis for the final diagnostic report. The result set is evaluated to identify from the result set the genes that are up- or down-regulated in response to the therapeutic.

Example 23

Determination of Hereditary DNA Variants on the Expression of EDP Genes

The EDP can be used to identify or monitor the impact of environmental factors (e.g., exposures), in particular as they relate to modification of esophageal epigenetics. For example, administered therapeutics can modify the response to such environmental factors.

The diagnostic method is carried out on a patient to determine the genes of the EDP which have been up- or down-regulated in response to environmental factors. RNA extraction is performed on an esophageal biopsy tissue sample from a patient to whom a therapeutic has been administered. After RNA quantity/quality measurement by nanodrop, 1000 ng of the RNA sample is measured for the reverse transcription (RT) reaction. cDNA corresponding to 500 ng RNA is mixed with a qPCR amplification cocktail (such as, for example, Taqman Master Mix) and loaded onto the 384 well fluidic card (4 patients per 384 well card with 96 genes per patient). The cDNA is amplified with a real-time qPCR system (e.g. ABI 7900 HT system). The analysis step is performed in qPCR analysis software (e.g. Genespring software), and the qPCR raw data is subjected to the dendogram and/or EoE scoring algorithms as disclosed herein, or other algorithms, or other analysis of the results to obtain relatedness information relative to an EoE cohort, in order to establish an EoE diagnosis, which serves as the basis for the final diagnostic report. The result set is evaluated relative to normal and EoE cohorts to identify from the result set the genes that are up- or down-regulated in response to environmental factors.

Example 24

Determination of Hereditary DNA Variants on the Expression of EDP Genes

The EDP can be used to determine the impact of hereditary DNA variants on the expression of EDP genes. This is accomplished via expression quantitative trait loci (QTL) analysis.

In having a readily obtainable expression profile with biological significance, the EDP provides an opportunity to screen the human genome for genetic variants that are responsible for various clinical phenotypes. These genetic loci can serve as susceptibility loci (with diagnostic merit) as well as targets for drug development and pharmacogenomic predictive medicine.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09928344B2). An electronic copy of the "Sequence Listing" will also be available from the USPTO upon request and payment of the fee set forth in 37 CFR 1.19(b)(3).

What is claimed is:

1. A method of diagnosing and treating eosinophilic esophagitis (EoE) in a subject, the method comprising:
   determining an amount of gene product in a sample from the subject for at least 10 of the genes identified in Table 1 by applying the sample to a diagnostic panel consisting of 10 or more of the genes identified in Table 1, wherein the at least 10 of the genes identified in Table 1 includes at least one gene selected from the group consisting of NEFM, RUNX2, TRIM2, CDH20, FCGR3B, FCGR3A, EPX, SLAMF7, and NCAM1;
   obtaining a cumulative gene expression result for the subject by summing the amounts of gene product in the sample for each of the genes in the diagnostic panel;
   comparing the cumulative gene expression result of the subject to a predetermined diagnostic cutoff determined by analyzing the cumulative gene expression results of the diagnostic panel from a cohort of normal individuals and a cohort of EoE patients to determine the diagnostic cutoff for the EoE state;
   making a determination as to the EoE status of the subject based upon whether the subject's cumulative gene expression result is within or outside the diagnostic cutoff; and
   treating the subject determined to have EoE with one or more therapies selected from administration of a glucocorticoid and an elimination diet.

2. The method of claim 1, wherein the diagnostic panel further comprises one or more of the genes TNFAIP6, ALOX15, CCL26, NEFL, PMCH, CXCL1, LRRC31, APOBEC3A, GLDC and CD200R1.

3. The method of claim 1, wherein the diagnostic panel further comprises one or more of the genes TNFAIP6, ALOX15, NEFL, PMCH, CXCL1, APOBEC3A, POSTN, IL8, ANO1, SLC26A4, SUSD2, CPA3, CXCL6, CCL26, LRRC31, GLDC, CD200R1, CDH26, EPPK1 and IL13.

4. The method of claim 1, wherein the diagnostic panel further comprises one or more of the genes DSG1, CRISP3, CRYM, CLDN10, CDA, GYS2, ACTG2, CRISP2, ARG1 and IGFL1.

5. The method of claim 1, wherein the diagnostic panel further comprises one or more of the genes DSG1, CRISP3, CRYM, CLDN10, CDA, GYS2, ACTG2, CRISP2, ARG1, IGFL1, EML1, ENDOU, C7orf68, UPK1A, ZNF365, MT1M, PNLIPRP3, ALOX12, TSPAN12 and SPINK7.

6. The method of claim 1, wherein the diagnostic panel comprises the 77 genes identified in Table 2.

7. The method of claim 1, wherein the sample is a tissue.

8. The method of claim 7, wherein the tissue is esophageal tissue.

9. The method of claim 7, wherein the tissue is formalin-fixed, paraffin embedded tissue.

10. The method of claim 1, wherein the amounts of gene product for the at least 10 genes are obtained by subjecting the sample to quantitative gene expression analysis using a polymerase chain reaction (qPCR).

11. The method of claim 10, wherein the amounts of gene product for the at least 10 genes are expression values for each gene of the diagnostic panel.

12. The method of claim 11, wherein the expression values are cycle threshold (Ct) values.

13. The method of claim 1, further comprising one or more of the following steps performed prior to the step of applying the sample from the subject to the diagnostic panel: extracting RNA from the sample, subjecting RNA from the sample to reverse transcription, and obtaining cDNA from the sample.

14. The method of claim 1, wherein the diagnostic panel comprises 59 of the genes identified in Table 1.

15. The method of claim 1, wherein the diagnostic panel comprises 77 of the genes identified in Table 1.

16. The method of claim 1, wherein the diagnostic panel comprises 94 of the genes identified in Table 1.

17. The method of claim 1, wherein the predetermined diagnostic cutoff is determined using a receiver operating characteristic (ROC) analysis.

18. The method of claim 1, wherein the sample is a blood sample.

19. A method of diagnosing and treating eosinophilic esophagitis (EoE) in a subject, the method comprising:
   determining an amount of gene product in a sample from the subject for at least 10 of the genes identified in Table 1 by applying the sample to a diagnostic panel consisting of 10 or more of the genes identified in Table 1, wherein the at least 10 of the genes identified in Table 1 includes at least one gene selected from the group consisting of NEFM, RUNX2, TRIM2, CDH20, FCGR3B, FCGR3A, EPX, SLAMF7, and NCAM1;
   obtaining a cumulative gene expression result for the subject by summing the amounts of gene product in the sample for each of the genes in the diagnostic panel;
   comparing the cumulative gene expression result of the subject to a predetermined diagnostic cutoff determined by analyzing the cumulative gene expression results of the diagnostic panel from a cohort of normal individuals and a cohort of EoE patients to determine the diagnostic cutoff for the EoE state;
   making a determination as to the EoE status of the subject based upon whether the subject's cumulative gene expression result is within or outside the diagnostic cutoff; and treating the subject determined to have EoE with an anti-T lymphocyte therapy.

20. The method of claim 19, wherein the diagnostic panel further comprises one or more genes selected from IL4, IL5, and IL13.

21. The method of claim 19, wherein the diagnostic panel further comprises IL13.

22. The method of claim 19, wherein the anti-T lymphocyte therapy is a therapy that targets at least one of IL4, IL5, and IL13.

23. The method of claim 19, wherein the anti-T lymphocyte therapy is a therapy that targets IL13.

24. The method of claim 19, wherein the diagnostic panel further comprises one or more of TNFAIP6, ALOX15, CCL26, NEFL, PMCH, CXCL1, LRRC31, APOBEC3A, GLDC and CD200R1.

25. The method of claim 19, wherein the diagnostic panel further comprises one or more of TNFAIP6, ALOX15, NEFL, PMCH, CXCL1, APOBEC3A, POSTN, IL8, ANO1, SLC26A4, SUSD2, CPA3, CXCL6, CCL26, LRRC31, GLDC, CD200R1, CDH26, EPPK1 and IL13.

26. The method of claim 19, wherein the diagnostic panel further comprises one or more of DSG1, CRISP3, CRYM, CLDN10, CDA, GYS2, ACTG2, CRISP2, ARG1 and IGFL1.

27. The method of claim 19, wherein the diagnostic panel further comprises one or more of DSG1, CRISP3, CRYM, CLDN10, CDA, GYS2, ACTG2, CRISP2, ARG1, IGFL1, EML1, ENDOU, C7orf68, UPK1A, ZNF365, MT1M, PNLIPRP3, ALOX12, TSPAN12 and SPINK7.

28. The method of claim 19, wherein the diagnostic panel comprises the 77 genes identified in Table 2.

29. The method of claim 19, wherein the sample is a tissue.

30. The method of claim 29, wherein the tissue is esophageal tissue.

31. The method of claim 29, wherein the tissue is formalin-fixed, paraffin embedded tissue.

32. The method of claim 19, wherein the amounts of gene product for the at least 10 genes are obtained by subjecting the sample to quantitative gene expression analysis using a polymerase chain reaction (qPCR).

33. The method of claim 32, wherein the amounts of gene product for the at least 10 genes are expression values for each gene of the diagnostic panel.

34. The method of claim 33, wherein the expression values are cycle threshold (Ct) values.

35. The method of claim 19, further comprising one or more of the following steps performed prior to the step of applying the sample from the subject to the diagnostic panel: extracting RNA from the sample, subjecting RNA from the sample to reverse transcription, and obtaining cDNA from the sample.

36. The method of claim 19, wherein the diagnostic panel comprises 59 of the genes identified in Table 1.

37. The method of claim 19, wherein the diagnostic panel comprises 77 of the genes identified in Table 1.

38. The method of claim 19, wherein the diagnostic panel comprises 94 of the genes identified in Table 1.

39. The method of claim 19, wherein the predetermined diagnostic cutoff is determined using a receiver operating characteristic (ROC) analysis.

40. The method of claim 19, wherein the sample is a blood sample.

* * * * *